United States Patent
Arai et al.

(10) Patent No.: US 6,329,479 B1
(45) Date of Patent: *Dec. 11, 2001

(54) TRANSITION METAL COMPOUND AS CATALYST COMPONENT FOR POLYMERIZATION, AROMATIC VINYL COMPOUND-OLEFIN COPOLYMER HAVING STEREOREGULARITY AND METHOD FOR ITS PREPARATION BY MEANS OF THE TRANSITION METAL COMPOUND AS CATALYST COMPONENT

(75) Inventors: Toru Arai; Toshiaki Otsu; Shigeru Suzuki; Masataka Nakajima, all of Machida (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/390,711

(22) Filed: Sep. 7, 1999

Related U.S. Application Data

(63) Continuation-in-part of application No. 09/048,000, filed on Mar. 26, 1998, now Pat. No. 6,235,855.

(30) Foreign Application Priority Data

Apr. 17, 1997 (JP) .................................... 9-100527
Apr. 17, 1997 (JP) .................................... 9-100528

(51) Int. Cl.[7] ................................ C08F 4/64; C08F 12/04
(52) U.S. Cl. .................... 526/170; 526/126; 526/127; 526/131; 526/132; 526/134; 526/160; 526/346; 526/347; 526/348; 526/943
(58) Field of Search ................... 526/160, 170, 526/346, 347, 348, 126, 127, 131, 132, 134, 943

(56) References Cited

U.S. PATENT DOCUMENTS

| | | | |
|---|---|---|---|
| 5,043,408 | * 8/1991 | Kakugo et al. | 526/347 |
| 5,210,338 | * 5/1993 | Samsel | 568/911 |
| 5,543,484 | * 8/1996 | Chung et al. | 526/348 X |
| 5,652,315 | 7/1997 | Inoue et al. | 526/126 X |
| 5,658,625 | 8/1997 | Bradfute et al. | |
| 5,703,187 | 12/1997 | Timmers | 529/153 |
| 5,883,213 | 3/1999 | Arai et al. | 526/126 X |
| 6,066,709 | 5/2000 | Arai et al. | |
| 6,235,855 | * 5/2001 | Arai et al. | 526/347 X |

FOREIGN PATENT DOCUMENTS

| | | |
|---|---|---|
| 197 11 339 | 10/1997 | (DE) . |
| 0 405 446 | 1/1991 | (EP) . |
| 0 418 815 | 3/1991 | (EP) . |
| 0 872 492 | 10/1998 | (EP) . |
| WO 94/00500 | 1/1994 | (WO) . |
| WO 95/32095 | 11/1995 | (WO) . |
| WO 98/09999 | 3/1998 | (WO) . |

OTHER PUBLICATIONS

F.G. Sernetz et al., Journal of Polymer Science Part A: Polymer Chemistry, vol. 35, No. 8, pps. 1571–1578, "Copolymerization of Ethene with Styrene Using Different Methylalumoxane Activated Half–Sandwich Complexes", 1997.

T. Arai, et al., Macromol. Rapid Commun., vol. 19, pps. 327–331, "Steroregular and Bernoullian Copolymerization of Styrene and Ethylene by Bridged Metallocene Catalysts", 1998.

Stud. Surf. Sci. Catal. pp. 517–529, 1990.

J. Appl. Polym. Sci., 53, pp. 1453–1460, 1994.

Derwent Publications, AN 1989–170557, JP 01 113447, May 2, 1989.

Japanese Unexamined Patent Publication JP–4–130114.

* cited by examiner

Primary Examiner—Fred Teskin
(74) Attorney, Agent, or Firm—Oblon, Spivak, McClelland, Maier & Neustadt, P.C.

(57) ABSTRACT

A transition metal compound of the following formula (1) as catalyst component for the production of an aromatic vinyl compound polymer or an aromatic vinyl compound-olefin copolymer:

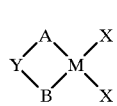

(1)

wherein A is a specified unsubstituted or substituted benzindenyl group, and B, M, Y, and X are as specified.

4 Claims, 53 Drawing Sheets

TRANSITION METAL COMPOUND AS CATALYST COMPONENT FOR POLYMERIZATION, AROMATIC VINYL COMPOUND-OLEFIN COPOLYMER HAVING STEREOREGULARITY AND METHOD FOR ITS PREPARATION BY MEANS OF THE TRANSITION METAL COMPOUND AS CATALYST COMPONENT

This application is a continuation in part of U.S. patent application Ser. No. 09/048,000 filed Mar. 26, 1998, now U.S. Pat. No. 6,235,855 and incorporated entirely herein by reference.

The present invention relates to a transition metal compound as catalyst component for polymerization, a method for producing an aromatic vinyl compound type polymer employing it, a method for producing an aromatic vinyl compound polymer and an aromatic vinyl compound-olefin copolymer, having an isotactic stereoregularity, and a novel aromatic vinyl compound-olefin copolymer.

Also, the present invention provides a non-crystalline aromatic vinyl compound-ethylene random copolymer having a high random property (low alternating property) of novel structure, having an isotactic stereoregularity and having a feature that even after sufficiently subjecting to crystallization, a crystallinity derived from an aromatic vinyl compound-ethylene alternating structure is not observed. Further, the present invention provides a novel transition metal compound for as catalyst component for polymerization.

For the production of a copolymer of an olefin with an aromatic vinyl compound, such as ethylene with styrene, studies have been conducted primarily by using so-called heterogeneous Ziegler-Natta catalysts (e.g. Polymer Bulletin, 20, 237–241 (1988), Macromolecules, 24, 5476 (1991)). However, conventional heterogeneous Ziegler-Natta catalyst systems are not so practical, since the catalytic activities are low, the styrene content in the product is very low at a level of a 1 mol %, or the product does not have a uniform regular copolymer structure or contains a substantial amount of homopolymers such as polyethylene and isotactic or atactic polystyrene.

Further, the stereoregularity of the obtained polystyrene is isotactic, but in the copolymerization, no stereoregularity of an alternating structure of styrene and an olefin is observed, or an alternating structure itself is not substantially contained.

Further, some styrene-ethylene copolymers obtainable by using so-called single-site catalyst systems comprising a transition metal compound and an organoaluminum compound, and methods for their production, have been known.

JP-A-3-163088 and JP-A-7-53618 disclose styrene-ethylene copolymers where no normal styrene chain is present i.e. so-called pseudo random copolymers, obtained by using a complex having a so-called constrained geometrical structure. Here, a normal styrene chain is meant for a head-to-tail bond chain. Further, hereinafter styrene may sometimes be represented by St.

However, phenyl groups in the alternating structure of styrene-ethylene present in such pseudo random copolymers, have no stereoregularity. Further, no normal styrene chain is present, whereby the content of styrene can not exceed 50 mol %. Further, the catalytic activities are practically inadequate.

JP-A-6-49132 and Polymer Preprints, Japan, 42, 2292 (1993) disclose methods for producing similar styrene-ethylene copolymers wherein no normal St chain is present, i.e. so-called pseudo random copolymers, by using a catalyst comprising a bridged metallocene type Zr complex and a cocatalyst.

However, according to Polymer Preprints, Japan, 42, 2292 (1993), phenyl groups in the alternating structure of styrene-ethylene present in such pseudo random copolymers, have no substantial stereoregularity. Further, like in the case of a complex having a constrained geometrical structure, no normal styrene chain is present, and the styrene content can not exceed 50 mol %. The catalytic activities are also practically inadequate.

Further, it has recently been reported to produce a styrene-ethylene copolymer close to an alternating copolymer having a stereoregularity under a condition of an extremely low temperature (−25° C.) by using 1,2-ethylene (—$CH_2$—$CH_2$—) bridged bisindenyl type Zr complex; rac [ethylenebis(indenyl)zirconium dichloride] (Macromol. Chem., Rapid Commun., 17, 745 (1996)).

However, from the 13C-NMR spectrum disclosed, it is evident that this copolymer has no normal styrene chain. Further, if copolymerization is carried out at a polymerization temperature of at least room temperature by using this complex, only a copolymer having a low styrene content and a low molecular weight is obtainable.

On the other hand, a styrene-ethylene alternating copolymer obtainable by using a Ti complex having a substituted phenol type ligand, is known (JP-A-3-250007 and Stud. Surf. Sci. Catal., 517 (1990)). This copolymer has a feature that it consists essentially of an alternating structure of ethylene and styrene and contains substantially no other structure such as an ethylene chain, a structure comprising an ethylene chain and styrene or a structure of e.g. a head-to-head or tail-to-tail bond (hereinafter referred to as a heterogeneous bond) of styrene. The alternating index (value λ in the present specification) of the copolymer is at least 70, substantially at least 90.

Namely, the resulting copolymer is a copolymer having a very high degree of alteration and consisting substantially solely of the alternating structure, whereby it is substantially difficult to change the compositional ratio of the copolymer consisting of 50 mol % of ethylene and 50 mol % of styrene. Further, the stereoregularity of phenyl groups is isotactic, but the isotactic diad index m is about 0.92, whereby the melting point is low at a level of from 110 to 120° C.

Further, the weight average molecular weight is low at a level of 20,000, which is inadequate to provide practically useful physical properties as a crystalline polymer. It should also be added that the catalytic activities are very low, and the copolymer can hardly be regarded as practically useful, since it is obtained as a mixture with e.g. syndiotactic polystyrene.

It has been attempted to produce a copolymer of a propylene with styrene by means of a Solvay type Ziegler-Natta catalyst (Macromolecules, 22, 2875 (1989)). However, the catalytic activities are low, and the styrene content is at a level of 4.4 mol % at best. With respect to a single-site catalyst system comprising a transition metal compound and an organoaluminum compound, a case wherein a Ewen-type zirconium complex which is a so-called metallocene catalyst, is employed for copolymerization of propylene with styrene, is known (JP-A-8-269134). However, the styrene content of the copolymer thereby obtainable is as low as a few %, and the stereoregularity is syndiotactic.

The production of an isotactic aromatic vinyl compound polymer such as an isotactic polystyrene, has been studied by means of a so-called heterogeneous Ziegler-Natta catalyst.

For example, such a catalyst is disclosed in Macromolecules, 24, 5476 (1991), but the catalytic activities are low, and as a fate of a heterogeneous Ziegler-Natta catalyst, due to non-uniform active sites, the molecular weight distribution (Mw/Mn) tends to be as broad as at least 3, and cation polymerization and other polymerizations tend to simultaneously proceed, and a substantially a large amount of atactic polystyrene is usually produced as a by-product.

On the other hand, in the polymerization of styrene using a single-site catalyst, syndiotactic polystyrene is usually obtained. Only when a nickel-type non-metallocene complex is used, formation of isotactic polystyrene has been reported, for example, in Macromolecules, 29, 4172 (1996). However, the molecular weight, the catalytic activities and the stereoregularities are all inadequate.

In any case, no isotactic polystyrene has been obtained with a system using a metallocene complex as a catalyst component.

It is an object of the present invention to provide a metal compound for polymerization, a method for producing an aromatic vinyl compound type stereoregular polymer by using it, a method for producing an aromatic vinyl compound polymer and an aromatic vinyl compound-olefin copolymer, having isotactic stereoregularity, and a novel aromatic vinyl compound-olefin copolymer.

It is another object of the present invention to provide an aromatic vinyl compound-ethylene random copolymer having a high random property (low alternating property) and having substantially no crystallinity derived from alternating structure.

Firstly, the present invention provides a transition metal compound of the following formula (1) as catalyst component for the production of an aromatic vinyl compound polymer or an aromatic vinyl compound-olefin copolymer:

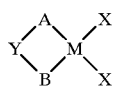
(1)

wherein A is an unsubstituted or substituted benzindenyl group of the following formula K-2, K-3 or K-4:

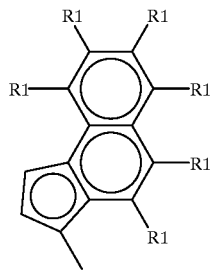
(K-2)

(K-3)

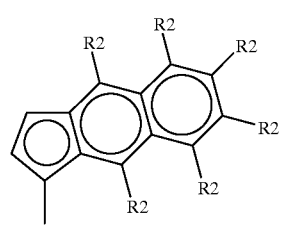

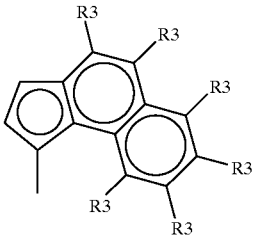
(K-4)

wherein each of R1 to R3 is hydrogen, a $C_{1-20}$ alkyl group, a $C_{6-10}$ aryl group, a $C_{7-20}$ alkylaryl group, a halogen atom, $OSiR_3$, $SiR_3$, or $PR_2$ (wherein each R is a $C_{1-10}$ hydrocarbon group), provided that the plurality of R1, the plurality of R2 and the plurality of R3 may be the same or different, respectively, and each pair of adjacent R1, adjacent R2 and adjacent R3 may together, with the atoms joining them, form a 5- to 8-member aromatic or aliphatic ring, In the formulas K-2 and K-4, when each pair of adjacent RI and adjacent R3 form a 6-member ring together with carbon atoms, i.e. a cyclopentaphenanthryl group, it is a substituted cyclopentaphenanthryl group expressed by the formula J-1 or J-2;

(J-1)

(J-2)

(In the above formulas J-1 and J-2, each of R11 and R22 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), provided that the plurality of R11 and the plurality of R22 may be the same or different, respectively, and each pair of adjacent R11 and adjacent R22 may, together with the atoms joining them, form one or more 5- to 8-membered aromatic or aliphatic ring, except for a case that all of the substituents are hydrogen.)

B is an unsubstituted or substituted cyclopentaphenanthryl group, or an unsubstituted or substituted benzindenyl group of the same chemical formula as A, or an unsubstituted or substituted cyclopentadienyl group, an unsubstituted or substituted indenyl group or an unsubstituted or substituted fluorenyl group, of the following formula K-5, K-6 or K-7;

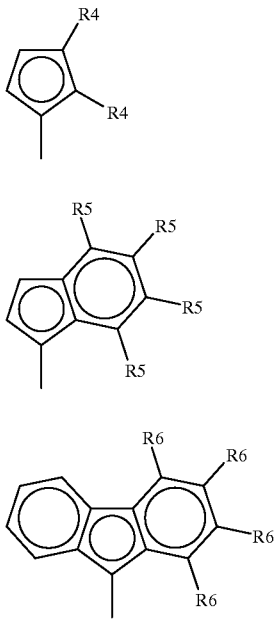

(K-5)

(K-6)

(K-7)

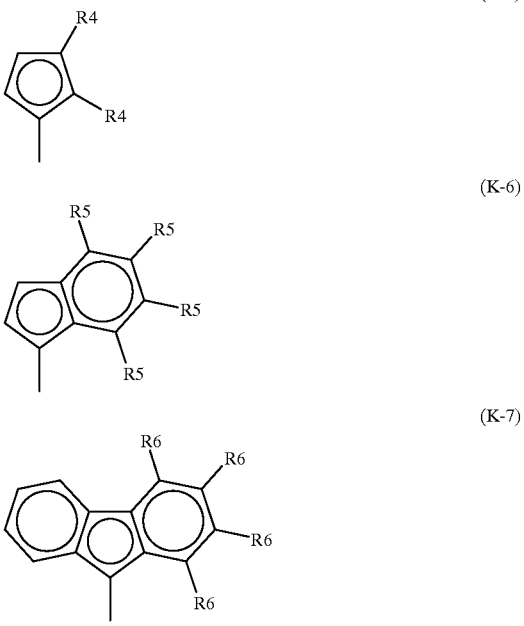

(K-5)

(K-6)

(K-7)

wherein each of R4 to R6 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$, (wherein each R is a $C_{1-10}$ hydrocarbon group), provided that the plurality of R4, the plurality of R5 and the plurality of R6 may be the same or different, respectively, when both A and B are unsubstituted or substituted benzindenyl groups, they may be the same or different, Y is a methylene group or a silylene group, which has bonds to A and B and which has, as substituents, hydrogen or a $C_{1-15}$ hydrocarbon group, wherein the substituents may be the same or different from each other, or Y may have, together with the substituents, a cyclic structure, X is hydrogen, a halogen atom, an alkyl group, an aryl group, an alkylaryl group, a silyl group, a methoxy group, an ethoxy group, an alkoxy group or a dialkylamide group, and M is zirconium, hafnium or titanium.

The unsubstituted benzindenyl group may, for example, be 4,5-benz-1-indenyl (another name: benz(e)indenyl), 5,6-benz-1-indenyl, or 6,7-benz-1-indenyl, and the substituted benzindenyl group may, for example, be 4,5-naphtho-1-indenyl, 4,5-pyrene-1-indenyl, 4,5-triphenylene-1-indenyl, a-acenaphtho-1-indenyl, 3-cyclopenta[c]phenanthryl or 1-cyclopenta[1]phenanthryl.

Particularly preferably, the unsubstituted benzindenyl may, for example, 4,5-benz-1-indenyl (another name: benz(e)indenyl), 5,6-benz-1-indenyl, or 6,7-benz-1-indenyl, and the substituted benzindenyl group may, for example, be α-acenaphtho-1-indenyl, 3-cyclopenta[c]phenanthryl, or 1-cyclopenta[1]phenanthryl.

In the above formula (1), B is preferably the same unsubstituted or substituted benzindenyl group as above A, or an unsubstituted or substituted cyclopentadienyl group, an unsubstituted or substituted indenyl group or an unsubstituted or substituted fluorenyl group, of the following formula K-5, K-6 or K-7:

In the above K-5 to K-7, each of R4, R5 and R6 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), the plurality of R4, the plurality of R5 and the plurality of R6 may be the same or different, respectively. However, B is preferably in a racemic-form (or pseudo racemic-form) with A.

Particularly preferably, B is, as an unsubstituted benzindenyl group, 4,5-benz-1-indenyl, 5,6-benz-1-indenyl or 6,7-benz-1-indenyl, or as a substituted benzindenyl group, α-acenaphtho-1-indenyl, 3-cyclopenta[c]phenanthryl, or 1-cyclopenta[1]phenanthryl, or as an unsubstituted indenyl group, 1-indenyl, or as a substituted indenyl group, 4-phenylindenyl or 4-naphthylindenyl.

The unsubstituted cyclopentadienyl may, for example, be cyclopentadienyl, and the substituted cyclopentadienyl may, for example, be 4-aryl-1-cyclopentadienyl, 4,5-diaryl-1-cyclopentadienyl, 5-alkyl-4-aryl-1-cyclopentadienyl, 4-alkyl-5-aryl-1-cyclopentadienyl, 4,5-dialkyl-1-cyclopentadienyl, 5-trialkylsilyl-4-alkyl-1-cyclopentadienyl, or 4,5-dialkylsilyl-1-cyclopentadienyl.

The unsubstituted indenyl group may, for example, be 1-indenyl, and the substituted indenyl group may, for example, be 4-alkyl-1-indenyl, 4-aryl-1-indenyl, 4,5-dialkyl-1-indenyl, 4,6-dialkyl-1-indenyl, 5,6-dialkyl-1-indenyl, 4,5-diaryl-1-indenyl, 5-aryl-1-indenyl, 4-aryl-5-alkyl-1-indenyl, 2,6-dialkyl-4-aryl-1-indenyl, 5,6-diaryl-1-indenyl, or 4,5,6-triaryl-1-indenyl.

The unsubstituted fluorenyl group may, for example, be a 9-fluorenyl group, and the substituted fluorenyl group may, for example, be a 7-methyl-9-fluorenyl group or a benz-9-fluorenyl group.

In the above formula (1), Y is carbon or silicon which has bonds to A and B and which has substituents, and it is a methylene group or a silylene group having, as substituents, hydrogen or a $C_{1-15}$ hydrocarbon group.

The substituents may be the same or different from each other. Further, Y may have a cyclic structure such as a cyclohexylidene group or a cyclopentylidene group.

Preferably, Y is a substituted methylene group which has bonds to A and B and which is substituted by hydrogen or a $C_{1-15}$ hydrocarbon group. The hydrocarbon group may, for example, be an alkyl group, an aryl group, a cycloalkyl group or a cycloaryl group. The substituents may be the same or different from each other.

Particularly preferably, Y is —$CH_2$—, —$CMe_2$—, —$CEt_2$—, —$CPh_2$—, cyclohexylidene or cyclopentylidene. Here, Me is a methyl group, Et is an ethyl group and Ph is a phenyl group.

X is hydrogen, a halogen atom, a $C_{1-15}$ alkyl group, a $C_{6-10}$ aryl group, a $C_{8-12}$ alkylaryl group, a silyl group having a $C_{1-4}$ hydrocarbon substituent, a $C_{1-10}$ alkoxy group, or a dialkylamide group having a $C_{1-6}$ alkyl substituent. The halogen atom may, for example, be chlorine or bromine, the alkyl group may, for example, be a methyl group or an ethyl group, and the aryl group may, for example, be a phenyl group. The alkylaryl group may, for example, be a benzyl group, the silyl group may, for example, be trimethylsilyl, the alkoxy group may, for example, be a methoxy group, an ethoxy group or an isopropoxy group, and the dialkylamide group may, for example, be a dimethylamide group. X may be the same or different from each other, or having a bond structure between X.

Especially when X is a dimethylamide group, the transition metal catalyst component of the present invention can be produced by the method disclosed in WO95/32979, whereby there is a merit that such a catalyst component can simply and inexpensively be produced. Namely, it can be produced by a single step from a ligand compound and zirconium tetrakisdimethylamide at a temperature of at least room temperature, where control is easy. Strictly, the transition metal catalyst component produced by this process is a racemic-form containing a substantial amount of meso-form as an impurity. However, inclusion of the meso-form in the catalyst gives no substantial influence in the present invention.

In the case of a transition metal complex wherein X is chlorine, a highly costly process for reacting a dimethylamide type complex with a dimethylamine hydrochloride at a low temperature, such as −78° C. is required, whereby the product will be expensive.

Further, when X is a dimethylamide, the speed for forming active species after contacting with methylalumoxane as the cocatalyst, tends to be slightly slow as compared with a case where X is chlorine. This has an important merit from the viewpoint of the production process in that particularly in a batch solution polymerization, in a polymerization method of preliminarily dissolving a cocatalyst in the polymerization solution and introducing a transition metal compound to the polymerization solution under prescribed condition to initiate the polymerization, active species are gradually formed during the polymerization, whereby abrupt generation of polymerization heat immediately after the introduction of the catalyst can be reduced, and heat removal of the polymerization liquid can be facilitated.

M is zirconium, hafnium or titanium. Particularly preferred is zirconium.

The following compounds may be mentioned as specific examples of such a transition metal compound as catalyst component.

For example, dimethylmethylene bis(4,5-benz-1-indenyl)zirconium dichloride (another name: dimethylmethylenebis(benz-e-indenyl)zirconium dichloride), di-n-propylmethlenebis(4,5-benz-1-indenyl)zirconium dichloride, di-i-propylmethylenebis(4,5-benz-1-indenyl)zirconium dichloride, cyclohexylidenebis(4,5-benz-1-indenyl)zirconium dichloride, cyclopentylidenebis(4,5-benz-1-indenyl)zirconium dichloride, diphenylmethylenebis (4,5-benz-1-indenyl)zirconium dichloride, dimethylmethylene(cyclopentadienyl)(4,5-benz-1-indenyl) zirconium dichloride, dimethylmethylene(1-indenyl)(4,5-benz-1-indenyl)zirconium dichloride, dimethylmethylene (1-fluorenyl)(4,5-benz-1-indenyl)zirconium dichloride, dimethylmethylene(4-phenyl- 1-indenyl)(4,5-benz-1-indenyl)zirconium dichloride, dimethylmethylene(4-naphthyl-1-indenyl)(4,5-benz-1-indenyl)zirconium dichloride, dimethylmethylenebis(5,6-benz-1-indenyl) zirconium dichloride, dimethylmethylene(5,6-benz-1-indenyl)(1-indenyl)zirconium dichloride, dimethylmethylenebis(4,7-benz-1-indenyl)zirconium dichloride, dimethylmethylene(6,7-benz-1-indenyl)(1-indenyl)zirconium dichloride, dimethylmethylenebis(4,5-naphtho-1-indenyl)zirconium dichloride, dimethylmethylenebis(α-acetonaphtho-1-indenyl) zirconium dichloride, dimethylmethylenebis(3-cyclopenta (c)phenanthryl)zirconium dichloride, dimethylmethylene(3-cyclopenta(c)phenanthryl)(1-indenyl)zirconium dichloride, dimethylmethylenebis(1-cyclopenta(1)phenanthryl) zirconium dichloride, dimethylmethylene(1-cyclopenta(1) phenanthryl) (1-indenyl)zirconium dichloride, dimethylmethylenebis(4,5-benz-1-indenyl)zirconium bis (dimethylamide), and dimethylmethylene(1-indenyl)(4,5-benz-1-indenyl)zirconium bis(dimethylamide), may be mentioned.

For example, dimethylmethylenebis(3-cyclopenta[c] phenanthryl)zirconium dichloride, di-n-propylmethylenebis (3-cyclopenta[c]phenanthryl)zirconium dichloride, di-i-propylmethylenebis(3-cyclopenta[c]phenanthryl)zirconium dichloride, cyclohexylidenebis(3-cyclopenta[c]phenanthryl) zirconium dichloride, cyclopentylidenebis(3-cyclopenta[c] phenanthryl)zirconium dichloride, diphenylinethylenebis(3-cylcopenta[c]phenanthryl) zirconium dichloride, dimethylmethylene(4,5-benzo-1-indenyl) (3-cylcopenta[c] phenanthryl)zirconium dichloride, dimethylmethylene(5,6-benzo-1-indenyl)(3-cyclopenta[c]phenanthryl)zirconium dichloride, dimethylmethylene(6,7-benzo-1-indenyl)(3-cyclopenta[c]phenanthryl)zirconium dichloride, dimethylmethylene(cyclopentadienyl)(3-cyclopenta[c] phenanthryl)zirconium dichloride, dimethylmethylene (1-fluorenyl)(3-cyclopenta[c]phenanthryl)zirconium dichloride, dimethylmethylene(4-phenyl-1-indenyl)(3-cyclopenta[c]phenanthryl)zirconium dichloride, dimethylmethylene(4-naphthyl-1-indenyl)(3-cyclopenta[c] phenanthryl)zirconium dichloride, dimethylmethylene(3-cyclopenta[c]phenanthryl)(4,5-naphto-1-indenyl)zirconium dichloride, dimethylmethylene(3-cyclopenta[c]phenanthryl (α-acenaphto-1-indenyl)zirconium dichloride, dimethylmethylenebis(1-cyclopenta[1]phenanthryl) zirconium dichloride, di-n-propylmethylenebis (1-cyclopenta[1]phenanthryl)zirconium dichloride, di-i-propylmethylenebis(1-cyclopenta[1]phenanthryl)zirconium dichloride, cyclohexylidenebis(1-cyclopenta[1]phenanthryl) zirconium dichloride, cyclopentylidenebis(1-cyclopenta[1] phenanthryl)zirconium dichloride, diphenylmethylenebis(1-cyclopenta[1]phenanthryl)zirconium dichloride, diphenylmethylene (4,5-benzo-1-indenyl)(1-cyclopenta[1] phenanthryl)zirconium dichloride, diphenylmethylene(5,6-benzo-1-indenyl)(1-cyclopenta[1]phenanthryl)zirconium dichloride, diphenylmethylene(6,7-benzo-1-indenyl)(1-cyclopenta[1]phenanthryl)zirconium dichloride, methylmethylene(cyclopentadienyl)(1-cyclopenta[1] iphenanthryl)zirconium dichloride, dimethylmethylene(1-fluorenyl)(1-cyclopenta[1]phenanthryl)zirconium dichloride, dimethylmethylene(4-phenyl-1-indenyl)(1-cyclopenta[1]phenanthryl)zirconium dichloride, dimethylmethylene(4-naphthyl-1-indenyl)(1-cyclopenta[1]phenanthryl)zirconium dichloride, dimethylmethylene(1-cyclopenta[1]phenanthryl)(4,5-naphtho-1-indenyl)zirconium dichloride, dimethylmethylene (1-cyclopenta[1]phenanthryl)(α-acenaphtho-1-indenyl)zirconium dichloride, dimethylmethylene(1-cyclopenta[1]phenanthryl)(3-cyclopenta[c]phenanthryl)zirconium dichloride, and the like.

In the foregoing, zirconium complexes were exemplified, but corresponding titanium complexes and hafnium complexes may also suitably be used. Further, racemic-form or mixtures of racemic-form and meso-form may also be employed. Preferably, racemic-form or pseudo racemic-form are employed. In such a case, D-isomers or L-isomers may be employed.

The following excellent characteristics are obtainable when an aromatic vinyl compound polymer or an aromatic vinyl compound-olefin copolymer is produced by using the transition metal compound of the present invention as a polymerization catalyst component.

The catalytic activities are high, and the polymer or the copolymer can be obtained at a high productivity of a level of at least $1 \times 10^8$ (g/mol·transition metal catalyst) in the case where the aromatic vinyl compound content is less than 20 mol %, or at least $4.1 \times 10^7$ (g/mol·transition metal catalyst) when the aromatic vinyl compound content is at least 20 mol % and less than 55 mol %.

Further, it is possible to produce a random copolymer having a high aromatic vinyl compound content, particularly an aromatic vinyl compound-ethylene random copolymer wherein the aromatic vinyl compound content exceeds 55 mol %.

Especially when a polymerization catalyst comprising a transition metal compound as catalyst component having a 3-cyclopenta(c)phenanthryl group as ligand A or A and B, such as rac-dimethylmethylenebis(3-cyclopenta(c)phenanthryl)zirconium dichloride, and a cocatalyst, is employed, it is possible to produce a styrene-olefin random copolymer, particularly a styrene-ethylene random copolymer, and an isotactic polystyrene, having a high molecular weight, under very high catalytic activities. In such a case, particularly with respect to a copolymer wherein the aromatic vinyl compound content is at least 50 mol %, it is possible to produce a copolymer having a weight average molecular weight of at least 100,000, preferably 200,000. Further, the styrene-ethylene random copolymer thereby obtained, has a characteristic that it is a copolymer having a high random nature (low alternating nature) as compared with a case with the same aromatic vinyl compound content under the same polymerization condition. The isotacticity of the structure contained in the resulting polymer or copolymer is very high.

Secondly, the present invention provides a transition metal compound of the following formula (2-1) or (2-2) as catalyst component for the production of an aromatic vinyl compound copolymer or an aromatic vinyl compound-olefin copolymer:

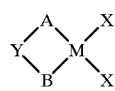

(2-1)

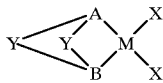

(2-2)

wherein A, B, Y, M and X are as defined with respect to the formula (1), wherein the angle (the bite angle) between metal M and the centroid of each cyclopentadienyl structure in A and B is at most 120°.

The bite angle can be obtained by X-ray diffraction of a single crystal of the transition metal catalyst component or by the following calculation method employing a computer.

SGI Origin Work Station was employed which has IRIX6.4 mounted as an operation system and which has MIPS R10000 Processo Chip Revision 2.6 2×180 MHz IP27 processors as CPU.

The employed softwares were Molecular orbital method G94revision, E. 2, Gaussian 94 (manufactured by Gaussian Inc.) and Option (Geom, OPT, HF, DIRECT, STO-3G).

The results of the study carried out with respect to dimethylmethylene(cyclopentadienyl)(fluorenyl)zirconium dichloride are shown below, which substantiate that the method of obtaining a bite angle by such a calculation, is proper.

Bite angle obtained by the above calculation method: 119° Bite angle obtained by single crystal X-ray diffraction method: 117.9°

Literature value: Macromol. Chem., Macromol. Symp., 48/49, 253 (1991).

The two values substantially agree, thus substantiating that the calculation method is proper.

| Formulas | Calculation results Y | Bite angle |
|---|---|---|
| Formula (2-1) | Dimethylmethylene group | 119' |
|  | Dimethylsilylene group | 126' |
| Formula (2-2) | Dimethylmethylene group | 111' |
|  | Dimethylsilylene group | 121' |

By variously changing the structures of A and B, bite angles were obtained by calculation, and such bite angles agreed to one another within a difference of 1°. Namely, the structures of A and B do not affect the bite angle.

The present inventors have studied the content of an aromatic vinyl compound in the aromatic vinyl compound-olefin copolymer under the same condition using various transition metal compound as catalyst components. As a result, it has been found that a very high aromatic vinyl compound content can be obtained when a transition metal catalyst component having a bite angle of at most 120° is employed.

Such a bite angle can be accomplished when in the above formula (2-1) or (2-2), Y is a methylene group having hydrogen or a $C_{1-15}$ hydrocarbon group. In the case of the formula (2-2), two Y may be the same or different.

Among a group of the above-mentioned transition metal catalyst components, the formula (2-1) represents a group of transition metal catalyst components in which Y is a methylene group which has bonds to A and B and which has, as substituents, hydrogen or a $C_{1-5}$ hydrocarbon group.

In the case of the formula (2-2), the following compounds may be mentioned as examples of such a transition metal catalyst component:

(1,2'-methylene)(2,1'-methylene)bis(4,5-benz-1-indenyl) zirconium dichloride, (1,2'-isopropylidene)(2,1'-isopropylidene)bis(4,5-benz-1-indenyl) zirconium dichloride, (1,2-isopropylidene)(2,1'-methylene)bis(4,5-benz-1-indenyl)zirconium dichloride, (1,2'-methylene)(2,1'-methylene)(1-indenyl)(4,5-benz-1-indenyl)zirconium dichloride, (1,2'-isopropylidene)(2,1'-isopropylidene)(1-indenyl)(4,5-benz-1-indenyl)zirconium dichloride, (1,2-isopropylidene)(2,1'-methylene)(1-indenyl)(4,5-benz-1-indenyl)zirconium dichloride, (1,2'-methylene)(2,1'-methylene)(cyclopentadienyl)(4,5-benz-1-indenyl) zirconium dichloride, (1,2'-isopropylidene)(2,1'-isopropylidene)(cyclopentadienyl)(4,5-benz-1-indenyl) zirconium dichloride, (1,2'-isopropylidene)(2,1'-methylene) (cyclopentadienyl)(4,5-benz-1-indenyl)zirconium dichloride, (1,2'-methylene)(2,1'-methylene)bis(3-cyclopenta(c)phenanthryl)zirconium dichloride, (1,2'-isopropylidene)(2,1-isopropylidene)bis(3-cyclopenta(c) phenanthryl)zirconium dichloride, (1,2'-isopropylidene)(2, 1'-methylene)bis(3-cyclopenta(c)phenanthryl)zirconium dichloride, (1,2'-methylene)(2,1'-methylene)bis(1-cyclopenta(1)phenanthryl)zirconium dichloride, (1,2-isopropylidene)(1,2'-isopropylidene)bis(1-cyclopenta(1) phenanthryl)zirconium dichloride, and (1,2'-isopropylidene) (2,1'-methylene)bis(1-cyclopenta(1)phenanthryl)zirconium dichloride.

In the foregoing, zirconium complexes were exemplified, but corresponding titanium complexes and hafnium complexes may also suitably be used.

As such transition metal compound as catalyst components, racemic-form or pseudo racemic-form are preferably used. In such a case, D-isomers or L-isomers may be used. Further, a mixture of a racemic-form and a meso-form may also be used.

Thirdly, the present invention provides a polymerization catalyst for producing an aromatic vinyl compound polymer or an aromatic vinyl compound-olefin copolymer, which comprises such a transition metal compound and a cocatalyst and which provides a remarkably high productivity, and an efficient method for producing an aromatic vinyl compound polymer and an aromatic vinyl compound-olefin copolymer, employing such a catalyst.

Particularly, it provides a polymerization catalyst for producing an aromatic vinyl compound polymer having isotactic stereoregularity in the polymer structure or an aromatic vinyl compound-olefin copolymer having an isotactic structure, and a method for producing an isotactic aromatic vinyl compound polymer and an aromatic vinyl compound-olefin copolymer having an isotactic structure, employing such a catalyst.

As the cocatalyst to be used in the present invention, a cocatalyst which has been used in combination with a transition metal compound as catalyst component, can be used. As such a cocatalyst, aluminoxane (or alumoxane), or a boron compound, is preferably employed.

Further, the present invention provides a method for producing an aromatic vinyl compound polymer or an aromatic vinyl compound-olefin copolymer wherein the cocatalyst to be used is an aluminoxane (or alumoxane) of the following formula (3) or (4):

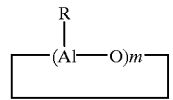

(3)

wherein R is a $C_{1-5}$ alkyl group, a $C_{6-10}$ aryl group or hydrogen, m is an integer of from 2 to 100, and the plurality of R may be the same or different,

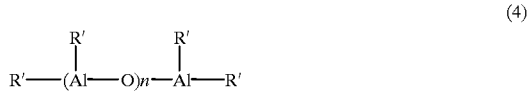

(4)

wherein R' is a $C_{1-5}$ alkyl group, a $C_{6-10}$ aryl group or hydrogen, n is an integer of from 2 to 100, and the plurality of R' may be the same or different.

As the aluminoxane, methylalumoxane, ethylalumoxane or triisobutylalumoxane, is preferably employed. Particularly preferred is methylalumoxane. If necessary, a mixture of these different types of alumoxanes, may be employed. Further, such an alumoxane may be used in combination with an alkylaluminum such as trimethylaluminum, triethylaluminum or triisobutylaluminum, or with a halogen-containing alkylaluminum such as dimethylaluminum chloride.

Addition of an alkylaluminum to the catalyst is effective for removing substances which hinder polymerization, such as a polymerization inhibitor in styrene, or moisture in the solvent, or for removing adverse effects against the polymerization reaction.

However, it is not necessarily required to add an alkylaluminum, if the amount of styrene, solvent, etc. is preliminarily reduced to a level not to influence the polymerization, by a known method such as distillation, bubbling with a dry inert gas or passing through a molecular sieve, or by increasing the amount of alumoxane to some extent or adding alumoxane in divided portions.

In the present invention, a boron compound may be used as a cocatalyst together with the above transition metal compound as catalyst component.

The boron compound to be used as a cocatalyst may, for example, be triphenylcarbeniumtetrakis(pentafluorophenyl) borate {trityltetrakis(pentafluorophenyl)borate}, lithium tetra(pentafluorophenyl)borate, tri(pentafluorophenyl) boran, trimethylammoniumtetraphenyl borate, triethylammoniumtetraphenyl borate, tripropylammoniumtetraphenyl borate, tri(n-butyl) ammoniumtetraphenyl borate, tri (n-butyl)ammoniumtetra(p-tolyl)phenyl borate, tri(n-butyl) ammoniumtetra(p-ethylphenyl)borate, tri(n-butyl) ammoniumtetra(pentafluorophenyl)borate, trimethylammoniumtetra (p-tolyl) borate, trimethylammoniumtetrakis-3,5-tetramethylphenyl borate, triethylammoniumtetrakis-3,5-dimethylphenyl borate, tributylammoniumtetrakis-3,5-dimethylphenyl borate, tributylammoniumtetrakis-2,4-dimethylphenyl borate, aniliumtetrakispentafluorophenyl borate, N,N'-dimethylaniliuntetraphenyl borate, N,N'-dimethylaniliumtetrakis(p-tolyl)borate, N,N'-dimethylaniliumtetrakis(m-tolyl)borate, N,N'-dimethylaniliumtetrakis(2,4-dimethylphenyl)borate, N,N'-dimethylaniliumtetrakis(3,5-dimethylphenyl)borate, N,N'-dimethylaniliumtetrakis(pentafluorophenyl)borate, N,N'-diethylaniliumtetrakis(pentafluorophenyl)borate, N,N'-2,4, 5-pentamethylaniliumtetraphenyl borate, N,N'-2,4,5-pentaethylaniliumtetrraphenyl borate, di-(isopropyl)

ammoniumtetrakispentafluorophenyl borate, di-cyclohexylammoniumtetraphenyl borate, triphenylphosphoniumtetraphenyl borate, tri(methylphenyl)phosphoniurtetraphenyl borate, tri(dimethylphenyl)phosphoniumtetraphenyl borate, triphenylcarbeniumtetrakis (p-tolyl) borate, triphenylcarbeniumtetrakis(m-tolyl)borate, triphenylcarbeniumtetrakis(2,4-dimethylphenyl)borate, triphenylcarbeniumtetrakis(3,5-dimethylphenyl)borate, tropiliumtetrakispentafluorophenyl borate, tropiliumtetrakis(p-tolyl)borate, tropiliumtetrakis(m-tolyl)borate, tropiliumtetrakis(2,4-dimetyylphenyl)borate or tropiliuntetrakis(3,5-dimethylphenyl)borate.

Such a boron compound and the above-mentioned organoaluminum compound may be used at the same time.

Especially when a boron compound is used as a cocatalyst, addition of an alkylaluminum compound such as triisobutylaluminum is effective for the removal of impurities which adversely affect the polymerization, such as water contained in the polymerization system.

Aromatic vinyl compounds to be used in the present invention may, for example, be styrene and various substituted styrenes such as p-methylstyrene, m-methylstyrene, o-methylstyrene, o-t-butylstyrene, p-t-butylstyrene, p-chlorostyrene, o-chlorostyrene, and α-methylstyrene. Further, a compound having a plurality of vinyl groups in one molecule, such as divinylbenzene, may also be mentioned.

Industrially preferably, styrene, p-methylstyrene or p-chlorostyrene is used. Particularly preferably, styrene is used.

Further, as olefins to be used in the present invention, $C_{2-20}$ α-olefins such as ethylene, propylene, 1-butene, 1-hexene, 1-methyl-1-pentene, 1-octene and cyclic olefins such as cyclopentene, norbornene and norbonadiene, may be mentioned. These olef ins may be used alone or in combination as a mixture of two or more of them. As such olefins, ethylene and propylene are preferred. In the following description, examples in which ethylene and propylene are used as olefins, will be referred to.

For the production of a polymer or a copolymer of the present invention, the olefin, the above exemplified aromatic vinyl compound, the transition metal compound as catalyst component as a metal complex and the cocatalyst are contacted. As to the manner and order for contacting, an optional known method may be employed.

For the production of an aromatic vinyl compound polymer of the present invention, the above exemplified aromatic vinyl compound, the transition metal compound as catalyst component as a metal complex and the cocatalyst are contacted. As to the manner and order for contacting, an optional known method may be employed.

As a method for the above polymerization or copolymerization, it is possible to employ a method for carrying out the polymerization in a liquid monomer without using any solvent, or a method of using a single solvent or a mixed solvent selected from saturated aliphatic or aromatic hydrocarbons or halogenated hydrocarbons, such as pentane, hexane, heptane, cyclohexane, benzene, toluene, ethylbenzene, xylene, chlorobenzene, chlorotoluene, methylene chloride or chloroform. If necessary, batch polymerization, continuous polymerization, stepwise polymerization, slurry polymerization, preliminary polymerization or gas phase polymerization may be employed.

Heretofore, when styrene is employed as a monomer component, it used to be impossible to employ gas phase polymerization in view of its low vapor pressure. However, when a catalyst of the present invention comprising a transition metal compound as catalyst component for polymerization and a cocatalyst, is employed, the copolymerization ability of styrene will be remarkably high, whereby copolymerization is possible even at a low styrene monomer concentration. Namely, copolymerization of an olefin with styrene is possible even under a low styrene partial pressure under a gas phase polymerization condition. In such a case, the transition metal catalyst component for polymerization and the cocatalyst may be used as supported on a suitable known carrier.

The polymerization or copolymerization temperature is suitably from −78° C. to 200° C. A polymerization temperature lower than −78° C. is industrially disadvantageous, and if the temperature exceeds 200° C., decomposition of the metal complex is likely to take place, such being undesirable. Industrially more preferably, the temperature is from −20 to 160° C., particularly from 30 to 160° C.

The pressure for copolymerization is suitably from 0.1 to 200 atm, preferably from 1 to 50 atm, industrially particularly preferably, from 1 to 30 atm.

When an organoaluminum compound is used as a cocatalyst, it is preferably used in an aluminum atom/complex metal atom ratio of from 0.1 to 100,000, preferably from 10 to 10,000, relative to the metal of the complex. If the ratio is smaller than 0.1, the metal complex can not effectively be activated, and if it exceeds 100,000, such will be economically disadvantageous.

When a boron compound is used as a cocatalyst, it is used in an atomic ratio of boron atom/complex metal atom of from 0.01 to 100, preferably from 0.1 to 10, particularly preferably 1. If the atomic ratio is less than 0.01, the metal complex can not effectively be activated, and if it exceeds 100, such is economically disadvantageous.

The metal complex and the cocatalyst may be repared by mixing them outside the polymerization tank, or they may be mixed in the tank during polymerization.

Fourthly, the present invention provides an aromatic vinyl compound-olefin copolymer obtained by using the transition metal compound as catalyst component of the present invention or by the method of the present invention.

Further, it provides an aromatic vinyl compound-ethylene random copolymer having a head-to-tail chain structure of at least two aromatic vinyl compound units, wherein the aromatic vinyl compound content is from 5 to 99.9 mol %. This copolymer is a novel copolymer and includes an aromatic vinyl compound-ethylene random copolymer obtained by using the transition metal compound as catalyst component of the present invention or by the method of the present invention. However, it is not particularly limited by the transition metal catalyst component or the method of the present invention.

In the following, reference is made to a styrene-ethylene random copolymer as an example of the aromatic vinyl compound-ethylene random copolymer of the present invention. However, the present invention is by no means restricted to such a styrene-ethylene copolymer.

The structure is determined by a nuclear magnetic resonance method (NMR).

The copolymer of the present invention has main peaks at the following positions in 13C-NMR using TMS as standard.

Namely, it shows peaks attributable to the main chain methylene and the main chain methine carbon in the vicinity of from 24 to 25 ppm, 27 ppm, 30 ppm, from 34 to 37 ppm, from 40 to 41 ppm and from 42 to 46 ppm, peaks attributable to five atoms not bonded to the polymer chain among phenyl groups in the vicinity of 126 ppm and 128 ppm, and a peak attributable to one carbon bonded to the polymer main chain among phenyl groups in the vicinity of 146 ppm.

The styrene-ethylene random copolymer of the present invention is a styrene-ethylene random copolymer having a styrene content of at least 5 and less than 99.9%, more preferably at least 10 and less than 99.9%, by molar traction, and the stereoregularity of phenyl groups in the alternating structure of styrene and ethylene of the following formula (5) contained in its structure is represented by an isotactic diad index m of larger than 0.75, and the alternating structure index λ of the following formula (i) is smaller than 70 and larger than 1, preferably smaller than 70 and larger than 5:

$$\lambda = A3/A2 \times 100 \quad (i)$$

Here, A3 is the sum of areas of three peaks a, b and c attributable to the carbons in styrene-ethylene alternating structure of the following formula (5'). Further, A2 is the sum of areas of peaks attributable to the main chain methylene and the main chain methine carbon, as observed within a range of from 0 to 50 ppm by 13C-NMR using TMS as standard:

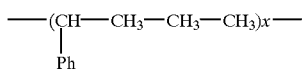
(5)

wherein Ph is an aromatic group such as a phenyl group, and x is an integer of at least 2, representing the number of repeating units,

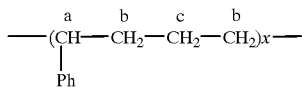
(5')

wherein Ph is an aromatic group such as a phenyl group, and x is an integer of at least 2, representing the number of repeating units.

In the styrene-ethylene random copolymer of the present invention, the stereoregularity of phenyl groups in the alternating copolymer structure of ethylene and styrene being an isotactic structure is meant for a structure wherein the isotactic diad index m (or a meso diad fraction) is more than 0.75, preferably more than 0.85, more preferably more than 0.95.

The isotactic diad index m of the alternating copolymer structure of ethylene and styrene can be obtained by the following formula (ii) from an area Ar of the peak attributable to the r structure and an area Am of the peak attributable to the m structure appearing in the vicinity of 25 ppm.

$$m = Am/(Ar+Am) \quad (ii)$$

The positions of the peaks may sometimes shift more or less depending upon the measuring conditions or the solvent used.

For example, when chloroform-d is used as a solvent, and TMS is used as standard, the peak attributable to the r structure appears in the vicinity of from 25.4 to 25.5 ppm, and the peak attributable to the m structure appears in the vicinity of from 25.2 to 25.3 ppm.

Further, when 1,1,2,2-tetrachloroethane-d2 is used as a solvent, and the center peak (shift value of 73.89 ppm from TMS standard) of the triplet of the 1,1,2,2-tetrachloroethane-d2 is used as standard, the peak attributable to the r structure appears in the vicinity of from 25.3 to 25.4 ppm, and the peak attributable to the m structure appears in the vicinity of from 25.1 to 25.2 ppm.

Here, the m structure represents a meso diad structure, and the r structure represents a racemic diad structure.

In the styrene-ethylene random copolymer of the present invention, a peak attributable to the r structure of the alternating structure of ethylene and styrene is not substantially observed.

The chain structure of a head-to-tail bond of styrene units contained in the styrene-ethylene random copolymer of the present invention is a chain structure of at least two styrenes, preferably a chain structure of at least three styrenes, which can be represented by the following structure:

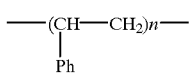

wherein n is an optional integer of at least 2, and Ph is aromatic group such as phenyl group.

The chain structure wherein two styrene units are bonded head-to-tail, gives peaks in the vicinity of from 42.4 to 43.0 ppm and from 43.7 to 44.5 ppm in the 13C-NMR measurement using TMS as standard and 1,1,2,2-tetrachloroethane-d2 as a solvent.

The chain structure in which at least three styrene units are bonded head-to-tail gives peaks also in the vicinity of from 40.7 to 41.0 ppm and front 43.0 to 43.6 ppm in a similar measurement. Accordingly, the chain structure in which at least two styrene units bonded head-to-tail gives a peak in the vicinity of from 40 to 45 ppm in a similar measurement.

On the other hand, in the conventional so-called pseudo random copolymer, no head-to-tail chain structure of styrene can be found even in the vicinity of 50 mol % at which the styrene content is maximum. Further, even if homopolymerization of styrene is attempted by using a catalyst for the preparation of a pseudo random copolymer, no polymer is obtainable. Depending upon e.g. the polymerization condition, an extremely small amount of an atarctic styrene homopolymer may sometimes be obtained. However, this is considered to have been formed by radical polymerization or cation polymerization by coexisting methylalumoxane or an alkylaluminum included therein.

Further, in the styrene-ethylene random copolymer of the present invention, the stereoregularity of phenyl groups in the head to tail chain structure of styrene units is isotactic.

The stereoregularity of phenyl groups in the head to tail chain structure of styrene units being isotactic, is meant for a structure wherein the isotactic diad index 20 ms (or a mesa diad fraction) is larger than 0.5, preferably at least 0.7, more preferably at least 0.8.

The stereoregularity of the chain structure of styrene units is determined by the peak position of methylene carbon in the vicinity of from 43 to 44 ppm as observed by 13C-NMR and by the peak position of the main chain proton as observed by 1H-HNR.

According to U.S. Pat. No. 5,502,133, methylene carbon of an isotactic polystyrene chain structure appears in the vicinity of from 42.9 to 43.3 ppm, but methylene carbon of a syndiotactic polystyrene chain structure appears in the vicinity of from 44.0 to 44.7 ppm. The positions of the sharp peak of methylene carbon of the syndiotactic polystyrene and the broad peak at from 43 to 45 ppm of an atarctic polystyrene are close to or overlap the positions of peaks with relatively low intensity of other carbon of the styrene-ethylene random copolymer of the present invention. However, in the present invention, a strong methylene carbon peak is observed from 42.9 to 43.4 ppm, but no clear peak is observed in the vicinity of from 44.0 to 44.7.

Further, according to U.S. Pat. No. 5,502,133 and the Comparative Examples of the present invention, the peaks attributable to the main chain methylene and methine proton in 1H-NMR, are observed at from 1.5 to 1.6 ppm and from 2.2 to 2.3 ppm in the case of an isotactic polystyrene and at from 1.3 to 1.4 ppm and from 1.8 to 1.9 ppm in the case of a syndiotactic polystyrene.

With the copolymer of the present invention, peaks are observed at from 1.5 to 1.6 ppm and at 2.2 ppm, and the result of this NMR analysis indicates that the styrene chain in the copolymer of the present invention has isotactic stereoregularity.

The isotactic diad index ms of the chain structure of styrene units can be obtained by the following formula from the respective peaks of methylene carbon in the styrene chain structure by the 13C-NMR measurement or the main chain methylene and methine proton by the 1H-NMR measurement.

Namely, it can be obtained by the following formula (iii) from an area Ar' of the peak attributable to the syndiotactic diad structure (r structure) of each peak and an area Am' of the peak attributable to the isotactic diad structure (m structure).

$$ms = Am'/(Ar'+Am') \qquad (iii)$$

The positions of the peaks may sometimes shift more or less depending upon the measuring conditions or the solvent used.

The random copolymer in the present invention is a copolymer containing a chain structure wherein styrene units are bonded head-to-tail, a chain structure wherein ethylene units are bonded to one another and a structure in which styrene units and ethylene units are bonded. The proportions of these structures contained in the copolymer vary depending upon the content of styrene or polymerization conditions such as the polymerization temperature.

As the styrene content decreases, the proportion of the chain structure in which styrene units are bonded head-to-tail, decreases. For example, in a case of a copolymer wherein the styrene content is not higher than about 20 mol %, it is difficult to directly observe a peak attributable to the chain structure wherein styrene units are bonded head-to-tail, by the usual 13C-NMR measurement. However, it is evident that the chain structure in which styrene units are bonded head-to-tail, is present in the copolymer, although the amount may be small, even if the styrene content is not higher than 20 mol %, since it is possible to produce a homopolymer having stereoregularity under high catalytic activity by homopolymerization of styrene by using the transition metal catalyst component of the present invention or by the method of the present invention, i.e. it is essentially possible to form a chain structure in which styrene units are bonded head-to-tail, and since in the copolymer, the proportion of the chain structure in which styrene units are bonded head-to-tail, continuously changes corresponding to the styrene content of from 20 to 99 mol % at least by the 13C-NMR method. It is possible to observe the chain structure wherein styrene units are bonded head-to-tail, in the copolymer having a styrene content of not higher than 20 mol %, by such a means as the 13C-NMR analysis using a styrene monomer enriched with 13C.

The same applies to the chain structure of ethylene units.

It is known that peaks of methylene carbon of the structure derived from inversion of styrene in a conventional pseudo random copolymer having no stereoregularity, are present in two regions of from 34.0 to 34.5 ppm and from 34.5 to 35.2 ppm (for example, Polymer Preprints, Japan, 42, 2292 (1993)).

With the styrene-ethylene random copolymer of the present invention, a peak attributable to methylene carbon of an inversion bond structure derived from styrene is observed in a region of from 34.5 to 35.2 ppm, but no substantial peak is observed at from 34.0 to 34.5 ppm.

This indicates one of the characteristics of the copolymer of the present invention and indicates that high stereoregularity of phenyl groups is maintained even with an inversion bond structure of the following formula derived from styrene.

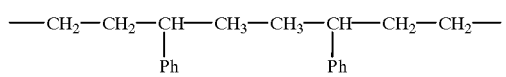

The weight average molecular weight of the styrene-ethylene random copolymer of the present invention is at least 60,000, preferably at least 80,000, particularly preferably at least 180,000, when the styrene content is at least 5 mol % and less than 20 mol %, and at least 30,000, preferably at least 40,000, more preferably at least 100,000, particularly preferably at least 220,000, when the styrene content is at least 20 mol % and less than 55 mol %, and at least 30,000, preferably at least 40,000, when the styrene content is at least 55 mol % and at most 99.9 mol %, thus being a practical high molecular weight. The molecular weight distribution (Mw/Mn) is at most 6, preferably at most 4, particularly preferably at most 3.

Here, the weight average molecular weight is a molecular weight as calculated as polystyrene, obtained by GPC using standard polystyrene. The same applies in the following description.

The styrene-ethylene random copolymer of the present invention is characterized in that it has a highly stereoregular alternating structure of ethylene and styrene in combination with various structures such as ethylene chains having various lengths, inversion of styrene and head to tail chains of styrene having various length. Further, with the styrene-ethylene random copolymer of the present invention, the proportion of the alternating structure can be variously changed by the styrene content in the copolymer within a range of λ of the above formula being more than 1 and less than 70. The stereoregular alternating structure is a crystallizable structure. Accordingly, the copolymer of the present invention can be made to have various properties in the form of a polymer having a crystalline, non-crystalline, or partially or microcrystalline structure, by controlling the St content or the crystallinity by a suitable method. The value λ being less than 70 is important in order to impart significant toughness and transparency to a crystalline polymer, or to obtain a partially crystalline polymer, or to obtain a non-crystalline polymer.

As compared with a conventional styrene-ethylene copolymer having no stereoregularity or no styrene chains, the copolymer of the present invention is improved in various properties such as the initial tensile modulus, hardness, breaking strength and solvent resistance in various St content regions at various degrees of crystallinity and thus exhibits characteristic physical properties as a novel crystalline resin, a thermoplastic elastomer or a transparent soft resin.

Further, by changing the styrene content, the glass transition point can be changed within a wide range from −50° C. to 100° C.

Among copolymers of the present invention, a copolymer consisting mainly of a chain structure of styrene units and an alternating structure of styrene units and ethylene units and having a styrene content of more than 50 mol %, has high transparency and a high glass transition temperature and exhibits a high initial tensile modulus and excellent physical properties as a plastic, since ethylene chains are little or very little. Further, the alternating structure and a small amount of ethylene chains are relatively uniformly present in the chain structure, whereby the copolymer is excellent in impact resistance and shows excellent toughness. Within a styrene content from 10 mol % to 75 mol %, preferably from 15 mol % to 60 mol %, the copolymer has crystallizability due to the stereoregularity of the alternating structure and will be a copolymer having a partially or microcrystalline structure, whereby it is capable of exhibiting physical properties as a thermoplastic elastomer in the vicinity of the glass transition temperature or at a higher temperature.

Further, the styrene chain structure has an isotactic stereoregularity, whereby the copolymer is crystallizable, and can be crystallized by a common crystallization treatment.

The styrene-ethylene random copolymer of the present invention can have a melting point of from about 50 to 130° C. (by DSC) within a range of a styrene content of from 10 to 75 mol %. Further, at a styrene content of at least 90 mol %, it may have a melting point of from about 100 to 240° C. attributable to an isotactic polystyrene chain structure. The heat of crystal fusion is at a level of from 1 to 50 J/g in either case. Such heat of crystal fusion and melting point by DSC can be changed to some extent by e.g. pretreatment conditions.

On the other hand, a conventional styrene-ethylene copolymer (a pseudo random copolymer) having no stereoregularity or no styrene chain, has a crystal structure similar to polyethylene at a low styrene content, as shown in literature ANTEC, 1634 (1996), but with an increase of the styrene content in the copolymer, the melting point and the crystallinity will rapidly decrease, and at a styrene content of about 15 mol %, the melting point becomes as low as about room temperature. Further, at a styrene content of from about 15 or 20 mol % to less than 50 mol %, the copolymer will be amorphous having no melting point.

The styrene-ethylene random copolymer of the present invention which contains basically no dissolvable plasticizer or halogen, has a basic characteristic that it is highly safe.

Further, depending upon the polymerization conditions, etc., a small amount of an atarctic homopolymer formed by polymerization of an aromatic vinyl compound by heat, radical or cation polymerization, may sometimes be contained, but such an amount should be less than 10 wt % of the total. Such a homopolymer can be removed by extraction with a solvent, but the copolymer may be used as it contains such a homopolymer, provided that there will be no particular problem from the viewpoint of the physical properties.

The copolymer of the present invention has the following characteristics at the respective styrene contents.

The copolymer with a styrene content of from 5 to 10 mol % has high tensile strength and transparency, is flexible and shows a nature as a platomer or elastomer.

The copolymer with a styrene content of from 10 to 25 mol % has high tensile strength, elongation, transparency, flexibility and resiliency and shows a nature as an elastomer.

The copolymers having the foregoing compositions are useful alone or in the form of an alloy of the copolymers having different styrene contents or in the form of an alloy with a polyolefin such as polypropylene, as a stretch film for packaging.

The copolymer with a styrene content of from 50 to 99.9 mol % having a microcrystalline structure or a low crystallinity, is a plastic having high transparency and has a high shrinking property at a temperature of at least the glass transition point and high dimensional stability at a temperature of not higher than the glass transition temperature, and thus it is useful as a shrinkable film for packaging.

Further, even if a fixed shape formed by once heating at a temperature higher than the melting point and then quenching to a temperature below the glass transition temperature, is deformed under a temperature condition of higher than the glass transition temperature and lower than the melting point and cooled to a temperature lower than the glass transition temperature to fix the deformed shape, if it is heated again to a temperature higher than the glass transition temperature and lower than the melting point, it recovers the initial shape, Namely, the copolymer has a shape memory property.

The copolymer with a styrene content of from 5 to 50 mol % is suitably employed for various applications as a substitute for soft polyvinyl chloride, in the form of an alloy with a polyolefin such as polypropylene or polyethylene, or with polystyrene or other resin, or in the form of a partially crosslinked composition. Further, the copolymer with this composition is useful as a compatibilizing agent for a polyolefin and a styrene resin, as an additive to a styrene resin or a polyolefin resin, as a modifier for rubber, as a component for an adhesive, or as bitumen (an additive to asphalt).

By changing the styrene content, the glass transition point of the copolymer of the present invention can be optionally changed within a range of from −50 to 100° C., and the copolymer has a large tans peak in the viscoelasticity spectrum and thus is useful as a vibration preventing material effective for a wide temperature range.

With the copolymer having a styrene content of about 50 mol %, it is relatively easy to increase the crystallinity as compared with copolymers with other ranges of the styrene content, and it exhibits a high initial elastic modulus although it is opaque, and thus is useful as a novel partially crystalline plastic.

As a means for increasing the crystallinity, it is possible to adopt a means such as annealing, addition of nucleating agent or alloying with a polymer having low Tg (such as wax).

In the foregoing, a styrene-ethylene random copolymer has been described as a typical example of the aromatic vinyl compound-ethylene random copolymer of the present invention. However, the above description is generally applicable to the aromatic vinyl compound-ethylene random copolymer employing the above aromatic vinyl compound.

The present invention also provides an aromatic vinyl compound-propylene random copolymer wherein the aromatic vinyl compound content is from 5 to 99.9 mol %, This copolymer is a novel copolymer and includes an aromatic vinyl compound-propylene random copolymer obtained by using the transition metal compound as catalyst component of the present invention, or by the method of the present invention. However, such a copolymer is not restricted by the transition metal compound or the method of the present invention.

Now, a styrene-propylene random copolymer will be described as an example of the copolymer of the present invention.

The styrene-propylene random copolymer in the present invention is a copolymer having an aromatic vinyl compound content of from 5 to 99.9 mol %.

Further, it is an aromatic vinyl compound-propylene random copolymer characterized in that it has both chain structures of aromatic vinyl compound units and propylene units.

Further, it is an aromatic vinyl compound-propylene random copolymer, wherein the stereoregularity of the chain structures of the aromatic vinyl compound units and/or the propylene units, is isotactic.

The aromatic vinyl compound-olefin random copolymer of the present invention has a weight average molecular weight of at least 1,000, preferably at least 10,000, taking into consideration the physical properties as a copolymer (aromatic vinyl compound-ethylene random copolymer, is as described above). The molecular weight distribution (Mw/Mn) is at most 6, preferably at most 4, particularly preferably at most 3.

The aromatic vinyl compound-olefin random copolymer of the present invention is not necessarily required to be a pure copolymer, and other structures may be contained, or any other monomer among the above-mentioned α-olefins, aromatic vinyl compounds, and conjugated dienes such as butadiene, may be copolymerized, so long as the structure and the stereoregularity are within the above-mentioned ranges.

Further, depending upon the polymerization conditions, etc., a small amount of an atarctic homopolymer formed by polymerization of an aromatic vinyl compound by heat, radical or cation polymerization, may sometimes be contained, but such an amount should be less than 10 wt % of the total. Such a homopolymer can be removed by extraction with a solvent, but the copolymer may be used as it contains such a homopolymer, provided that there will be no particular problem from the viewpoint of the physical properties.

Further, for the purpose of improving the physical properties, it may be blended with other polymers. Further, copolymers of the present invention having different styrene contents may be blended.

Fifthly, the present invention provides a method for producing an aromatic vinyl compound polymer employing a transition metal compound of the above-mentioned formula (1) and cocatalyst.

The stereoregularity of the aromatic vinyl compound polymer obtained by the method of the present invention is represented by an isotactic pentad index (mmmm) of at least 0.70, preferably at least 0.80, more preferably at least 0.90. The isotactic diad index can be obtained from a peak attributable to carbon (PhCl) of a phenyl group bonded to the main chain of the polymer in the 13C-NMR measurement.

Namely, it is obtained from the proportion of the PhCl carbon peak area attributable to the mmmm structure in the total of PhCl carbon peak areas. The PhCl carbon peak attributable to the mmmm structure appears in the vicinity of 146.3 ppm when 1,1,2,2-tetrachloroethane-d2 is used as a solvent, and the triplet center peak (73.89 ppm) of 1,1,2,2-tetrachloroethane-d2 is used as standard.

The isotactic aromatic vinyl compound polymer obtained in the present invention has a weight average molecular weight of at least 1,000, preferably at least 10,000 taking into consideration the physical properties as a crystalline polymer. The molecular weight distribution (Mw/Mn) is at most 6, preferably at most 4, particularly preferably at most 3.

By the method of the present invention, it is possible to obtain an isotactic aromatic vinyl compound polymer having a high stereoregularity under high catalytic activities with little formation of atactic polystyrene as a byproduct.

Sixthly, the present invention provides an aromatic vinyl compound-olefin alternating copolymer, preferably an aromatic vinyl compound-ethylene alternating copolymer, consisting mainly of an alternating structure. This copolymer can be obtained by using the transition metal compound as catalyst component of the present invention, or by the method of the present invention.

The aromatic vinyl compound-ethylene alternating copolymer obtainable by the present invention, is an aromatic vinyl compound-ethylene alternating copolymer characterized in that the stereoregularity of phenyl groups in the alternating structure of ethylene and an aromatic vinyl compound, is represented by an isotactic diad index m which is at least 0.95, and the alternating structure index λ given by the above formula (i) is at least 70.

The isotactic diad (meso diad) index m of the alternating structure of ethylene and styrene in this copolymer, as an example of the aromatic vinyl compound-ethylene alternating copolymer of the present invention, can be obtained by the above-mentioned method employing the above formula (ii).

The weight average molecular weight obtained as calculated as standard polystyrene, of the aromatic vinyl compound-ethylene alternating copolymer of the present invention, is preferably at least 10,000, taking into consideration the physical properties as a crystalline plastic. The molecular weight distribution (Mw/Mn) is at most 6, preferably at most 4, particularly preferably at most 3.

This copolymer has an aromatic vinyl compound content of from 46 to 54 mol % and consists mainly of an alternating structure of ethylene and the aromatic vinyl compound, which has high stereoregularity. It is characterized in that it further contains small amounts of various structures, such as ethylene chains of various lengths, heterogeneous bonds of the aromatic vinyl compound and chains of the aromatic vinyl compound, in a proportion not higher than a certain level.

The copolymer of the present invention has a high proportion of the alternating structure and high stereoregularity due to the alternating structure and accordingly has characteristics such as high crystallinity, high melting point and a high crystallization speed.

The melting point of the copolymer obtainable by the DSC measurement is at least 130° C. and less than 210° C. preferably at least 150° C. and less than 210° C.

The copolymer of the present invention is capable of exhibiting high physical properties as a crystalline or partially crystalline polymer. Therefore, it is expected to open up a novel application of a crystalline plastic as a substitute for polypropylene, a PET resin, nylon, etc.

For the production of the alternating copolymer of the present invention, the polymerization temperature is usually from −20 to +40° C.

Seventhly, the present invention provides an aromatic vinyl compound-ethylene copolymer having the following features:

(1) an aromatic vinyl compound content is from 1 mol % to 99 mol %.
(2) an aromatic vinyl compound unit-ethylene unit alternating structure has a stereoregularity having an isotactic diad index of at least 0.75; and
(3) even after sufficiently subjecting to crystallization, a crystallinity derived from an aromatic vinyl compound-ethylene alternating structure is not observed.

The present invention further provides an aromatic vinyl compound-ethylene copolymer, characterized by having a head-to-tail chain structure of 2 or more aromatic vinyl compound units.

The present invention still further provides an aromatic vinyl compound-ethylene copolymer, wherein the aromatic vinyl compound content is from 15 mol % to 85 mol %, more preferably from 40 mol % to 85 mol %, most preferably from 50 mol % to 85 mol %, and a melting point is not observed between 70° C. to 200° C. by DSC measurement.

The present invention still further provides an aromatic vinyl compound-ethylene copolymer having an aromatic vinyl compound content of from 15 mol % to 85 mol %, preferably from 40 mol % to 85 mol %, wherein an alternating structure index λ calculated by the following formula (i') satisfies the following formula (ii');
Formula (i):

$$\lambda = A3/A2 \times 100$$

Formula (i$^A$):
in case of $15 \leq x < 50$ $1 \leq \lambda < x-10$
in case of $50 \leq x \leq 85$ $1 \leq \lambda < 90-x$
wherein x is an aromatic vinyl compound content (mol %), and in the formula (i), an A3 value is a total value of areas of three kinds of peaks a, b and c derived from an aromatic vinyl compound-ethylene alternating structure of the following formula (5') in accordance with 13C-NMR measurement, and an A2 value is a total value of peak areas derived from main chain methylene and main chain methine carbons observed in the range of from 0 to 50 ppm in accordance with 13C-NMR measurement based on TMS;

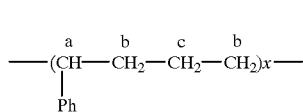

(5')

wherein Ph is an aromatic group, and x represents a number of repeating units and is an integer of at least 2.

The present invention still further provides an aromatic vinyl compound-ethylene copolymer, characterized by having peaks at 40–45 ppm, preferably at 40.4–41.0 ppm, 42.3–43.6 ppm, 43.0–43.6 ppm and 43.7–44.5 ppm, more preferably at 42.3–43.6 ppm and 43.7–44.5 ppm, observed by 13C-NMR measurement based on TMS.

The present invention still further provides an aromatic vinyl compound-ethylene copolymer, wherein the aroma tic vinyl compound unit having a head-to-tail chain structure is at least 0.1%, preferably at least 1.0% of the total amount of aromatic vinyl compound units contained in the copolymer and the aromatic vinyl compound content is at least 1 mol % and less than 30 mol %.

The present invention still further provides an aromatic vinyl compound-ethylene copolymer, characterized by having a weight average molecular weight of at least 10,000, preferably at least 30,000, most preferably at least 80,000, in terms of molecular weight of standard polystyrene calculation and a molecular weight distribution (Mw/Mn) of at most 6. Also, in view of processibility of polymer, the weight average molecular weight is at most 1,000,000, preferably at most 500,000.

The random copolymer of the present invention is a copolymer containing an aromatic vinyl compound unit chain structure having head-to-tail bonded, a chain structure having ethylene units bonded and a structure having an aromatic vinyl compound unit and an ethylene unit bonded. Depending on the styrene content or polymerization conditions such as polymerization temperature, the ratio of these structures contained in the copolymer varies. The ratio of these structures contained and the structure distribution are not restricted by structure distribution according to specific statistical calculation.

Hereinafter, the aromatic vinyl compound-ethylene copolymer of the present invention is explained by taking a styrene-ethylene copolymer as an example for instance, but the present invention is not limited thereto.

Its structure is determined in accordance with nuclear magnetic resonance method (NMR method). The copolymer of the present invention has main peaks at the following positions determined in accordance with 13C-NMR measurement based on TMS.

Peaks derived from main chain methylene and main chain methine carbons are present in the vicinity of 24–25 ppm, in the vicinity of 27 ppm, in the vicinity of 30 ppm, in the vicinity of 34–37 ppm, in the vicinity of 40–41 ppm and in the vicinity of 42–46 ppm, and peaks derived from 5 carbons not bonded to the polymer main chain among phenyl groups are present in the vicinity of 126 ppm and 128 ppm, and a peak derived from one carbon bonded to the polymer main chain among phenyl groups is present in the vicinity of 146 ppm.

The aromatic vinyl compound content is determined in accordance with 1H-NMR.

A head-to-tail bonded chain structure of styrene units contained in the styrene-ethylene copolymer of the present invention is a chain structure of two or more styrenes expressed by the following structure.

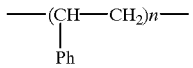

wherein n is an integer of at least 2, and Ph is a phenyl group.

A chain structure having two styrene units bonded by head-to-tail, has peaks in the vicinity of 42–43 ppm and 43–45 ppm, and preferably 42.3–43.6 ppm and 43.7–44.5 ppm, in accordance with 13C-NMR measurement based on TMS using tetrachloroethane-d as a solvent.

A chain structure having at least 3 styrene units bonded by head-to-tail has peaks in the vicinity of 40–41 ppm and 43–44 ppm, and preferably 40.4–41.0 ppm and 43.0–43.6 ppm, in accordance with the same measurement method.

Accordingly, a chain structure having at least 2 styrene units bonded by head-to-tail, has peaks in the vicinity of 40–45 ppm, preferably 40.4–41.0 ppm, 42.3–43.6 ppm, 43.0–43.6 ppm and 43.7–44.5 ppm.

On the other hand, a conventionally known pseudo random copolymer does not have a head-to-tail chain structure of styrene even when a styrene content reaches maximum and is in the vicinity of 50 mol %. Further, even when trying to homopolymerize styrene by using a catalyst for producing a pseudo random copolymer, a polymer can not be obtained. There is a case wherein quite a small amount of atactic styrene homopolymer can be obtained depending on polymerization conditions, but it should be understood that this is formed by radical polymerization or cation polymerization by methyl alumoxane or alkyl aluminum contained therein.

Such an atactic styrene homopolymer can be easily separated by solvent separation.

In the styrene-ethylene copolymer of the present invention, an isotactic structure having a stereoregularity of a phenyl group of ethylene and styrene alternating copolymer structure is a structure having an isotactic diad index m (or mesodiad index) of higher than 0.75, preferably at least 0.85, more preferably at least 0.95.

The isotactic diad index M of the ethylene-styrene alternating Polymerization structure c an be calculated from peak area Ar derived from r structure and peak area m derived from m structure of methylene carbon peak appearing in the vicinity of 25 ppm in accordance with the following formula (ii).

$$m = Am/(Ar+Am) \qquad (ii)$$

There is a case that peak positions are somewhat shifted depending on measurement conditions and a solvent used.

For example, in the case of using chloroform-d as a solvent and being based on TMS, the peak derived from r structure appears in the vicinity of 25.4–25.5 ppm and the peak derived from m structure appears in the vicinity of 25.2–25.3 ppm, Also, in the case of using tetrachloroethane-d as a solvent and being based on the central peak (73.89 ppm) of triplet of tetrachloroethane-d, the peak derived from r structure appears in the vicinity of 25.3–25.4 ppm and the peak derived from m structure appears in the vicinity of 25.1–25.2 ppm.

The m structure means meso-diad structure, and the r structure means racemi-diad structure.

In the styrene-ethylene copolymer of the present invention, peak attributable to the r structure is not substantially observed in ethylene-styrene alternating structure.

The copolymer of the present invention does not have a crystal structure based on ethylene-styrene alternating structure even after accelerating crystallization by a known method such as annealing, a nucleating agent, a crystallization assistant or the like. Particularly, a crystal diffraction peak attributed to ethylene-styrene alternating structure is not observed by X-ray diffraction method. The crystal diffraction peak based on ethylene-styrene alternating structure means a diffraction peak obtained by using a Cu ray source, which has an intensity at least 3 times higher than noise level in the range of from 15 to 40° of 2 θ, and is a diffraction peak having a peak area of at least 1% of halo peak area or a peak having a half band width of at most 3° of 2 θ. The X-ray diffraction peak derived from ethylene-styrene alternating structure is disclosed in JP-A-9-309925 and the literatures Macromol. Rapid Commun., vol.19, 327 (1998) and Macromol. Rapid Commun., vol.17, 745 (1996). The copolymer of the present invention may contain a crystal structure derived from polyethylene in a low aromatic vinyl compound content zone (about at most 15 mol %), and may also contain a crystal structure derived from isotactic polystyrene in a high aromatic vinyl compound content zone (about at least 90 mol %).

Further, the aromatic vinyl compound-ethylene copolymer of the present invention does not have a melting point between 70° C. and 200° C. according to DSC. measurement, and has an aromatic vinyl compound content of preferably from 15 mol % to 85 mol %, more preferably from 40 mol % to 85 mol %. The fact that a melting point is not observed between 70° C. and 200° C. in accordance with DSC measurement, means that there is no crystal structure (crystal structure derived from said styrene-ethylene alternating structure and crystal structure derived from polyethylene chain structure and polystyrene chain structure) having a melting point in this temperature range.

The copolymer of the present invention has a low alternating property and a high random property since the alternating structure index λ value satisfies the formula (i$^A$) in various styrene contents and is less than 40 even at the styrene content of 50 mol %.

Therefore, in the copolymer of the present invention, a crystal structure derived from isotactic styrene-ethylene alternating structure is not observed by X-ray diffraction method even after accelerating crystallization by a known method, Further, the copolymer of the present invention is characterized by having no melting point derived from any crystal structure between 70° C. and 200° C. in accordance with DSC measurement.

Still further, the copolymer of the present invention is characterized by having various structures therein, such as a chain structure of ethylene, a head-to-tail chain structure of styrene, a structure having a styrene unit and an ethylene unit bonded and the like, in any styrene content ranges. Even when the styrene content in the copolymer is from 50 mol % to 90 mol %, a chain structure of ethylene is observed in accordance with usual 13C-NMR measurement. The copolymer of the present invention having a high styrene content and also having an ethylene chain at random and uniformly in the main chain of the copolymer, is characterized by having non-crystallinity, high impact strength and high transparency.

When the styrene content in the copolymer is low and is from 1 mol % to 50 mol %, two or more head-to-tail styrene chain structures are observed by usual 13C-NMR measurement, The copolymer of the present invention having a head-to-tail styrene chain at random and uniformly in the main chain of copolymer having such a low styrene content, is characterized by destroying crystallinity of polyethylene chain and having high flexibility, high breaking strength and high transparency. In the present invention, an aromatic vinyl compound unit having a head-to-tail chain structure providing the above-mentioned peaks is at least 0.1%, preferably at least 1%, of the total amount of aromatic vinyl compound units contained in the copolymer when the aromatic vinyl compound content is at least 1 mol % and less than 30 mol %.

The amount of the aromatic vinyl compound unit having a head-to-tail chain structure contained in the copolymer is expressed by a ratio x to the total amount of aromatic vinyl compound units and is calculated by the following formula.

$$x = xa/xb \times 100 \qquad (iv)$$

wherein xa is a total value of peak areas derived from the main chain methine carbon of the head-to-tail chain structure of 2 or more aromatic vinyl compound units, for example, a total value of areas of peak (n) observed at 40.4–41.0 ppm and peak (j) observed at 42.3–43.6 ppm in accordance with 13C-NMR measurement based on TMS, and xb is a total value of peak areas derived from the main chain methine carbon of total aromatic vinyl compound units contained in the copolymer.

Eighthly, the present invention provides a transition metal compound of the following formula (1') as catalyst component:

wherein A' is an unsubstituted or substituted cyclopentaphenanthryl group of the following formula K-2' or K-3':

(K-2')

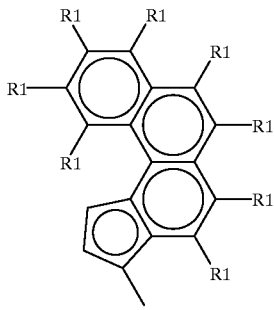

(K-3')

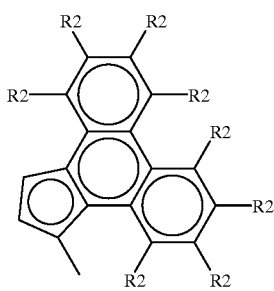

wherein in the above formulas K-2' and K-3', each of R1 and R2 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), provided that a plurality of R1 and a plurality of R2 may be the same or different, respectively, and each pair of adjacent R1 and adjacent R2 may together, with the atoms joining them, form a 5- to 8-member aromatic or aliphatic ring, B' is an unsubstituted or substituted cyclopentaphenanthryl group of the same chemical formula as A', an unsubstituted or substituted benzindenyl group of the following formula K-4', K-5' or K-6', or an unsubstituted or substituted cyclopentadienyl group, an unsubstituted or substituted indenyl group or an unsubstituted or substituted fluorenyl group, of the following formula K-7', K-8' or K-9':

(K-4')

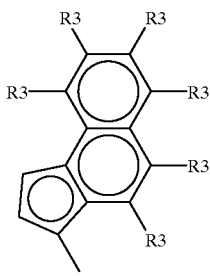

(K-5')

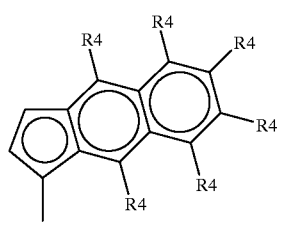

(K-6')

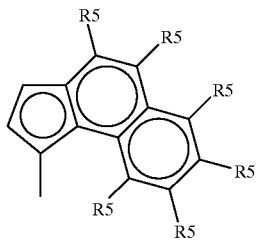

(K-7')

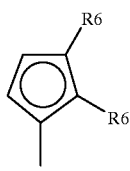

(K-8')

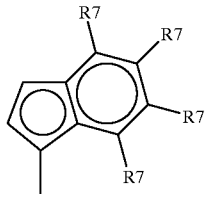

(K-9')

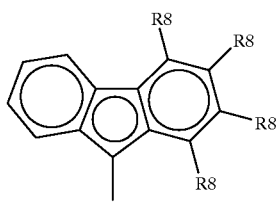

wherein in the above formulas K-4', K-5' and K-6' each of R3, R4 and R5 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), provided that a plurality of R3, a plurality of R4 and a plurality of R may be the same or different, respectively, and each pair of adjacent R3, adjacent R4 and adjacent R5 may together, with the atoms joining them, form a 5- to 8-member aromatic or aliphatic ring, except for forming an unsubstituted cyclopentaphenanthryrene group, wherein in the above formulas K-7', K-8' and K-9' each of R6, R7 and R8 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), provided that a plurality of R6, a plurality of R7 and a plurality of R8 may be the same or different, respectively, when both A' and B' are unsubstituted or substituted cyclopentaphenanthryl groups, they may be the same or different, Y' is a methylene group or a boron residue, which has bonds to A' and B' and which has, as substituents, hydrogen or a $C_{1-15}$ hydrocarbon group, wherein the substituents may be the same or different from each other, or Y' may have, together with the substituents, a cyclic structure including a cyclohexylidene group or a cyclopentylidene group, X is hydrogen, a halogen atom, a $C_1$–$C_{15}$ alkyl group, a $C_6$–$C_{10}$ aryl group, a $C_8$–$C_{12}$ alkylaryl group, a silyl group having a $C_1$–$C_4$ hydrocarbon substituent, $C_1$–$C_{10}$ alkoxy group or a dialkylamide group having a $C_1$–$C_6$ alkyl substituent, and M is zirconium, hafnium or titanium.

The polymerization catalyst comprising the transition metal component of the present invention and a cocatalyst can be suitably used for preparing an aromatic vinyl compound-olefin copolymer, preferably an aromatic vinyl compound-ethylene copolymer, and further can be used for polymerization or copolymerization of olefin. The term "olefin" used herein means as mentioned above, Preferable examples of olefin copolymerization include copolymerization of ethylene-propylene, ethylene-butene, ethylene-1-hexene, ethylene-1-octene, ethylene-norbornene, propylene-butene, propylene-1-hexene, and propylene-1-octene. The olefin copolymers thus obtained may further be copolymerized with dienes such as butadiene, isoprene, ethylene-ethylidenenorbornene and divinyl benzene. Examples of these copolymers include ethylene-propylene butadiene, ethylene-1-octene-butadiene, ethylene-propylene-ethylidene-norbornene and the like.

The polymerization catalyst comprising the transition metal catalyst component of the present invention and a cocatalyst achieves a very high catalyst activity when used for polymerization and copolymerization of olefin. That is, the catalyst produces at least 1,000 t of polymer per mol of the complex for 1 hour, and this is the highest level among conventionally known metallocene type catalysts. Further, the carbon-crosslinking complex (isopropylidene-crosslinking complex) of the present invention achieves a high activity particularly to an olefin having a hindering substituent. The term "hindering substituent" means a substituent having a carbon number of from 5 to 30. Examples of an olefin having such a hindering substituent include the above-mentioned styrene monomer as well as norbornene, ethylidene-norbornene, vinylcyclohexene, vinylcyclohexane, vinylnaphthalene and the like, Further, the catalyst of the present invention can be suitably used for copolymerization of these monomers with an olefin such as ethylene.

Also, when the polymerization catalyst comprising the transition metal catalyst component of the present invention and a cocatalyst, particularly the polymerization catalyst comprising the transition metal catalyst component in which B' is an unsubstituted or substituted cyclopentaphenanthryl group expressed by the same chemical formula as A', and a cocatalyst, is used for copolymerization of aromatic vinyl compound-ethylene, there is produced the aromatic vinyl compound-ethylene copolymer introduced as the seventh invention, having the following features:

(1) an aromatic vinyl compound content is from 1 mol % to 99 mol %.
(2) an aromatic vinyl compound-ethylene alternating structure has a stereoregularity having an isotactic diad index of at least 0.75; and
(3) even after sufficiently subjecting to crystallization, a crystallinity derived from an aromatic vinyl compound-ethylene alternating structure is not observed, and further there is produced the aromatic vinyl compound-ethylene copolymer, characterized by having a head-to-tail chain structure of 2 or more aromatic vinyl compound units.

Now, the present invention will be described in further detail with reference to Examples. However, it should be understood that the present invention is by no means restricted to such specific Examples.

In the following description, Cp represents a cyclopentadienyl group, Ind a 1-indenyl group, BInd a 4,5-benz-1-indenyl group, Flu a 9-fluorenyl group, Me a methyl group, Et an ethyl group, tBu a tertiary butyl group, and Ph a phenyl group.

Figure 6:
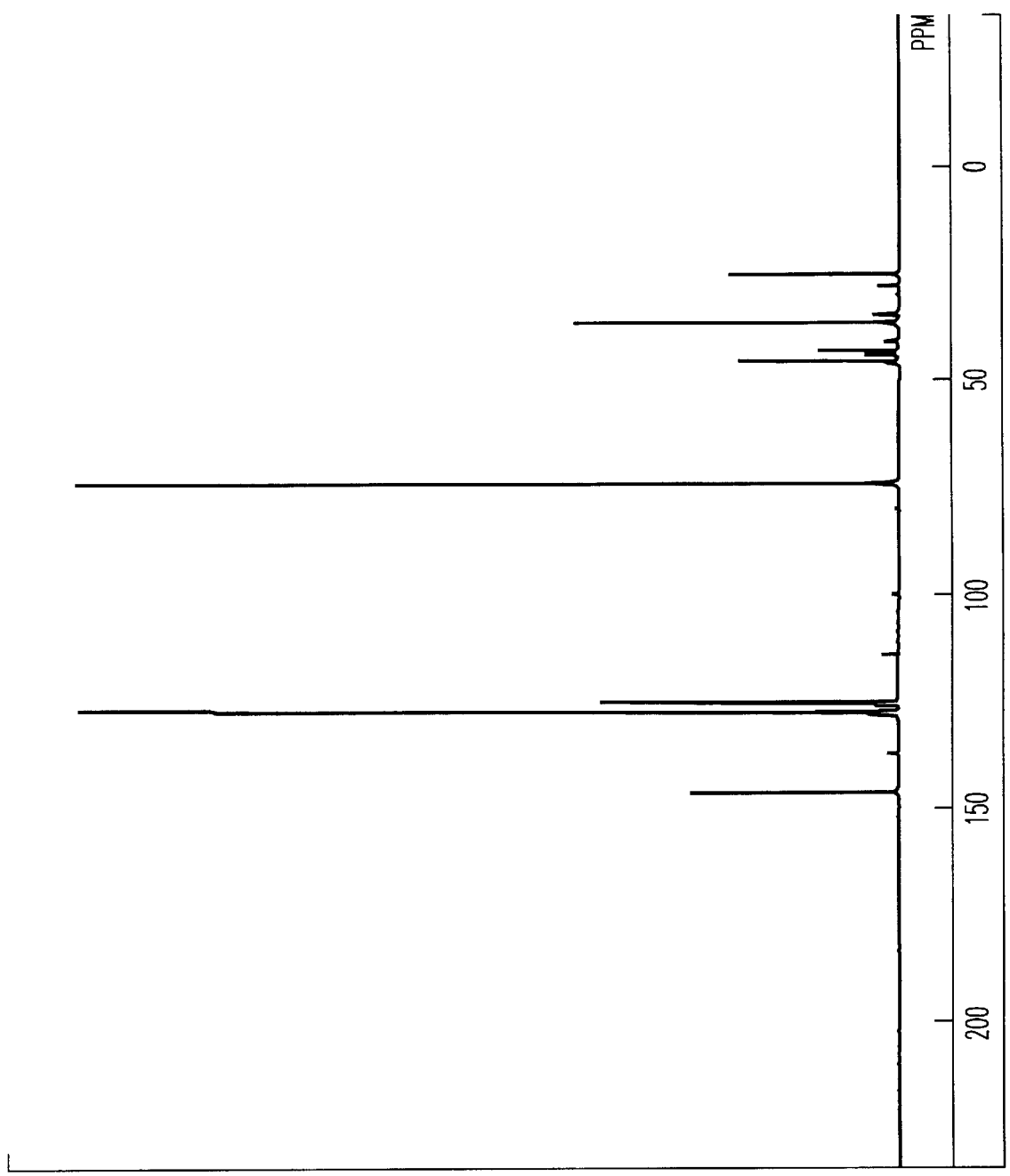
Figure 7:
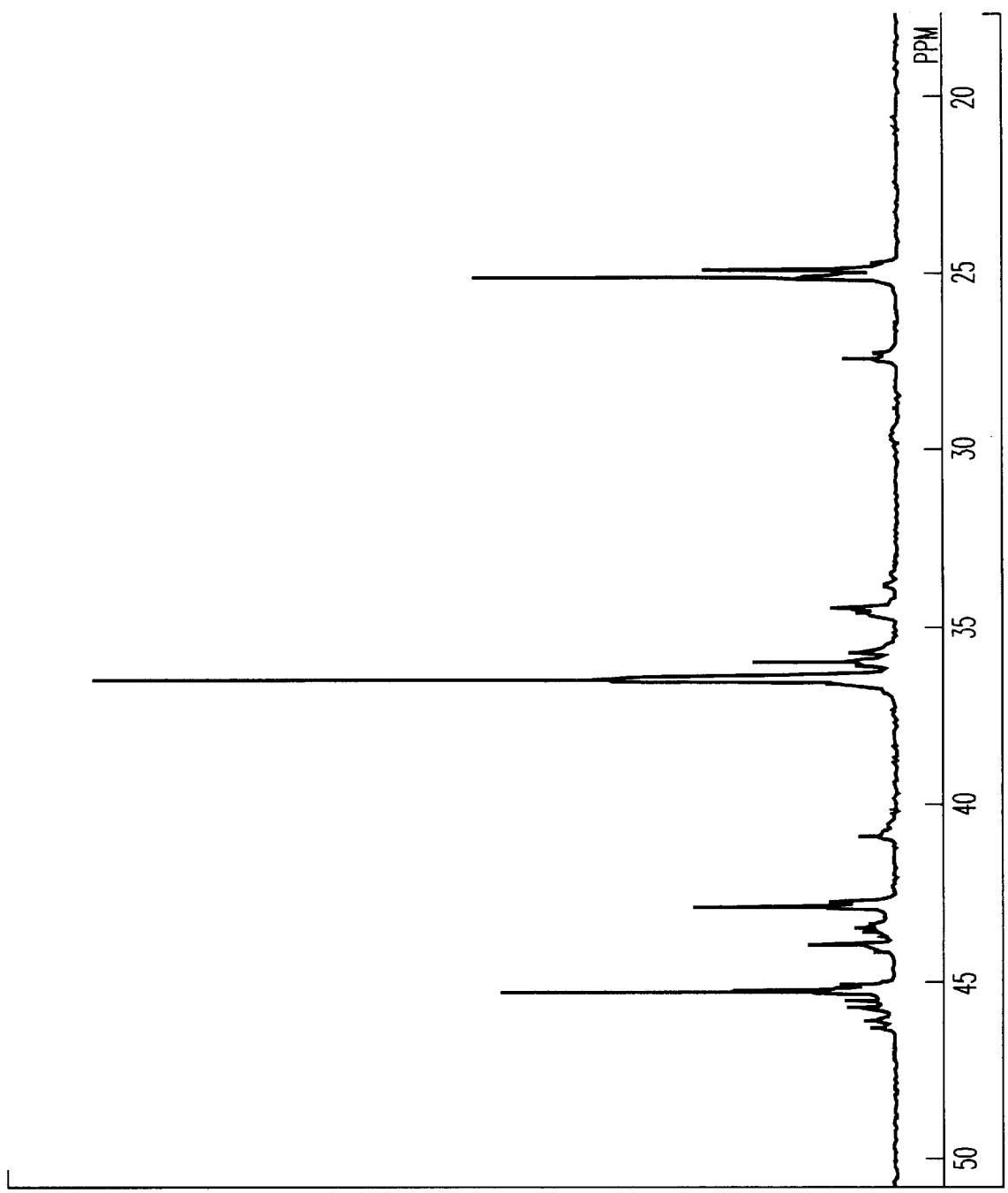
Figure 8:
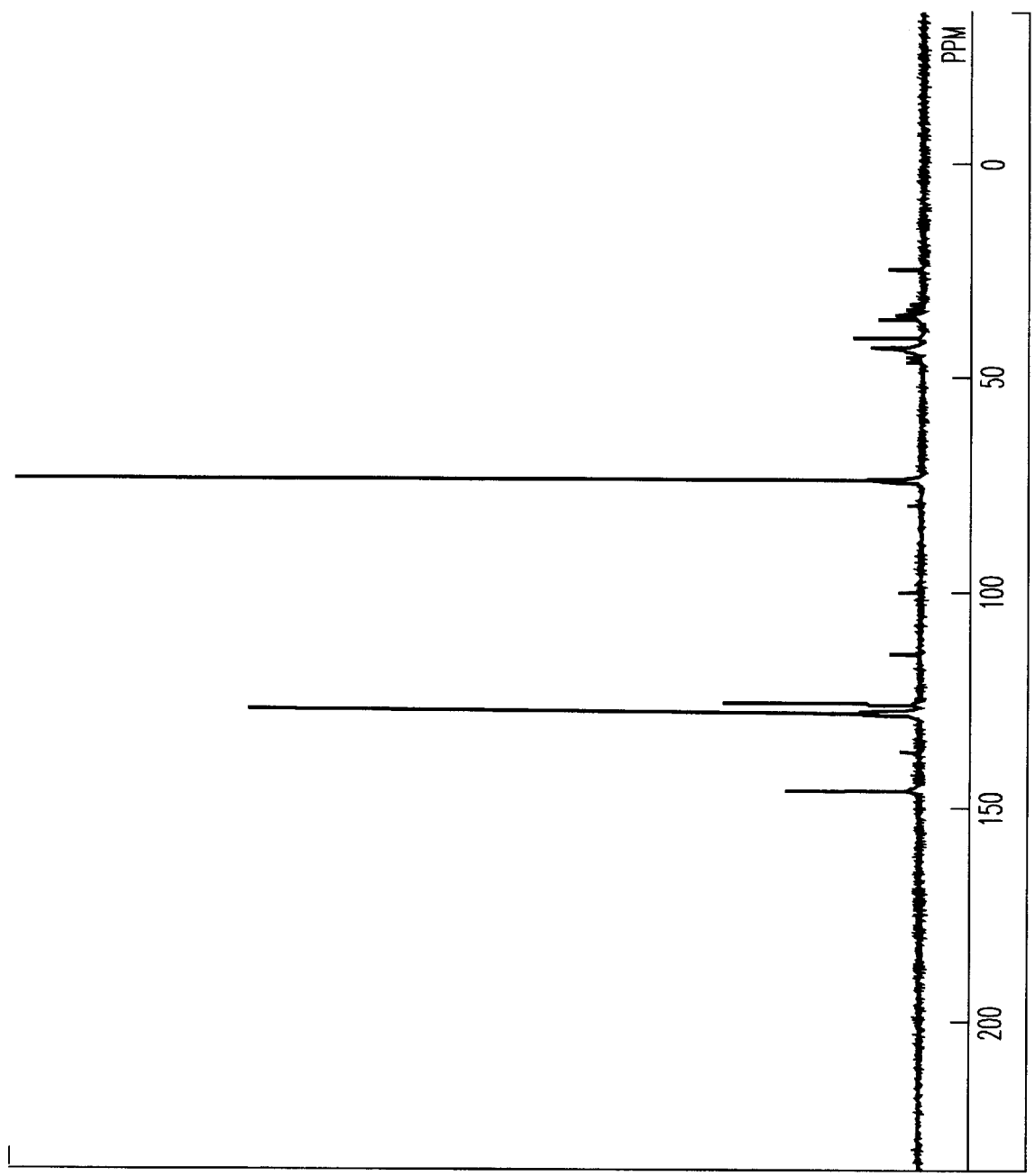
Figure 9:
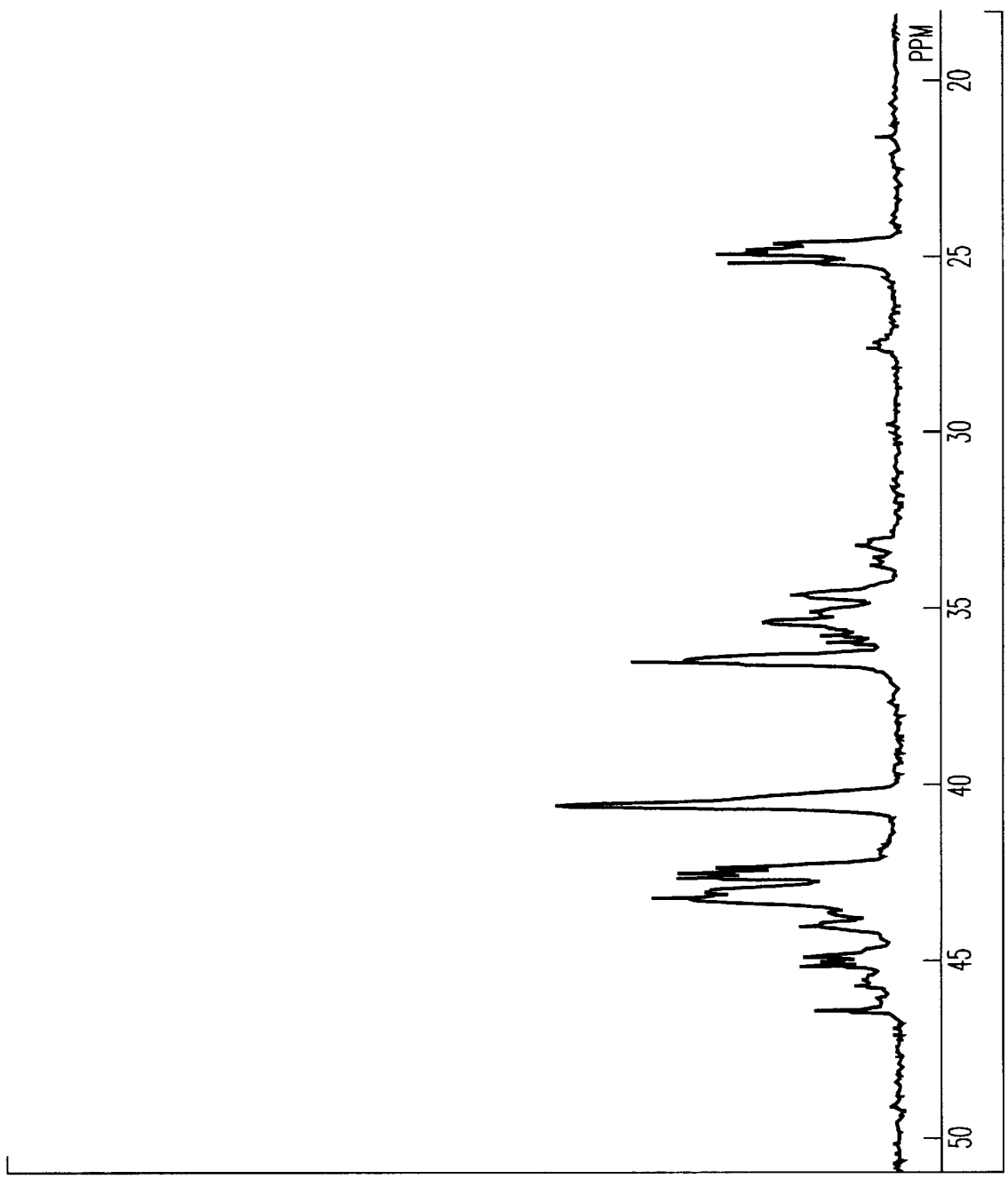
Figure 10:
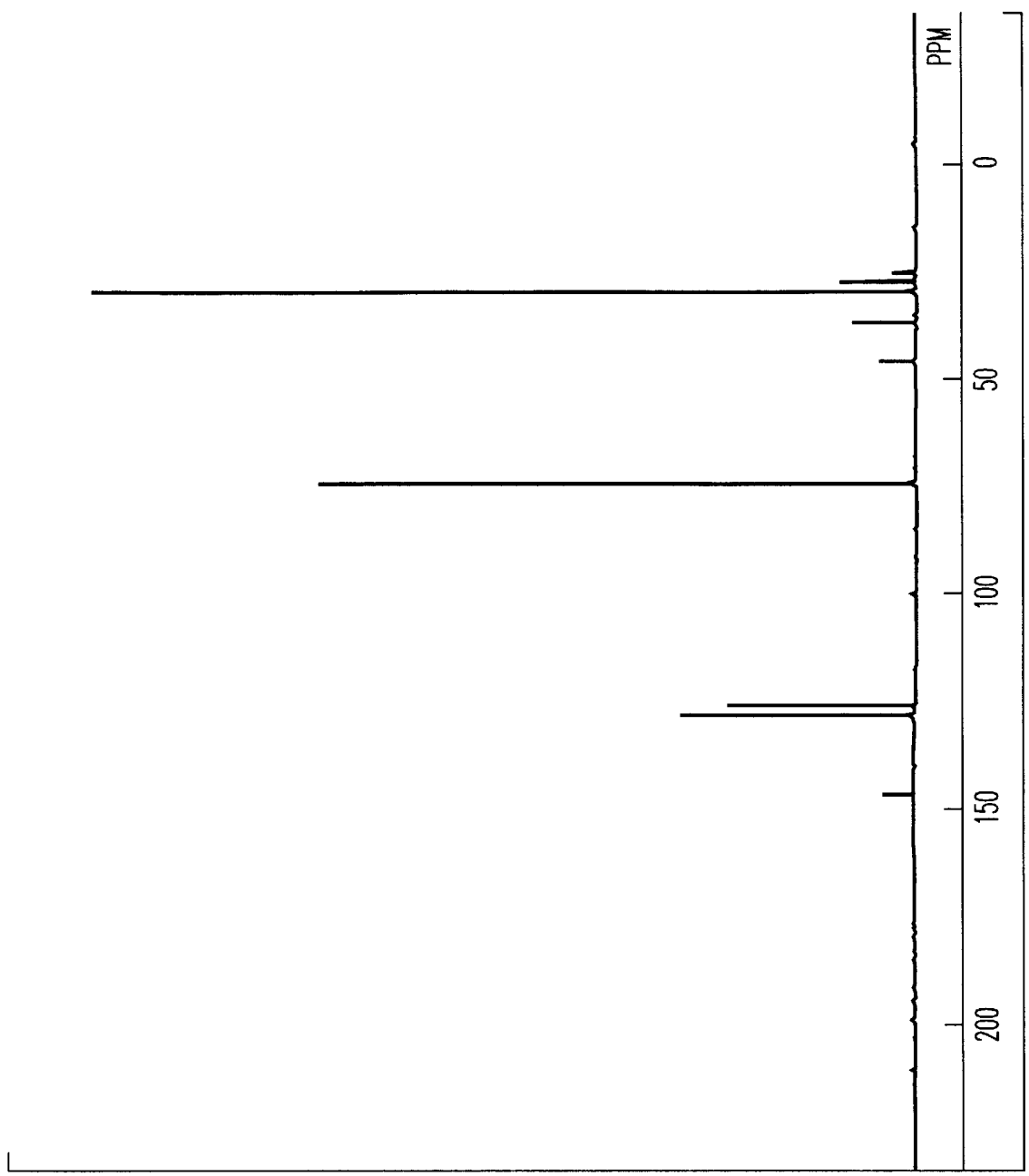
Figure 11:
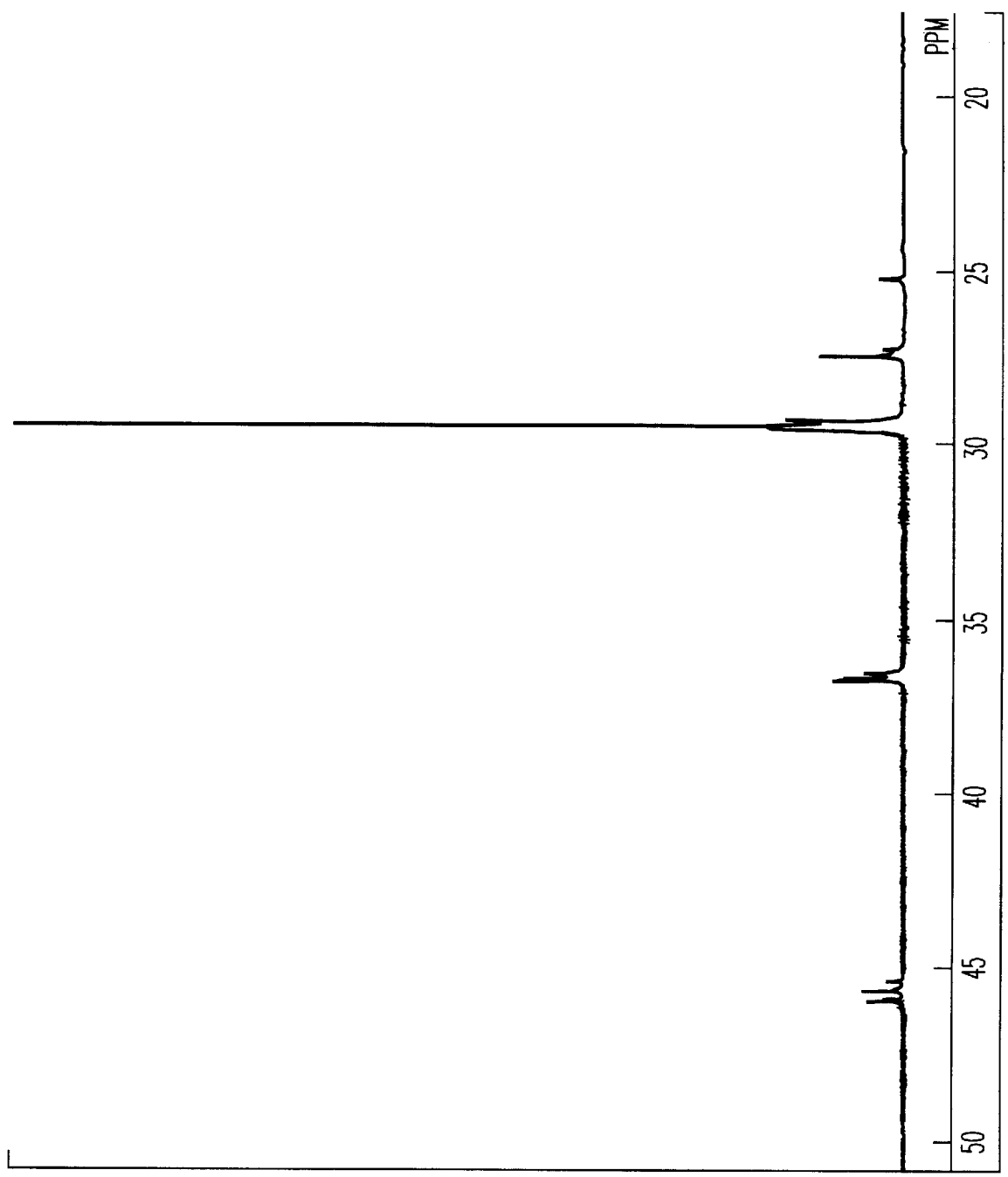
Figure 12:
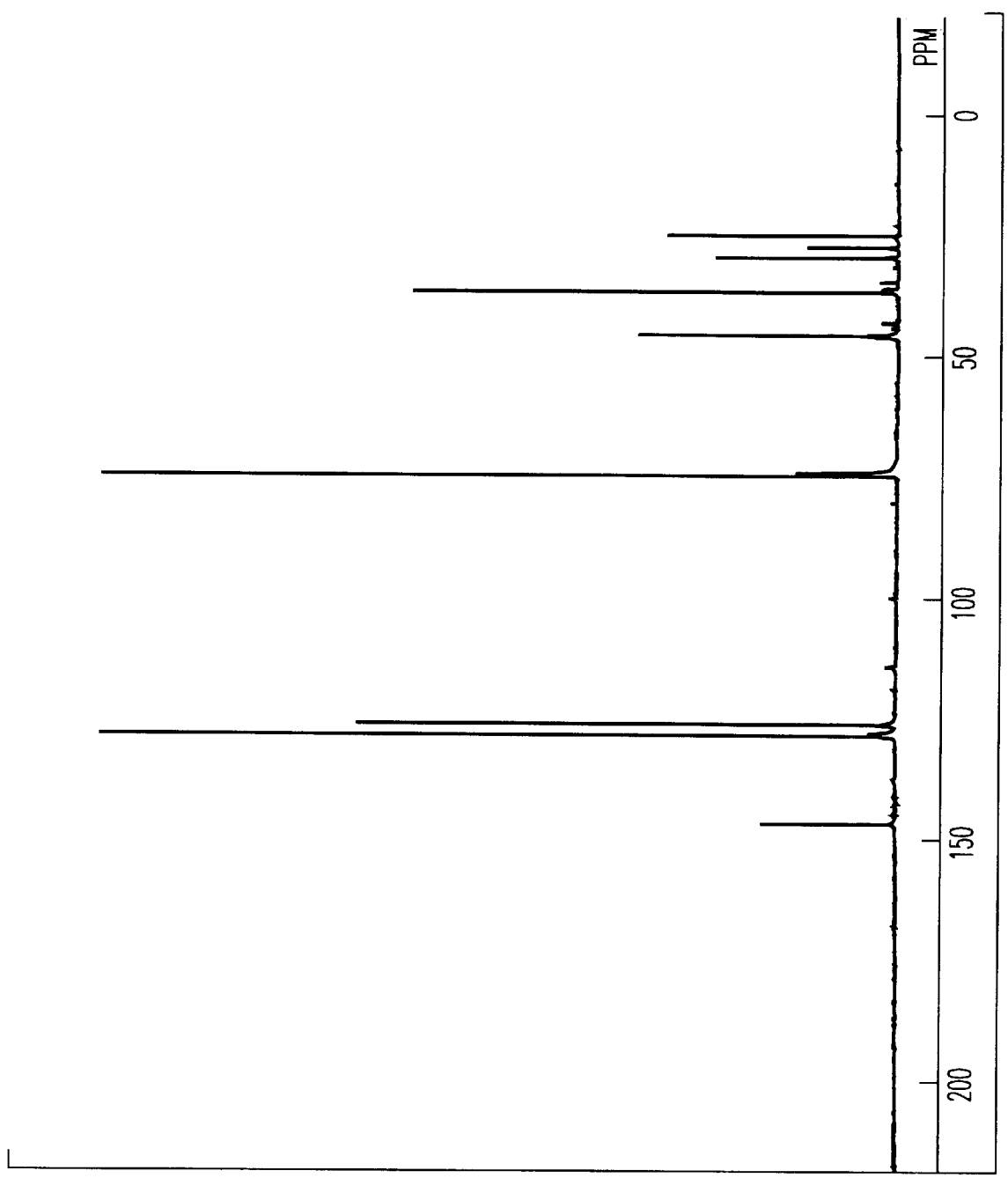
Figure 13:
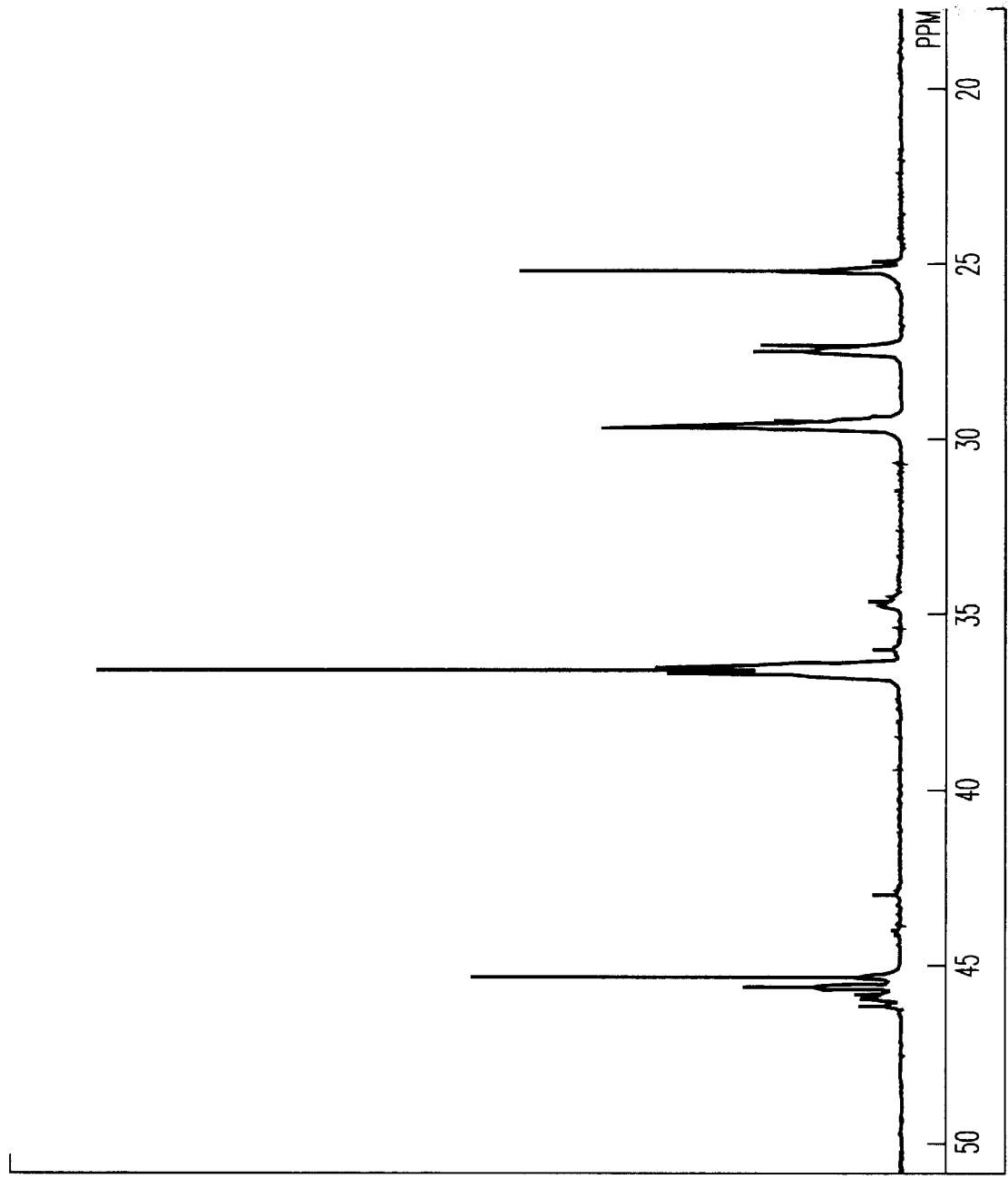
Figure 14:
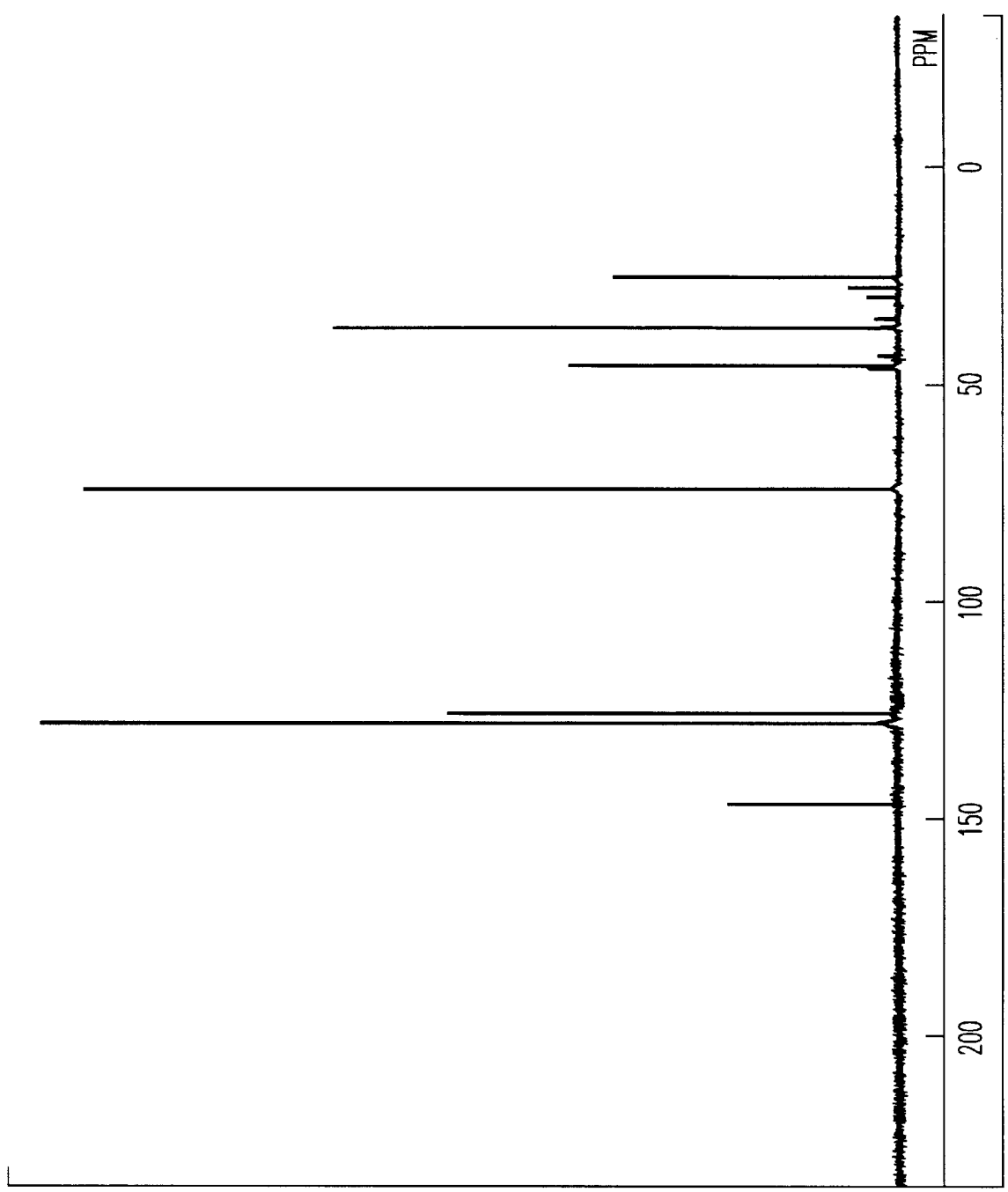
Figure 15:
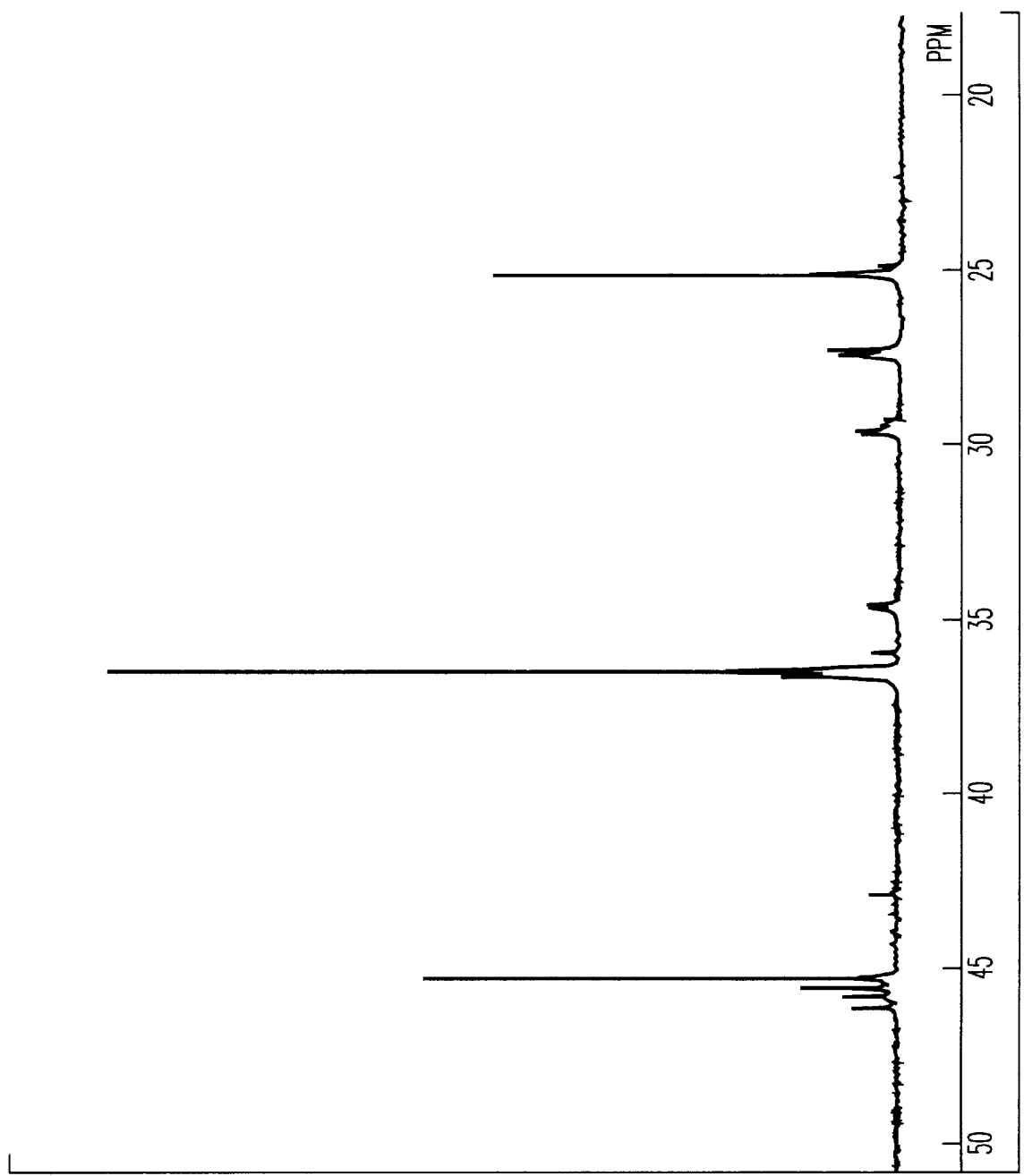
Figure 16:
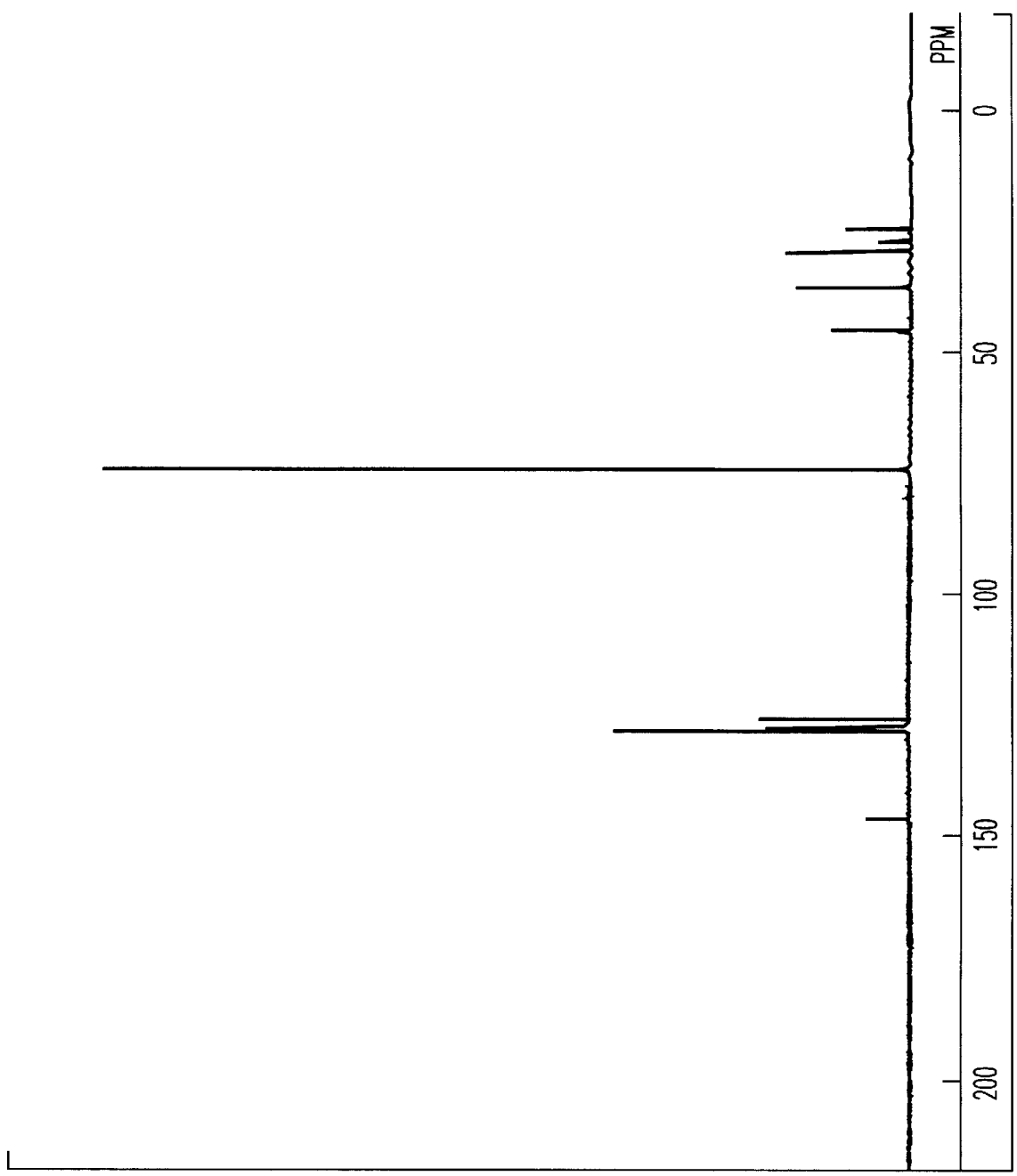
Figure 17:
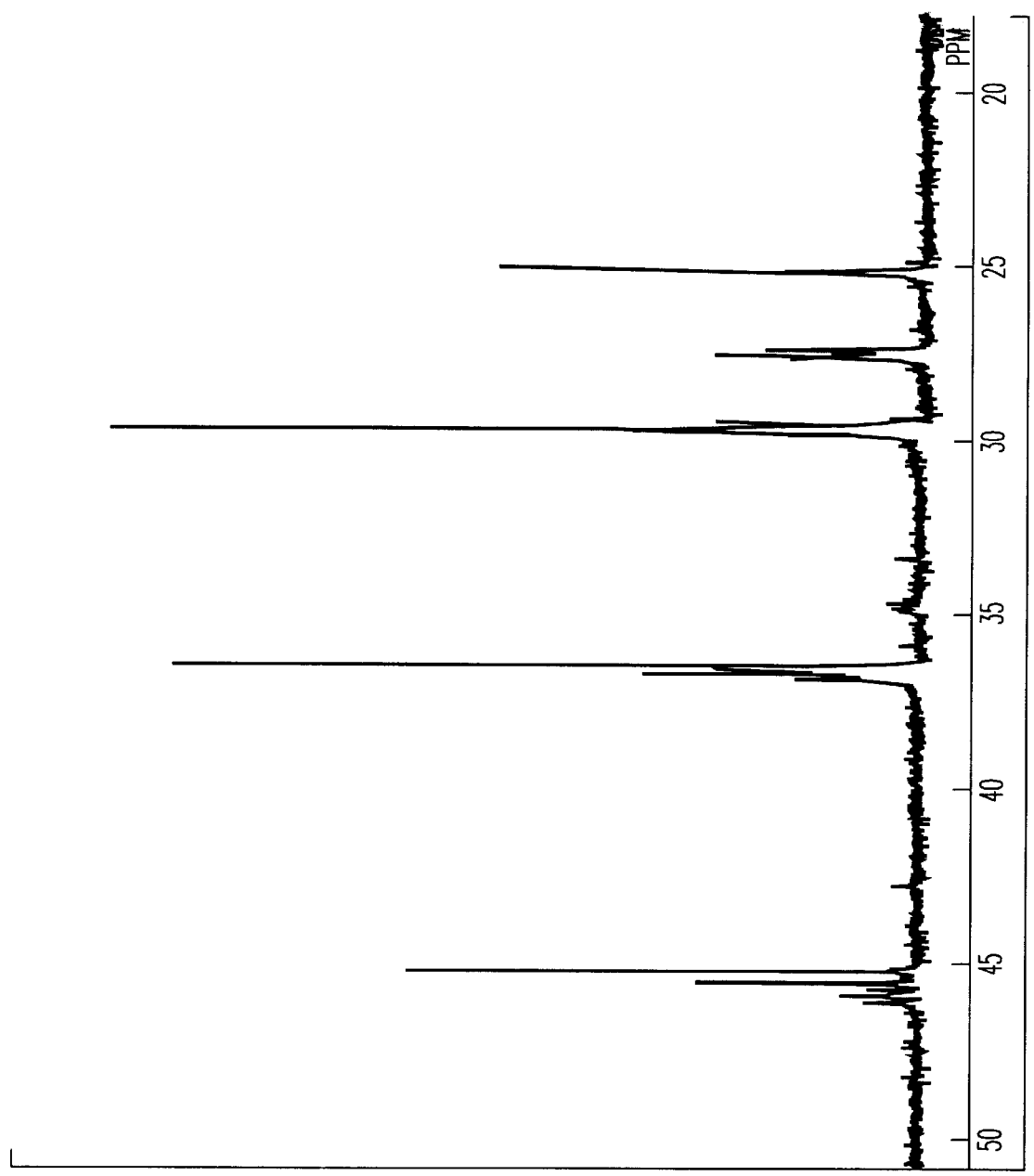
Figure 18:
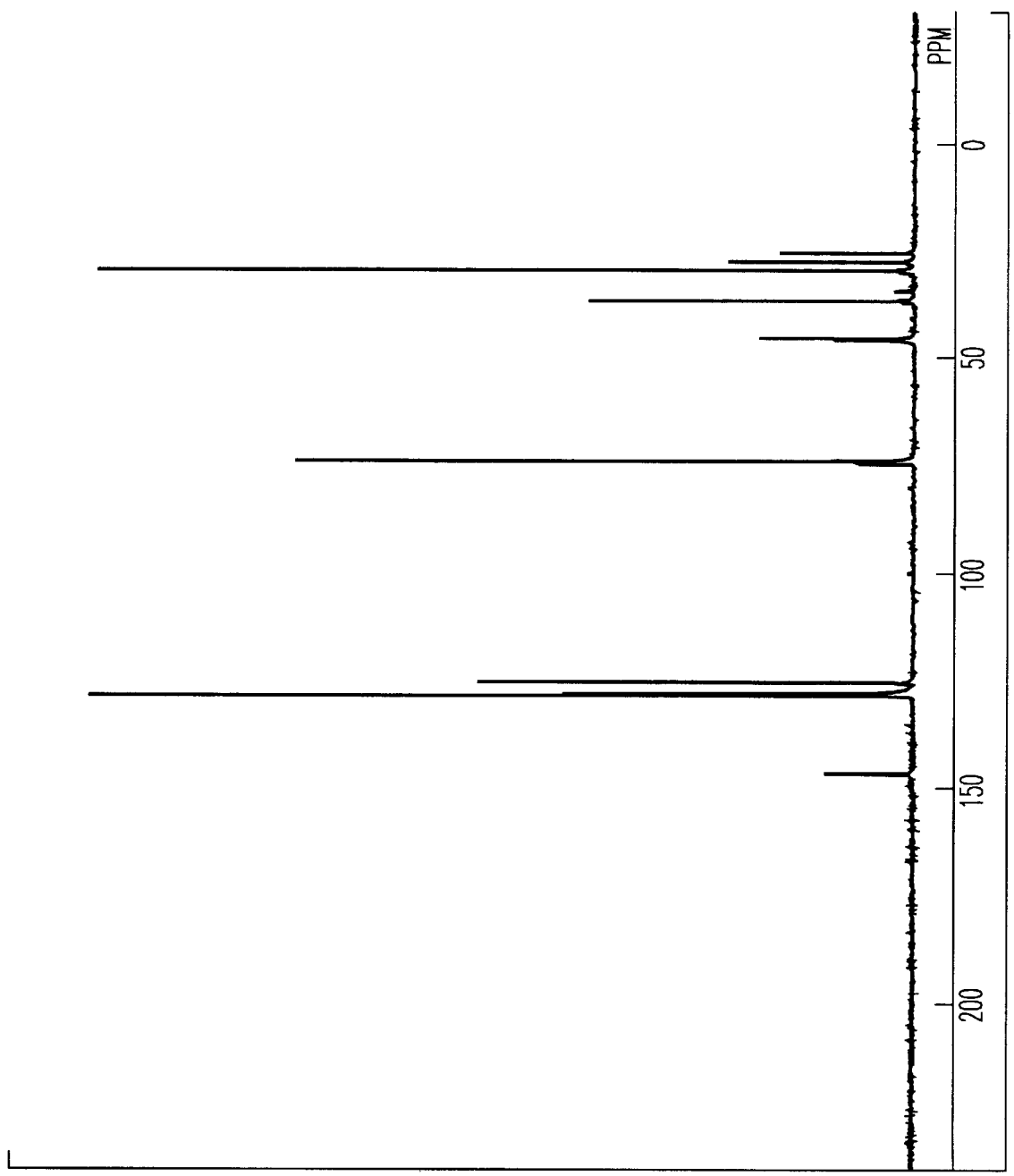
Figure 19:
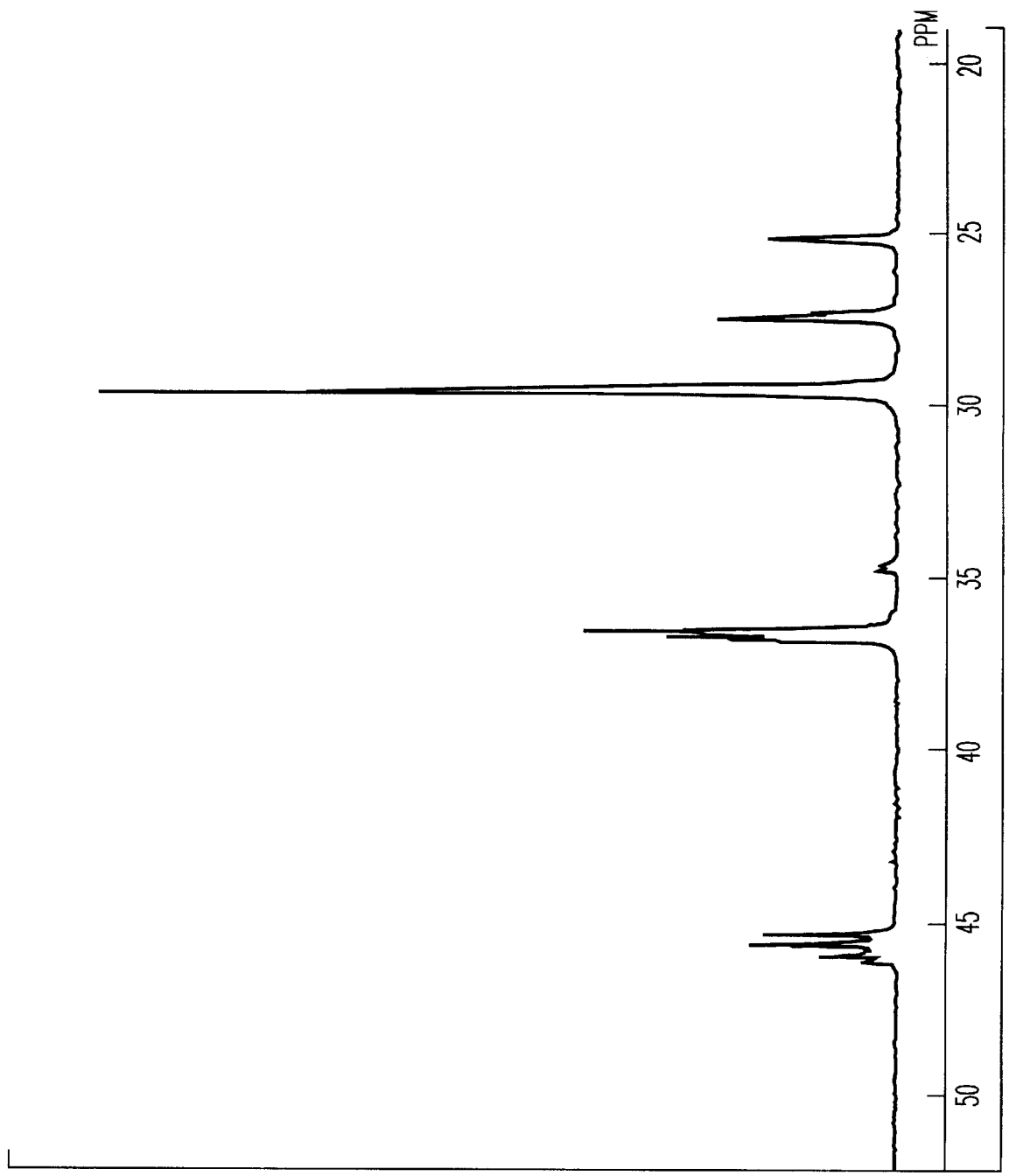
Figure 20:
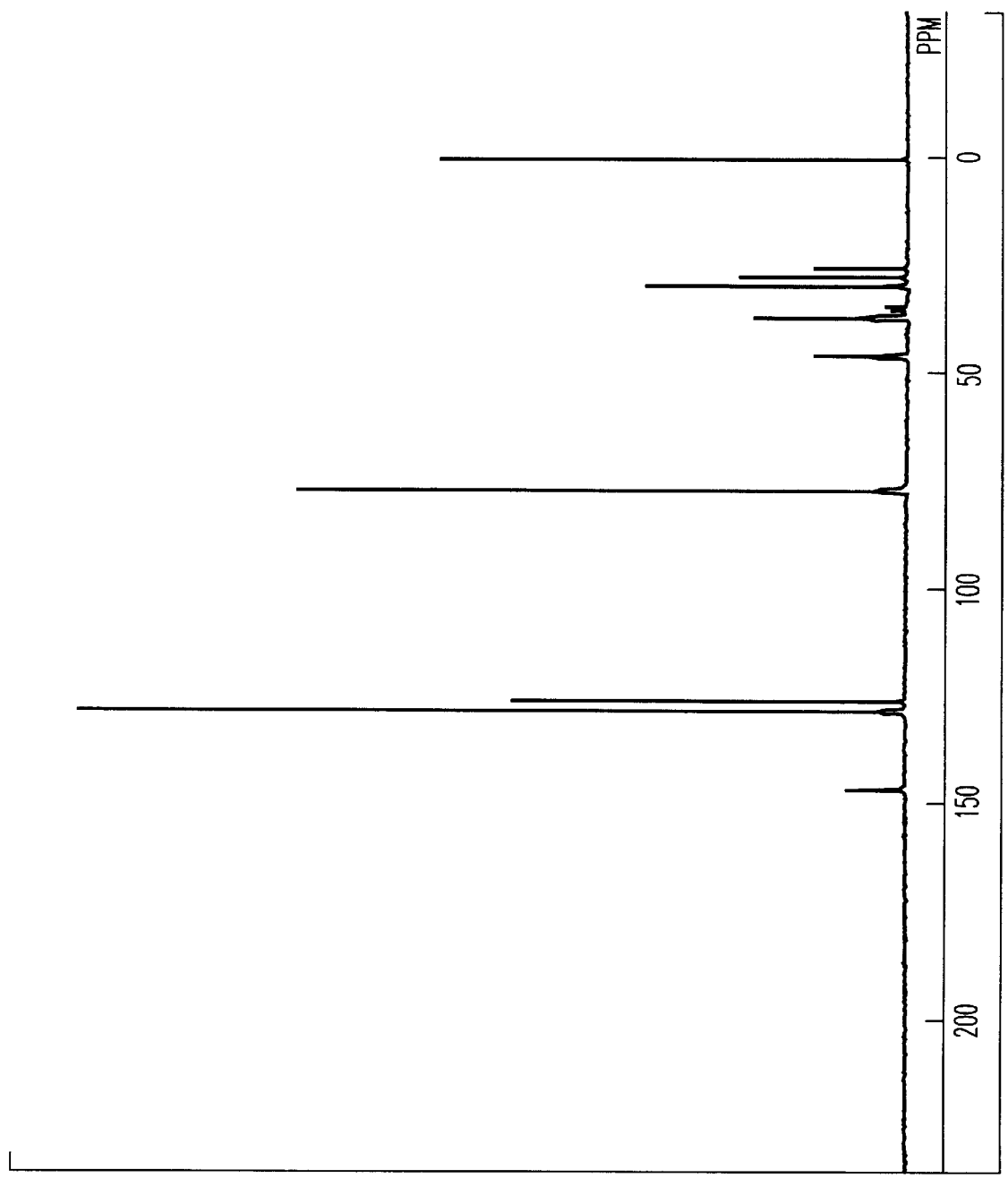
Figure 21:
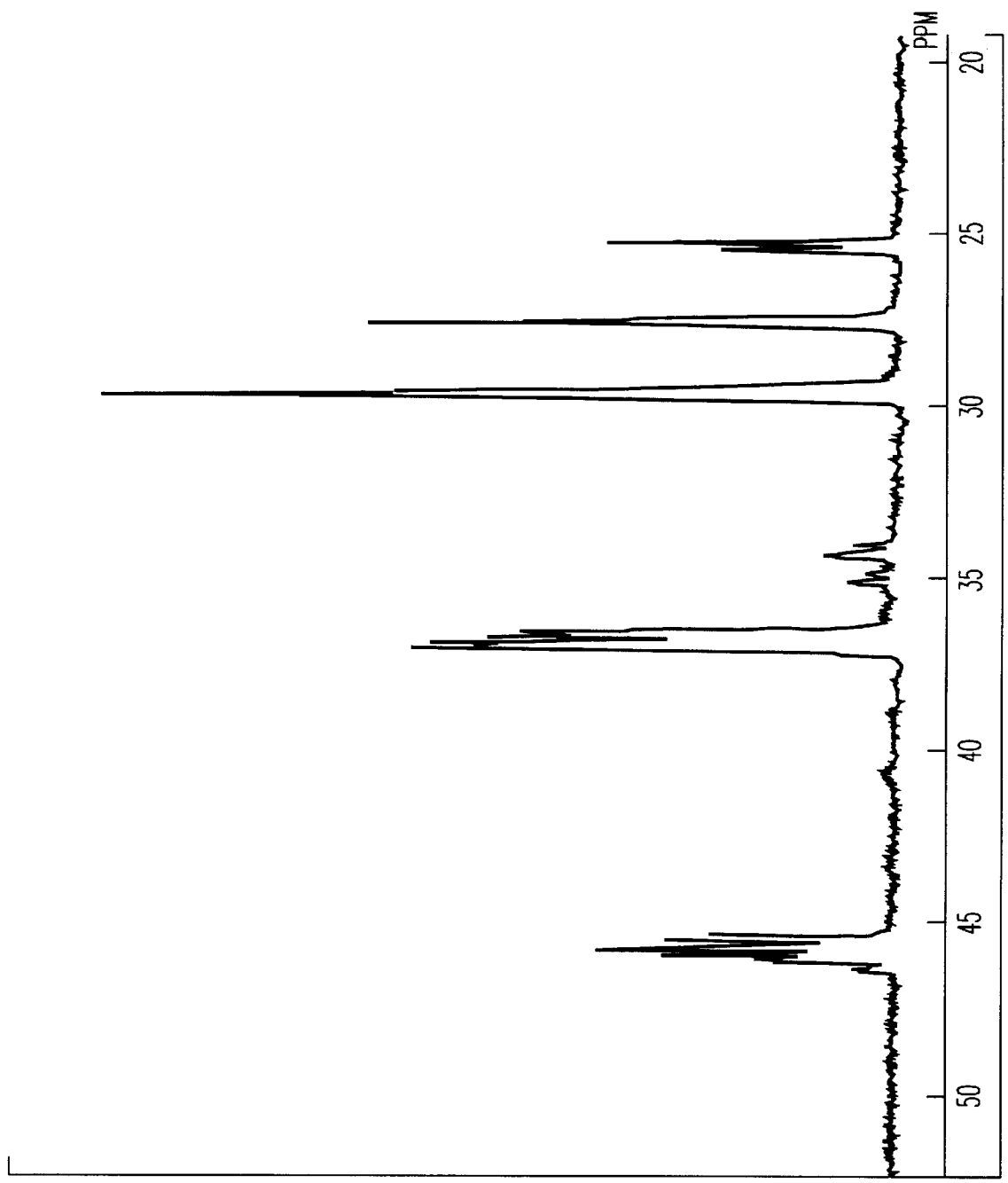
Figure 22:
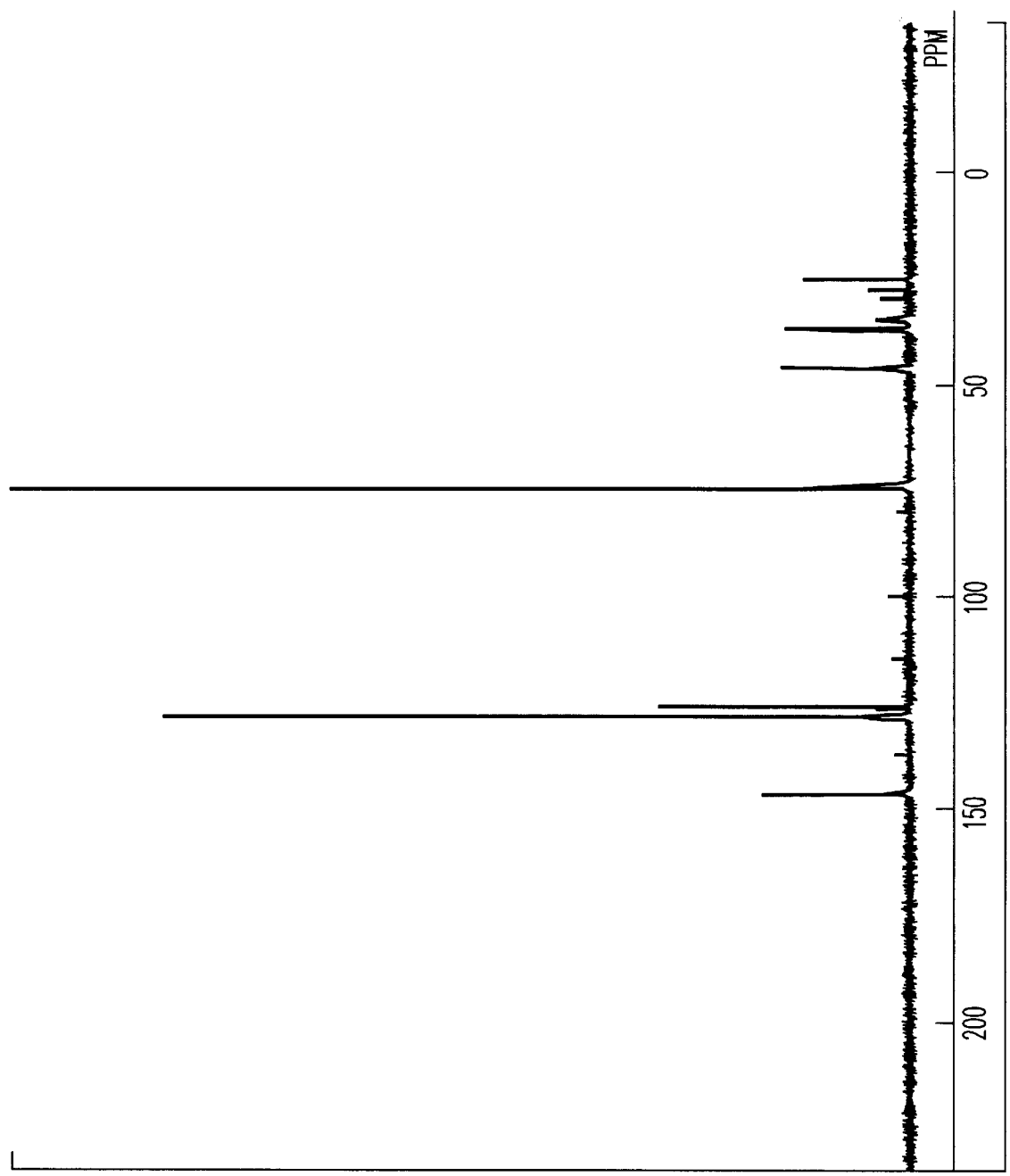
Figure 23:
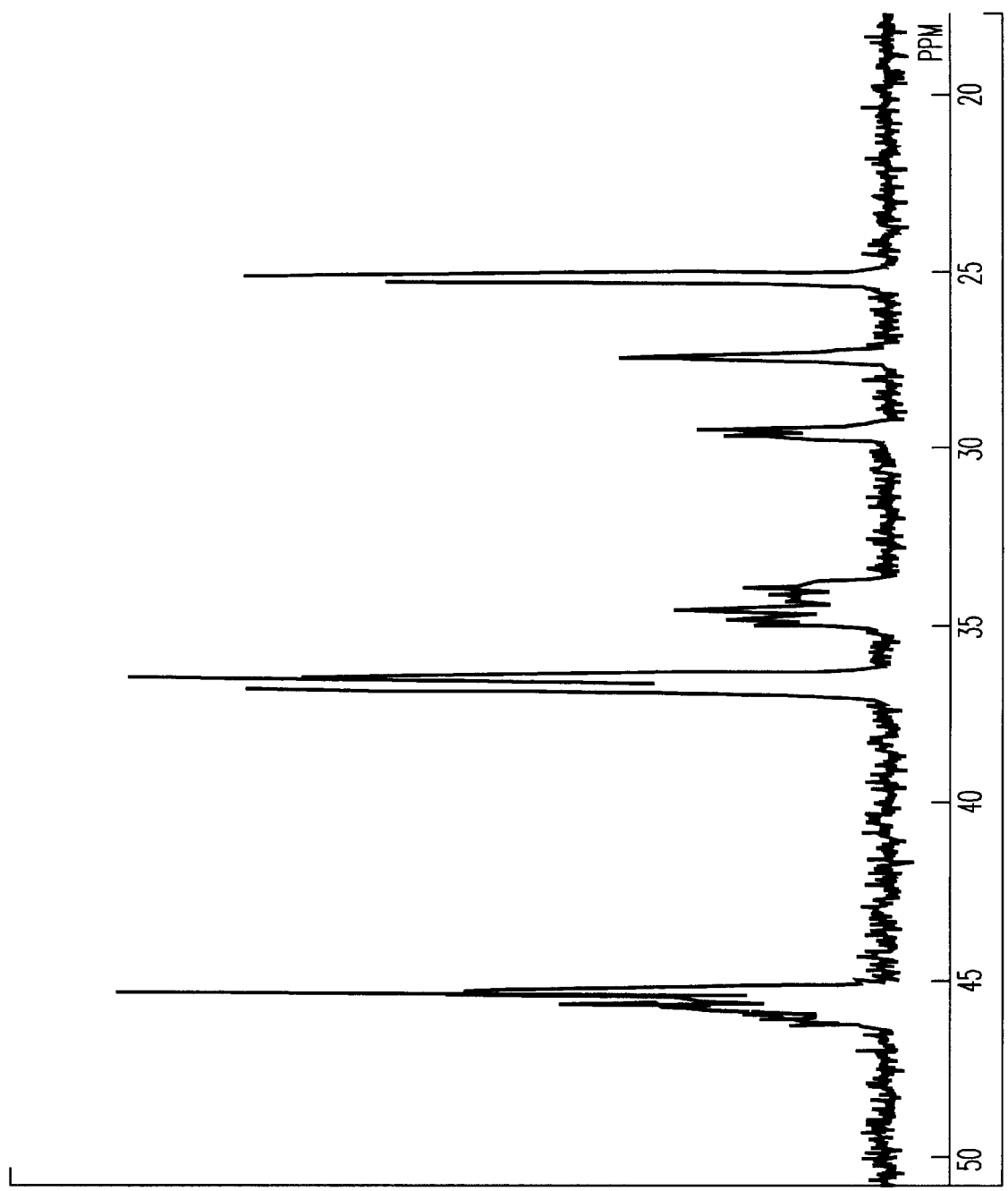
Figure 24:
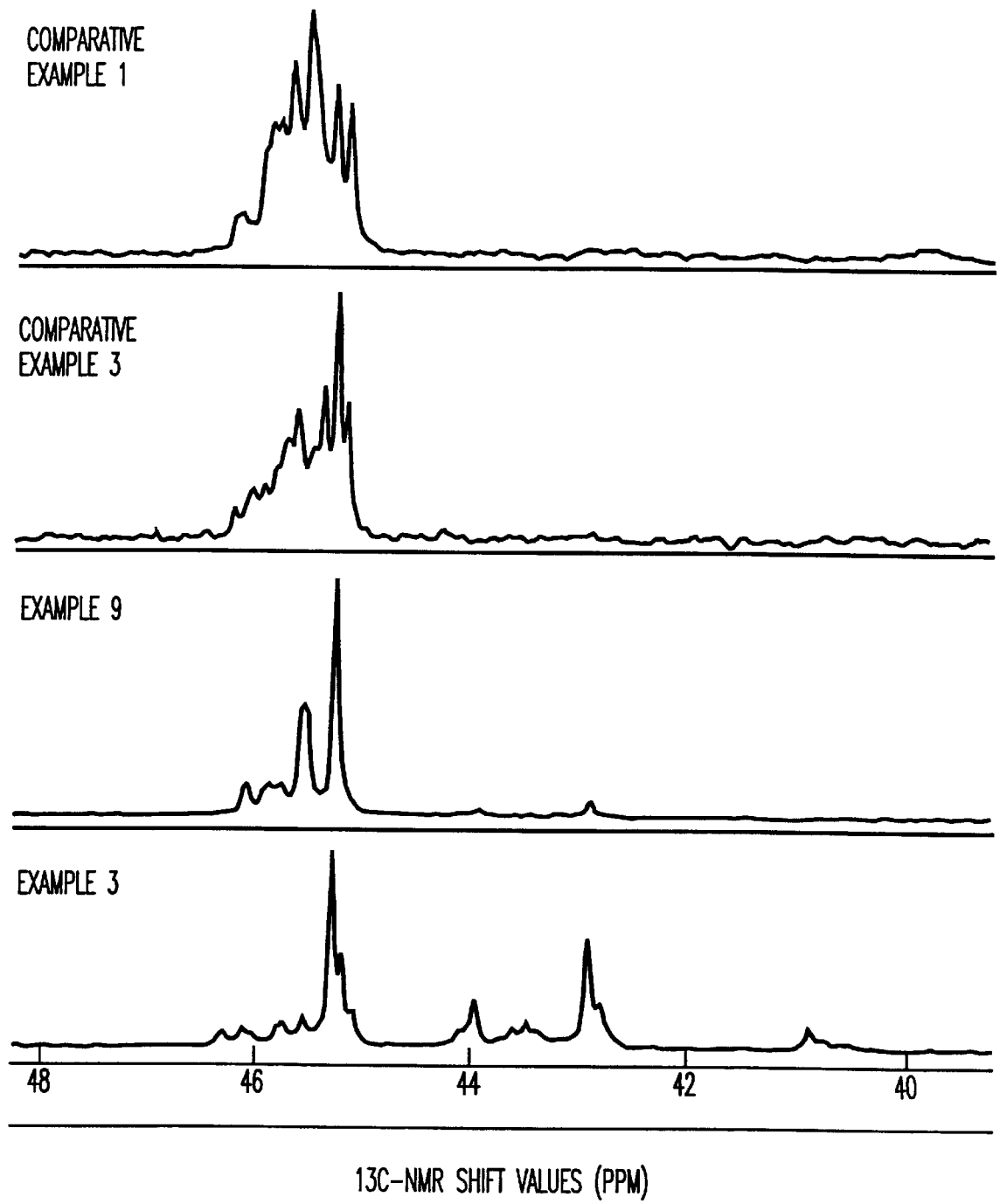

FIG. 6 is a 13C-NMR chart of the styrene-ethylene random copolymer obtained in Example 3. Entire spectrum FIG. 7 is a 13C-NMR chart of the styrene-ethylene random copolymer obtained in Example 3. methine-methylene region FIG. 8 is a 13C-NMR chart of the styrene-ethylene random copolymer obtained in Example 4. Entire spectrum FIG. 9 is a 13C-NMR chart of the styrene-ethylene random copolymer obtained in Example 4. Methine-methylene region FIG. 10 is a 13C-NMR chart of the styrene-ethylene random copolymer obtained in Example 6. Entire spectrum FIG. 11 is a 13C-NMR chart of the styrene-ethylene random copolymer obtained in Example 6. Methine-methylene region FIG. 12 is a 13C-NMR chart of the styrene-ethylene random copolymer obtained in Example 9. Entire spectrum FIG. 13 is a 13C-NMR chart of the styrene-thylene random copolymer obtained in Example 9. Methine-methylene region FIG. 14 is a 13C-NMR chart of the styrene-ethylene random copolymer obtained in Example 10. Entire spectrum FIG. 15 is a 13C-NMR chart of the styrene-ethylene random copolymer obtained in Example 10. Methine-methylene region FIG. 16 is a 13C-NMR chart of the styrene-ethylene random copolymer obtained in Example 12. Entire spectrum FIG. 17 is a 13C-NMR chart of the styrene-ethylene random copolymer obtained in Example 12. Methine-methylene region FIG. 18 is a 13C-NMR chart of the styrene-ethylene random copolymer obtained in Example 13. Entire spectrum FIG. 19 is a 13C-NMR chart of the styrene-ethylene random copolymer obtained in Example 13. Methine-methylene region FIG. 20 is a 13C-NMR chart of a styrene-ethylene pseudo random copolymer obtained in Comparative Example 1. Entire spectrum FIG. 21 is a 13C-NMR chart of the styrene-ethylene pseudo random copolymer obtained in Comparative Example 1 Methine-methylene region FIG. 22 is a 13C-NMR chart of a styrene-ethylene pseudo random copolymer obtained in Comparative Example 3. Entire spectrum FIG. 23 is a 13C-NMR chart of the styrene-ethylene pseudo random copolymer obtained in Comparative Example 3. Methine-methylene region FIG. 24 shows 13C-NMR charts in the vicinity of 45 ppm (methine carbon peak).

Figure 25:
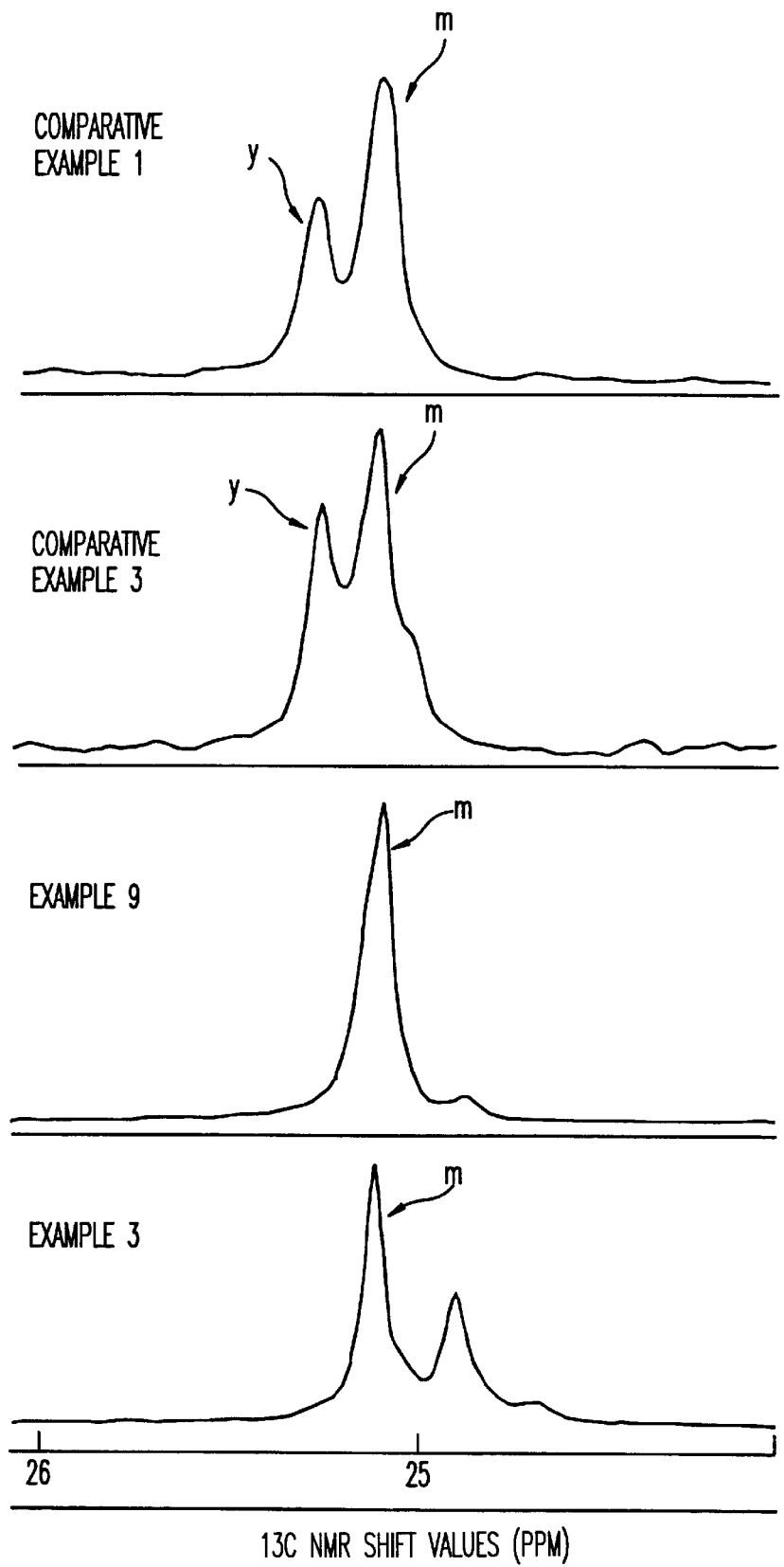

FIG. 25 shows 13C-NMR charts in the vicinity of 25 ppm (alternating structure peak).

Figure 26A:
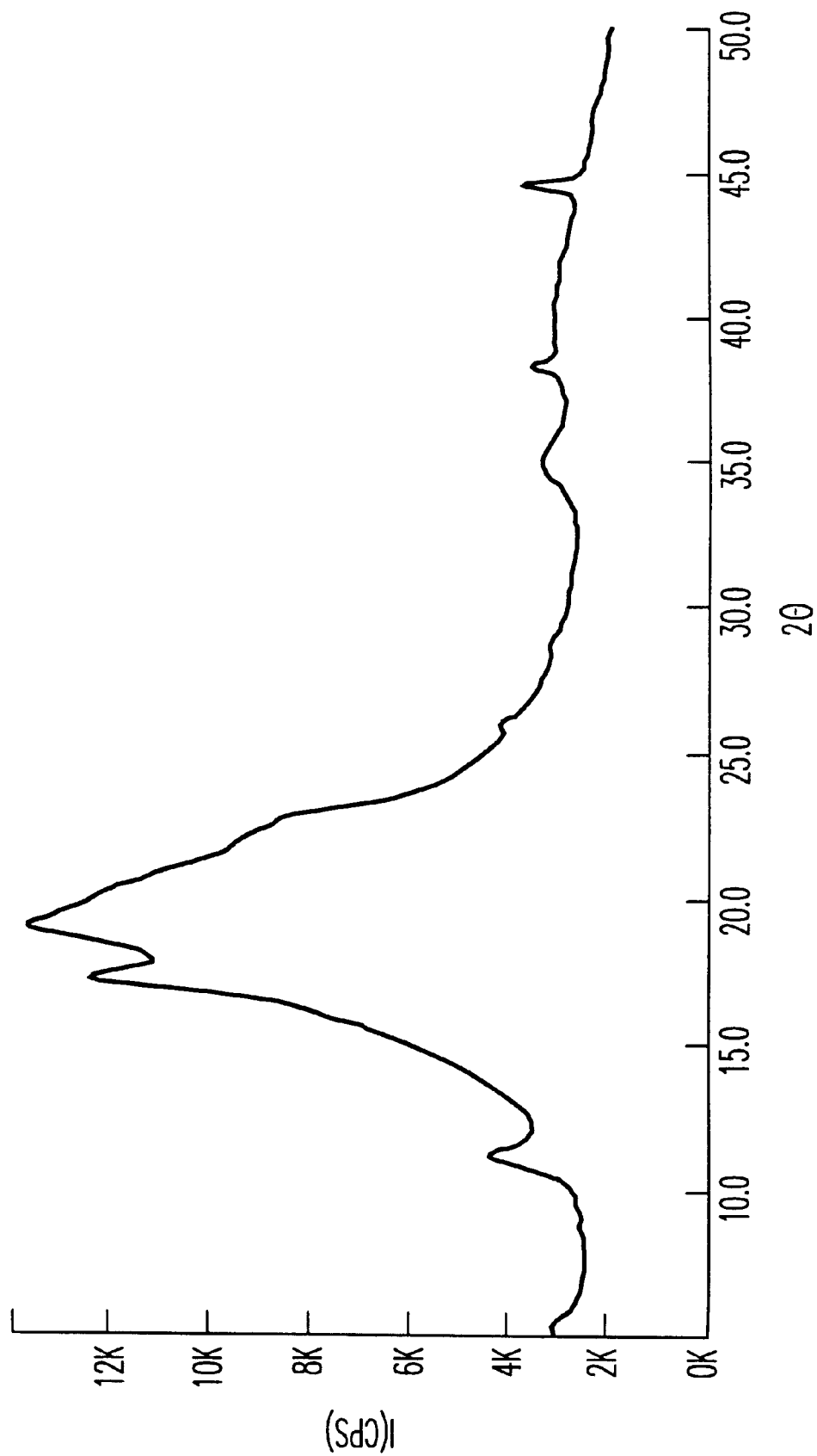
Figure 26B:
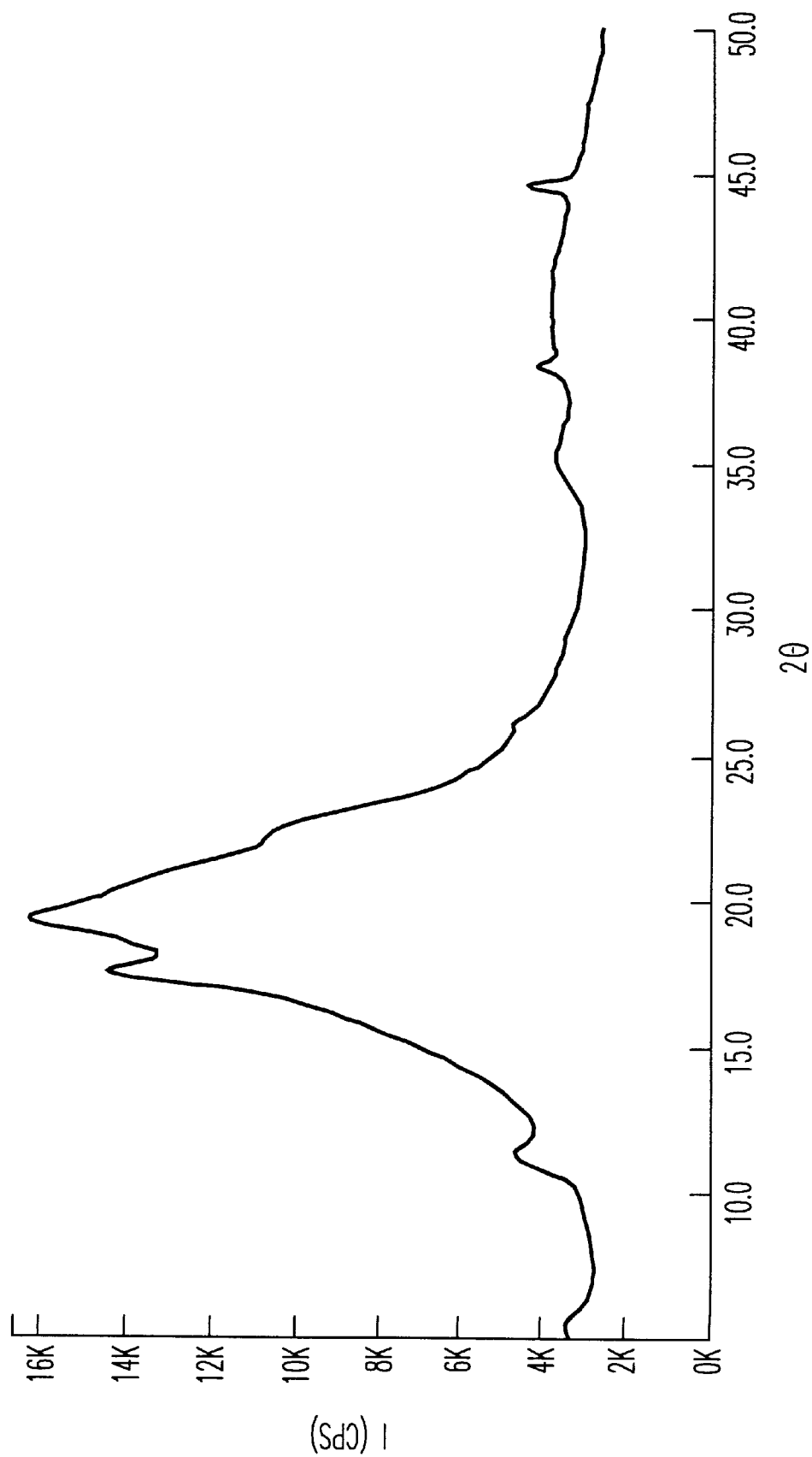

FIG. 26 shows X-ray diffraction patterns of the copolymers obtained in Examples 10 and 14.

Figure 27A:
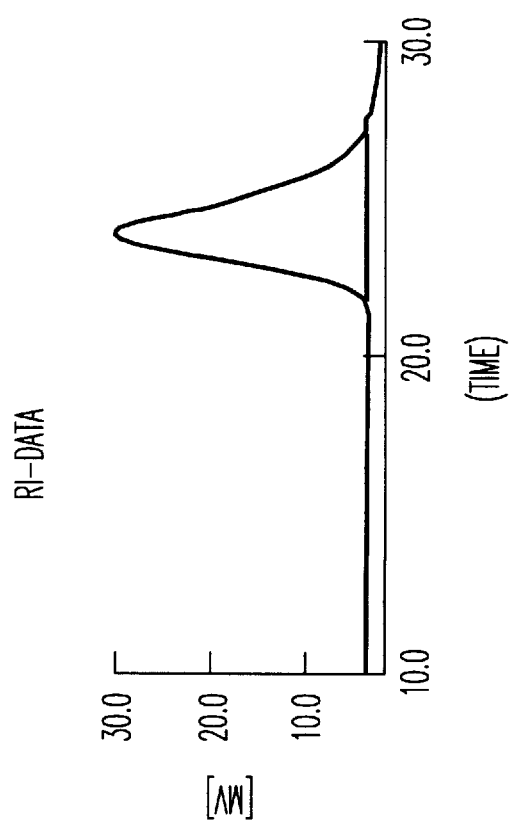
Figure 27B:
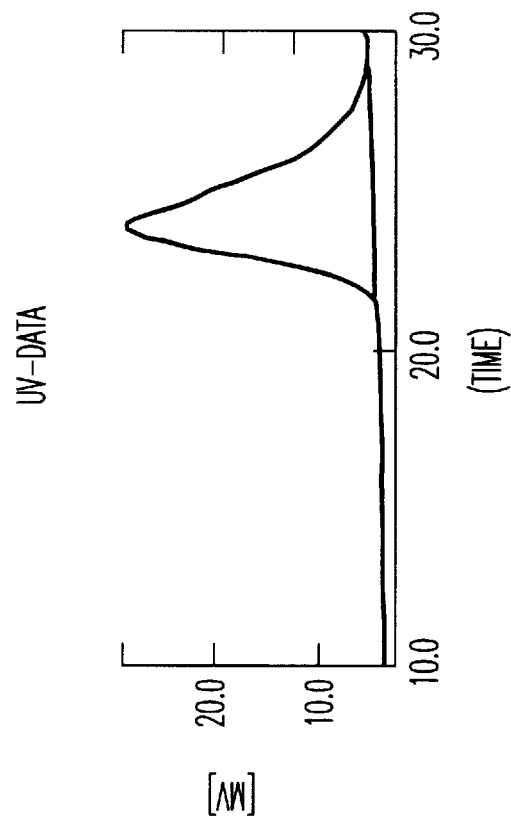

FIG. 27 is a GPC chart of the styrene-propylene random copolymer obtained in Example 15.

Figure 28:
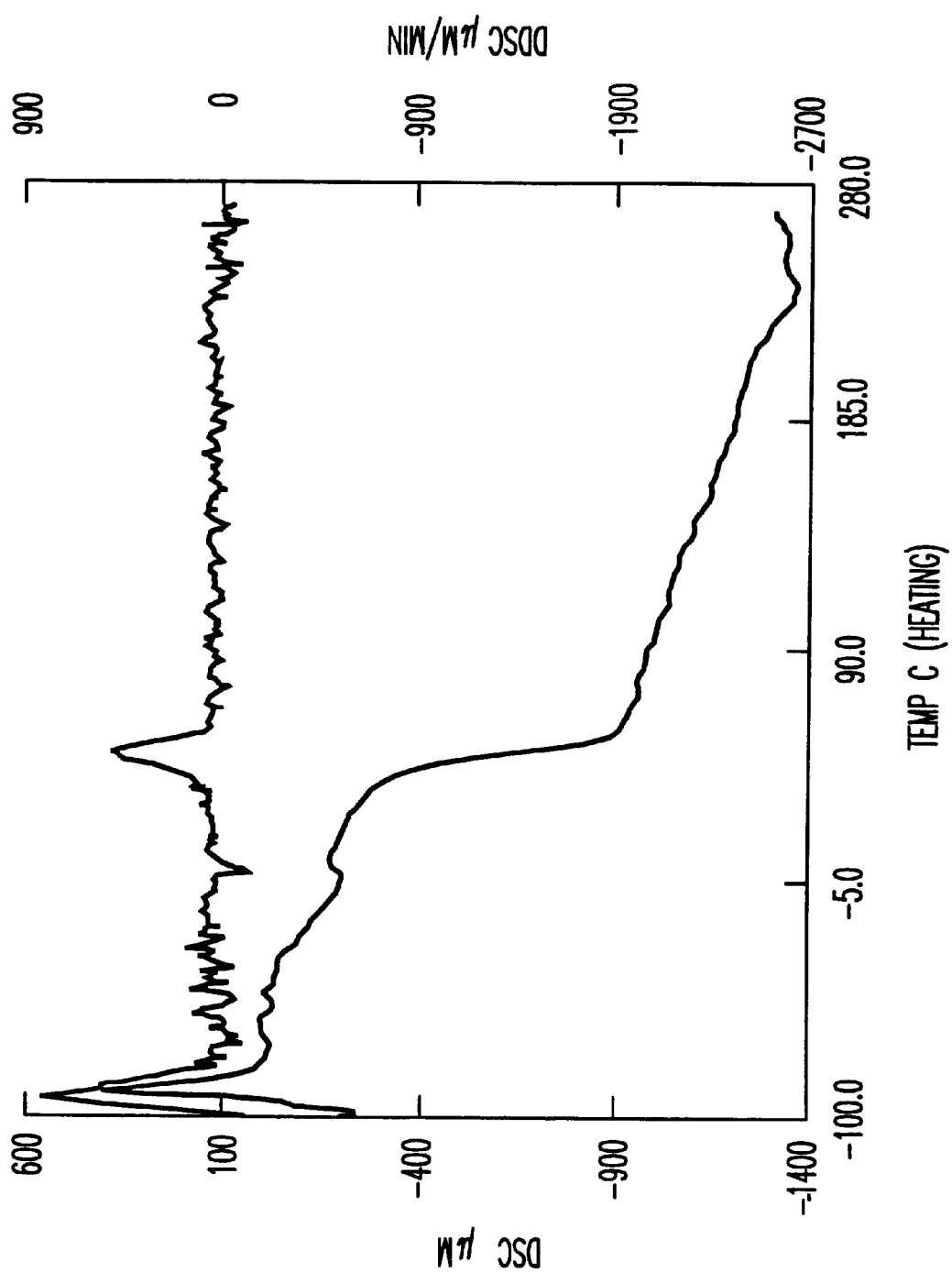

FIG. 28 is a DSC chart of the styrene-propylene random copolymer obtained in Example 15.

Figure 29:
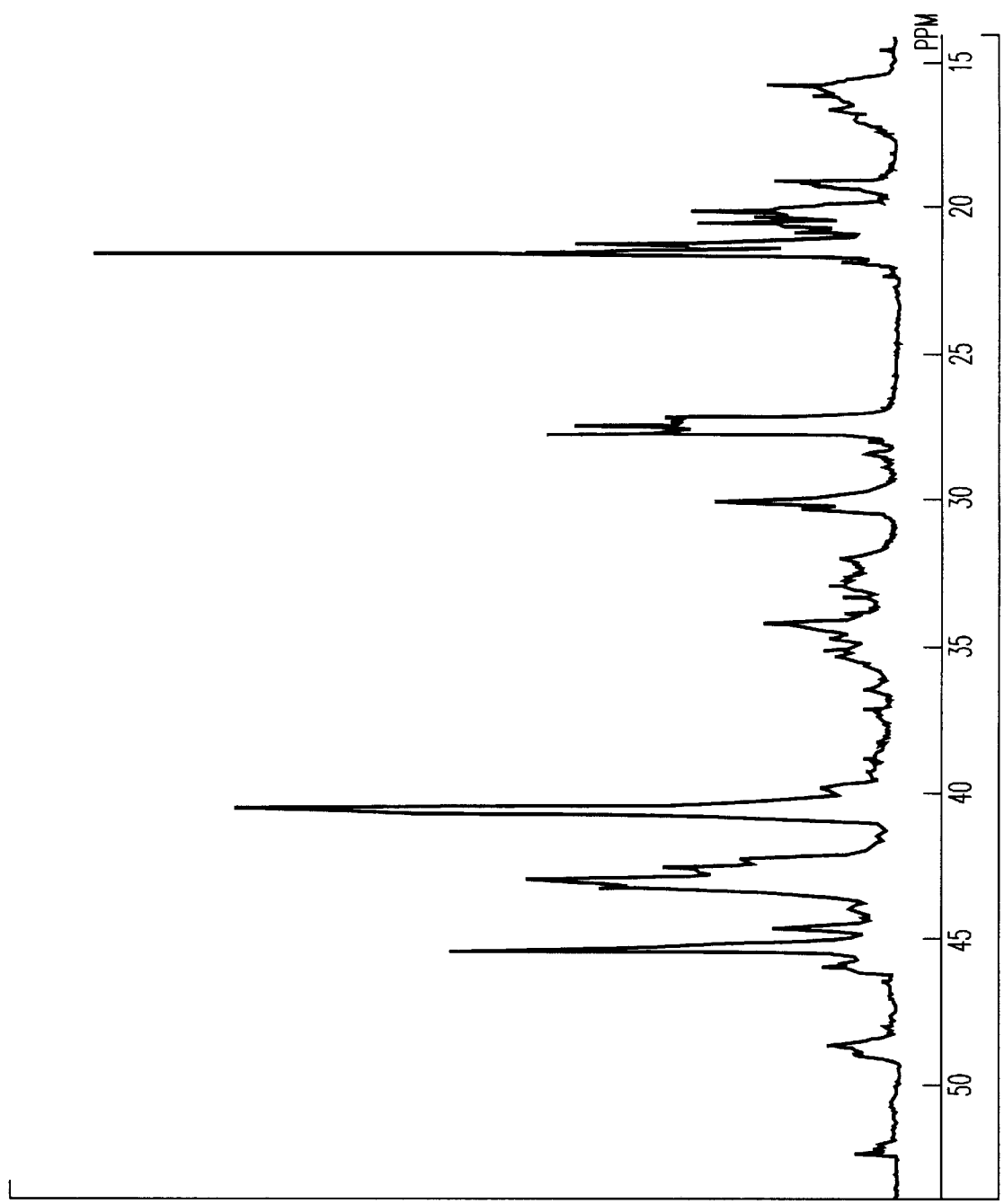
Figure 30:
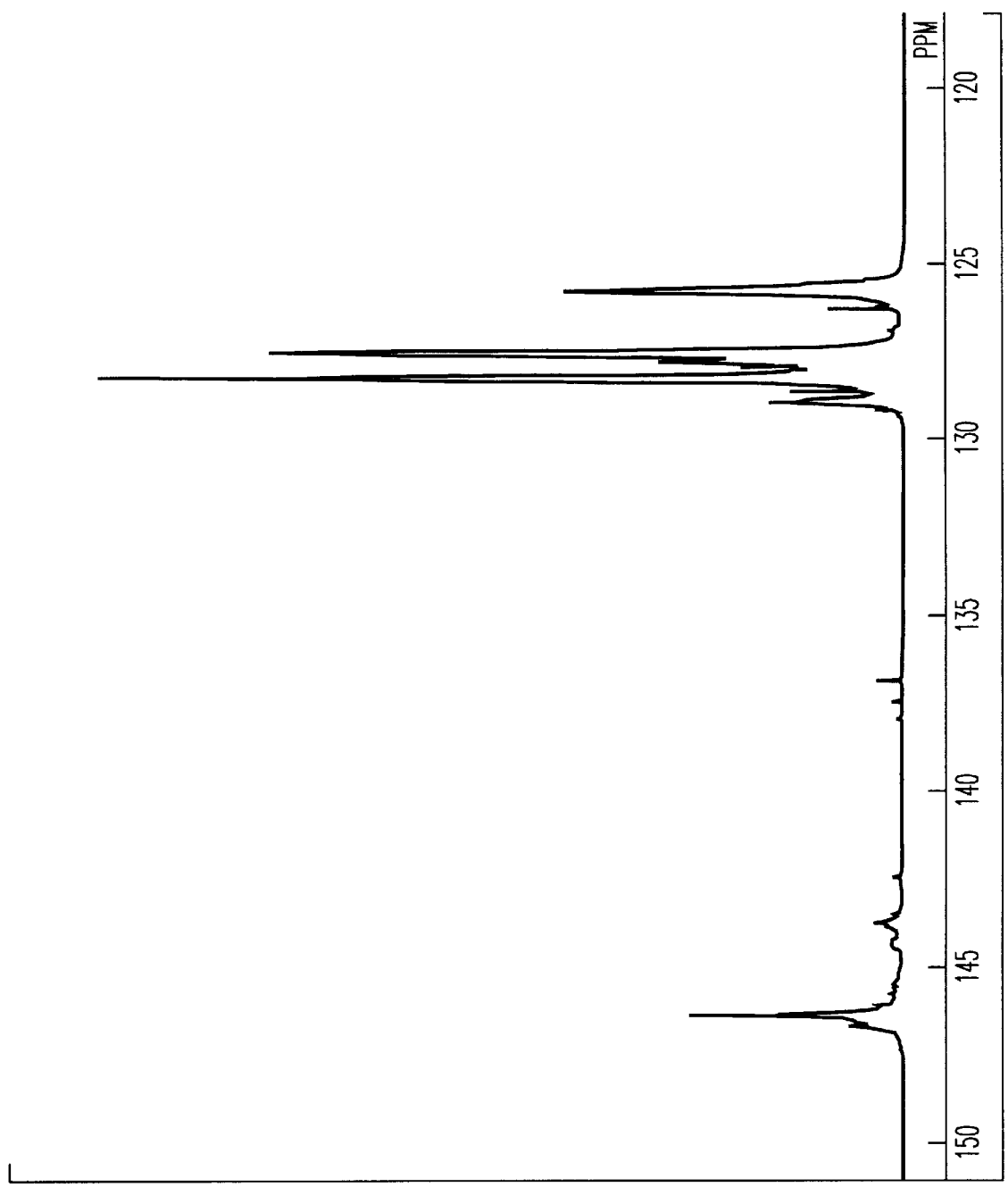
Figure 31:
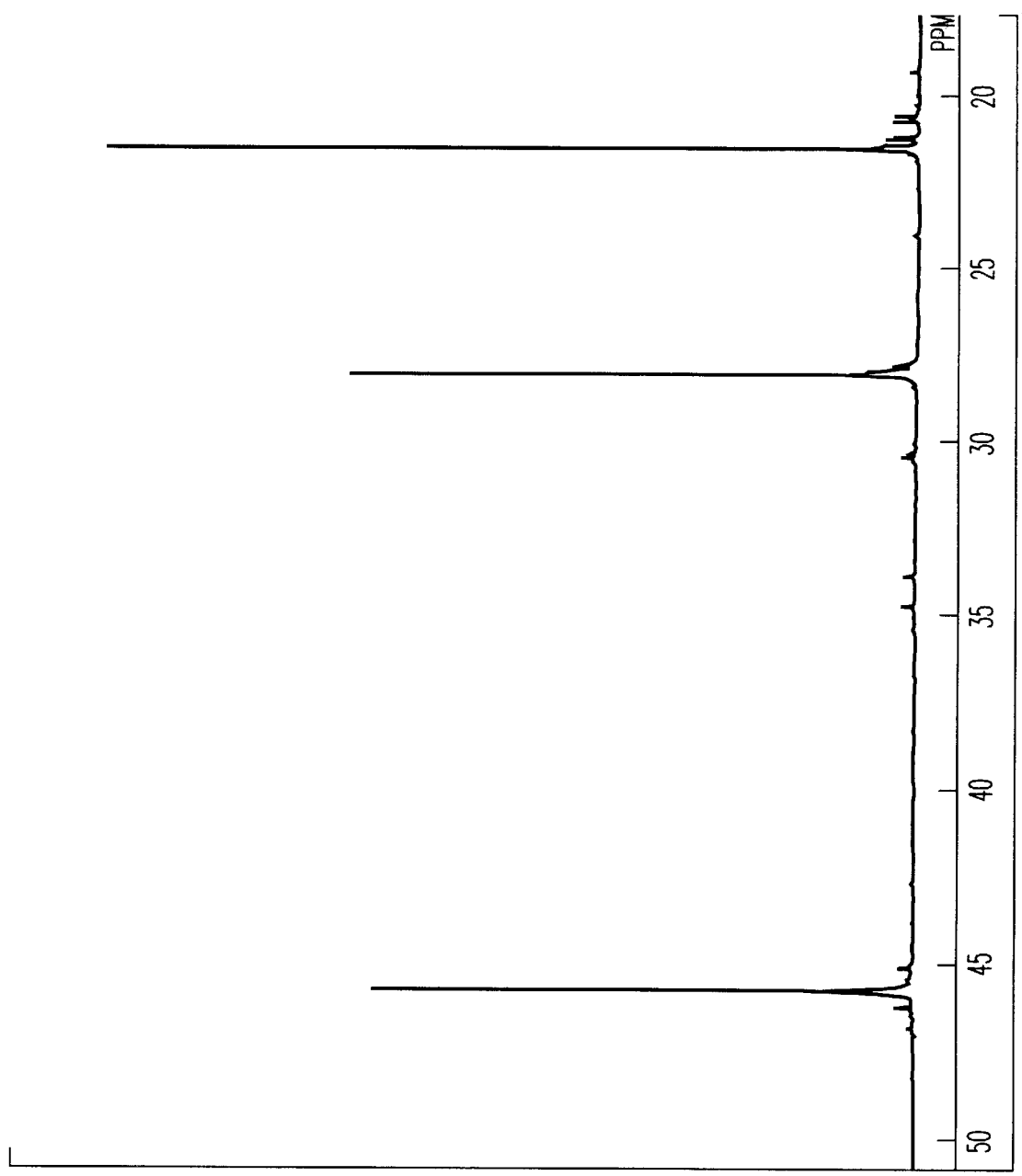
Figure 32:
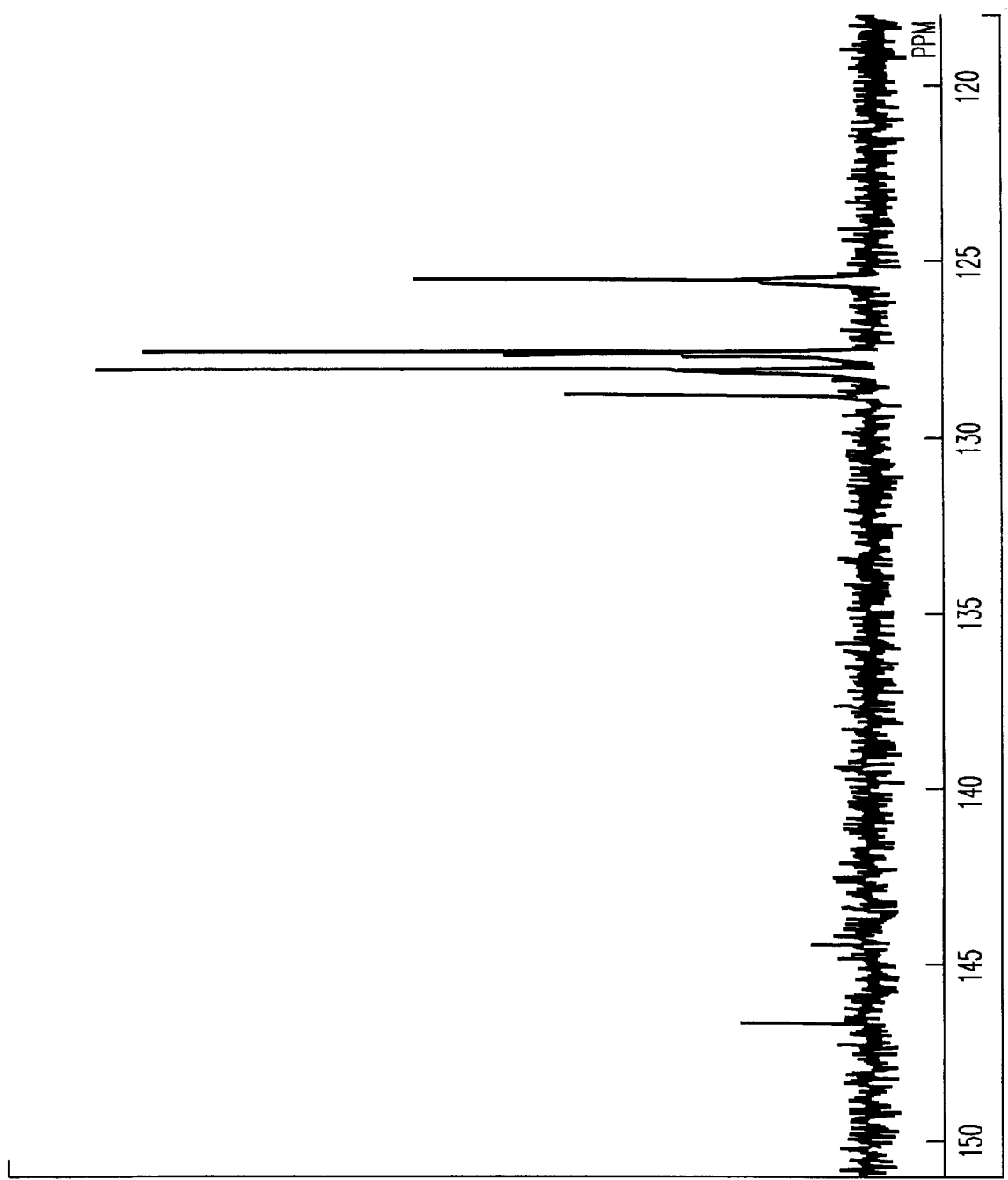
Figure 33:
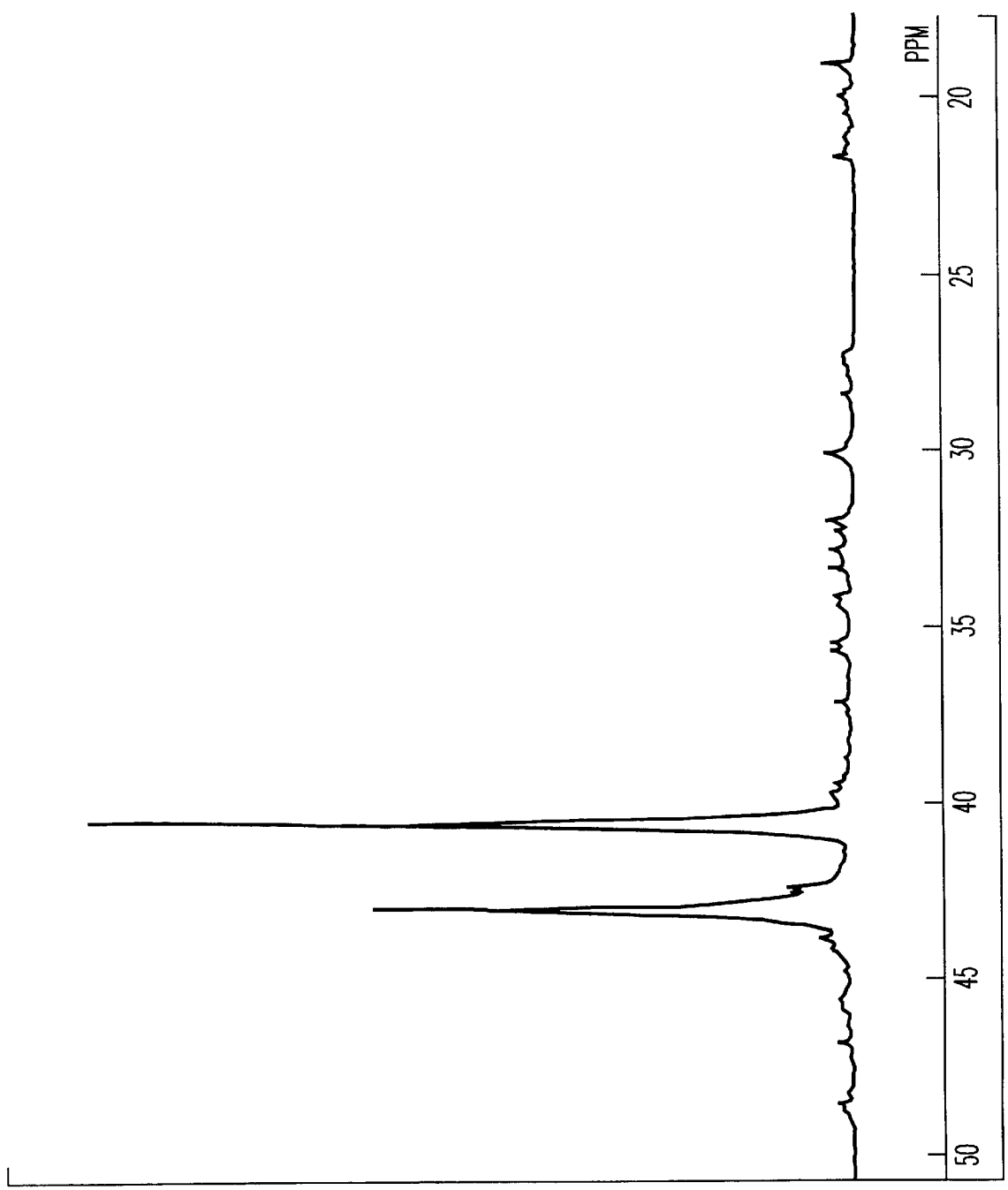
Figure 34:
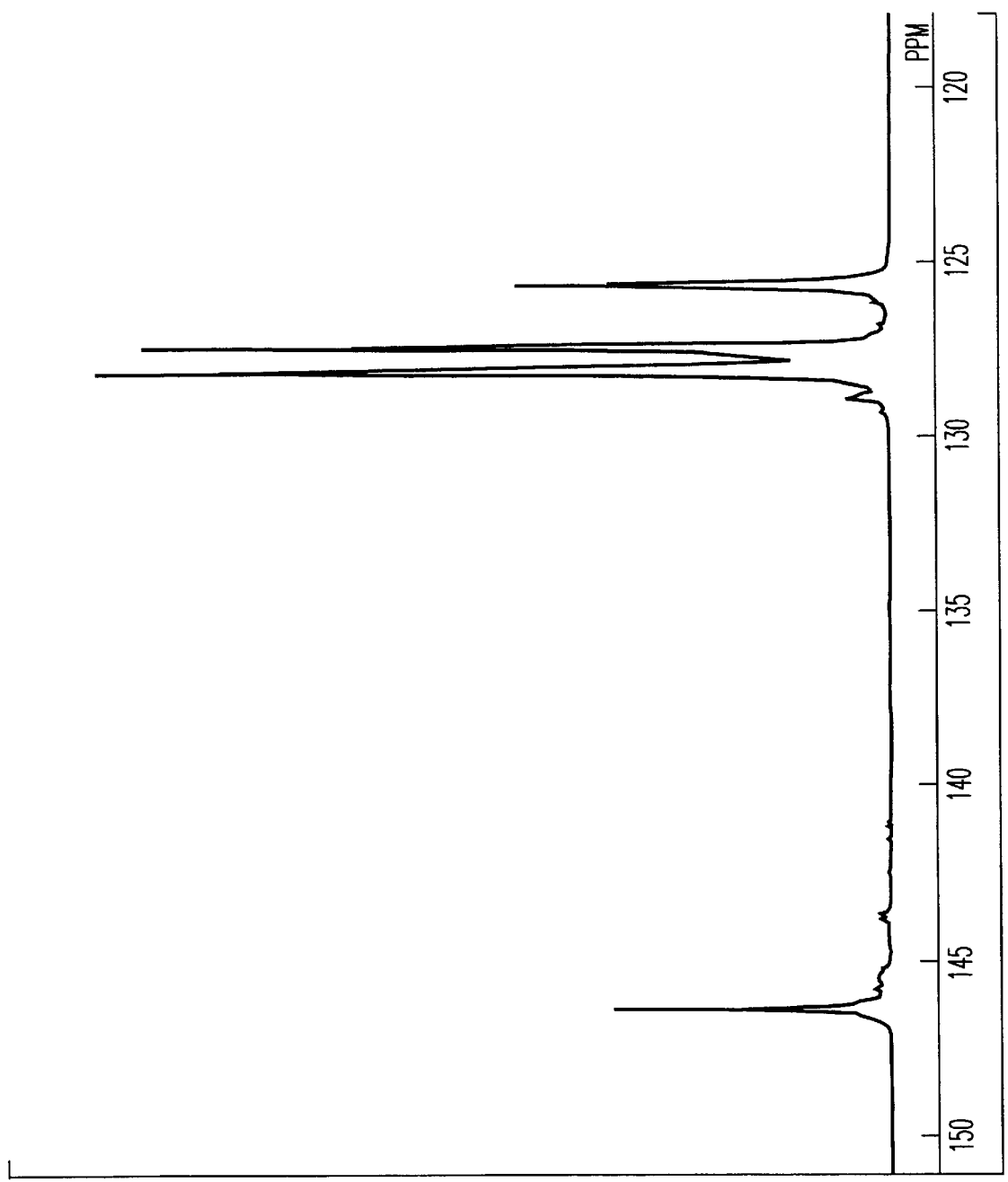
Figure 35:
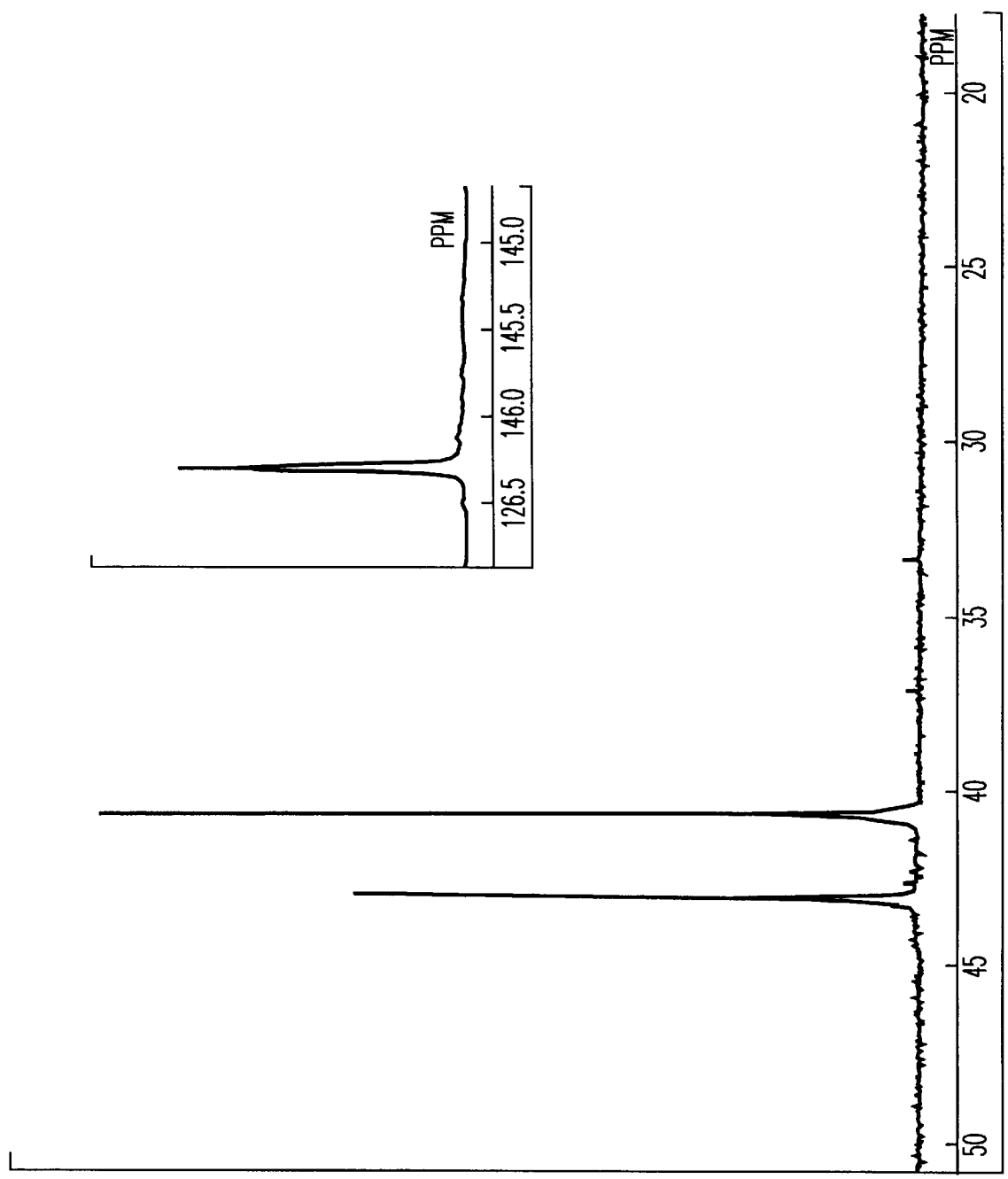

FIG. 29 is a 13C-NMR chart of the styrene-propylene random copolymer obtained in Example 15. Methine-methylene-methyl region FIG. 30 is a 13C-NMR chart of the styrene-propylene random copolymer obtained in Example 15, Phenyl C1 region FIG. 31 is a 13C-NMR chart of the styrene-propylene random copolymer obtained in Example 17. Methine-methylene-methyl region FIG. 32 is a 13C-NMR chart of the styrene-propylene random copolymer obtained in Example 17. Phenyl C1 region FIG. 33 is a 13C-NMR chart of the styrene-propylene random copolymer obtained in Example 18. Methine-methylene-methyl region FIG. 34 is a 13C-NMR chart of the styrene-propylene random copolymer obtained in Example 18. Phenyl C1 region FIG. 35 is a 13C-NMR chart of the styrene polymer obtained in Example 19.

Figure 36:
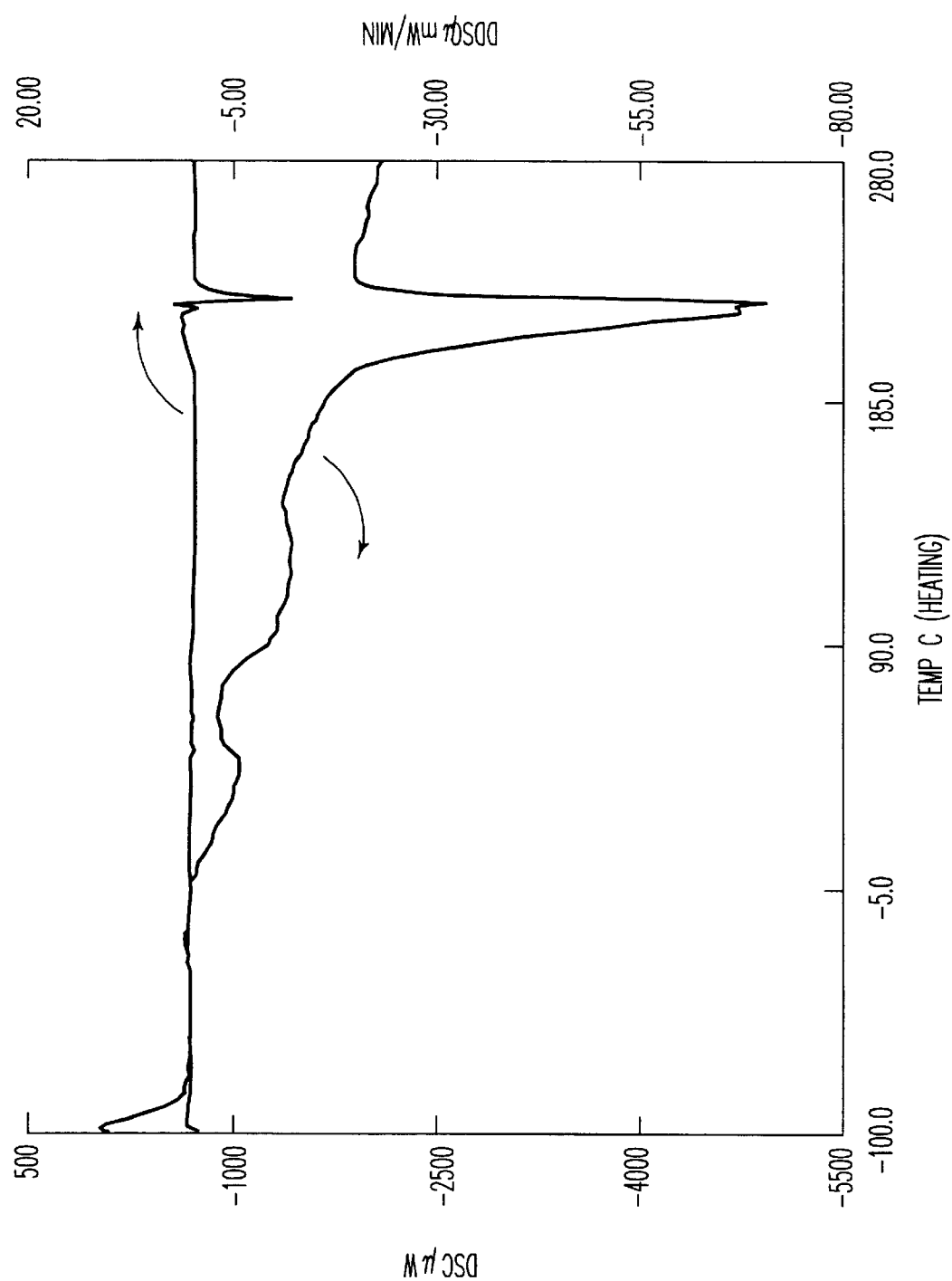

FIG. 36 is a DSC chart of the styrene polymer obtained in Example 19.

Figure 37:
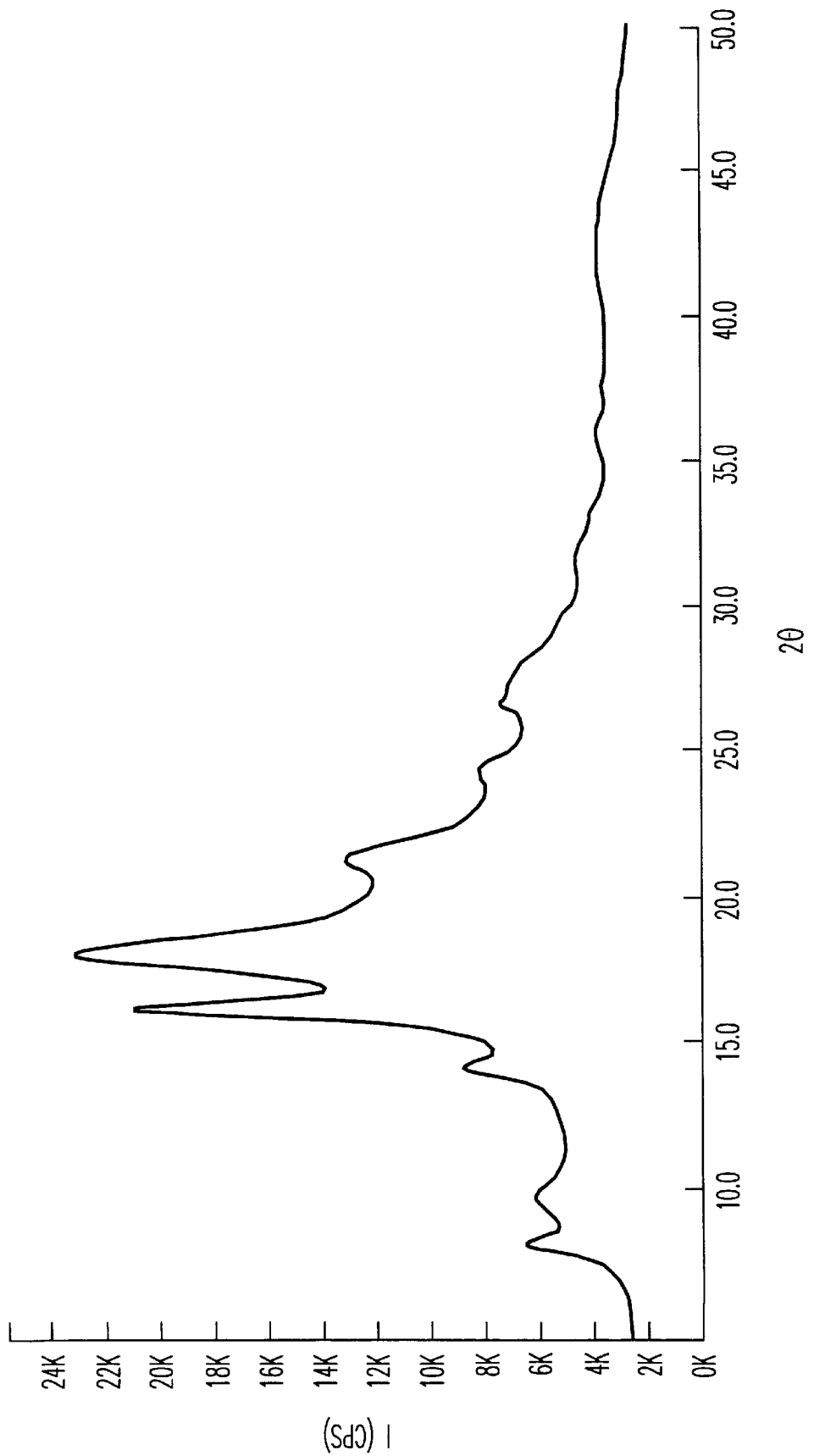

FIG. 37 is an X-ray diffraction pattern of the styrene polymer obtained in Example 19.

Figure 38:
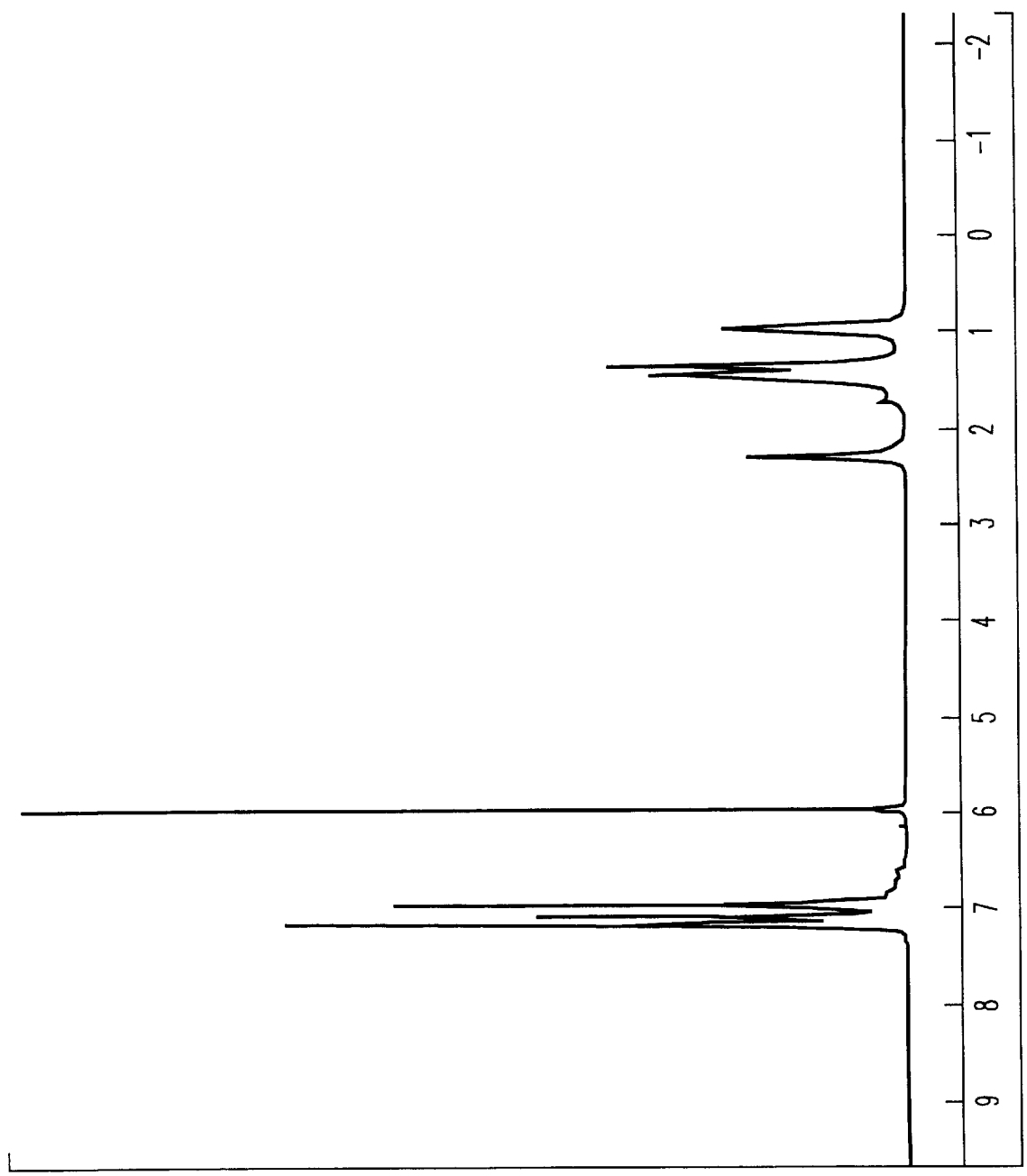

FIG. 38 is a 1H-NMR spectrum of the styrene-ethylene alternating copolymer obtained in Example 21.

Figure 39:
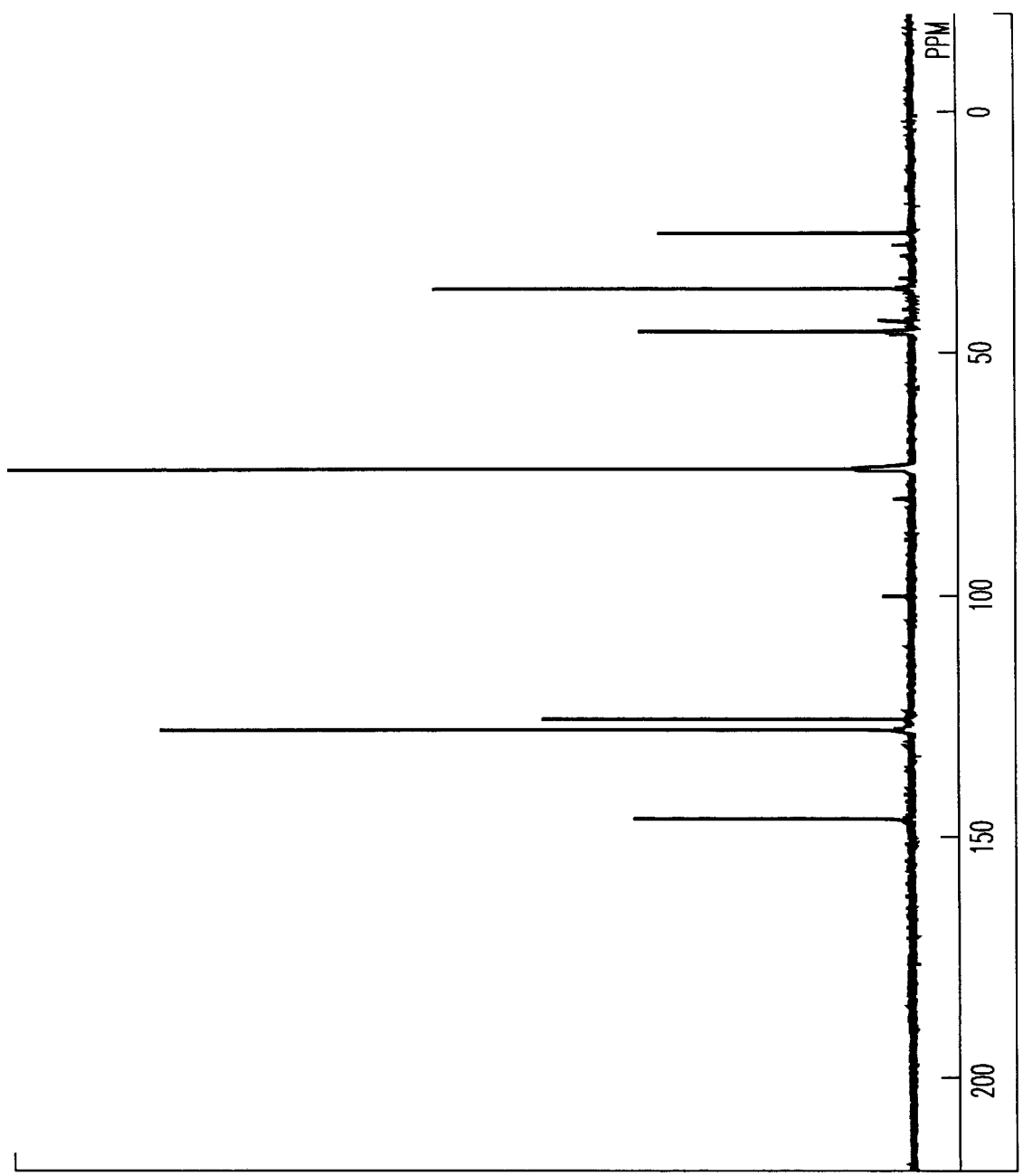
Figure 40:
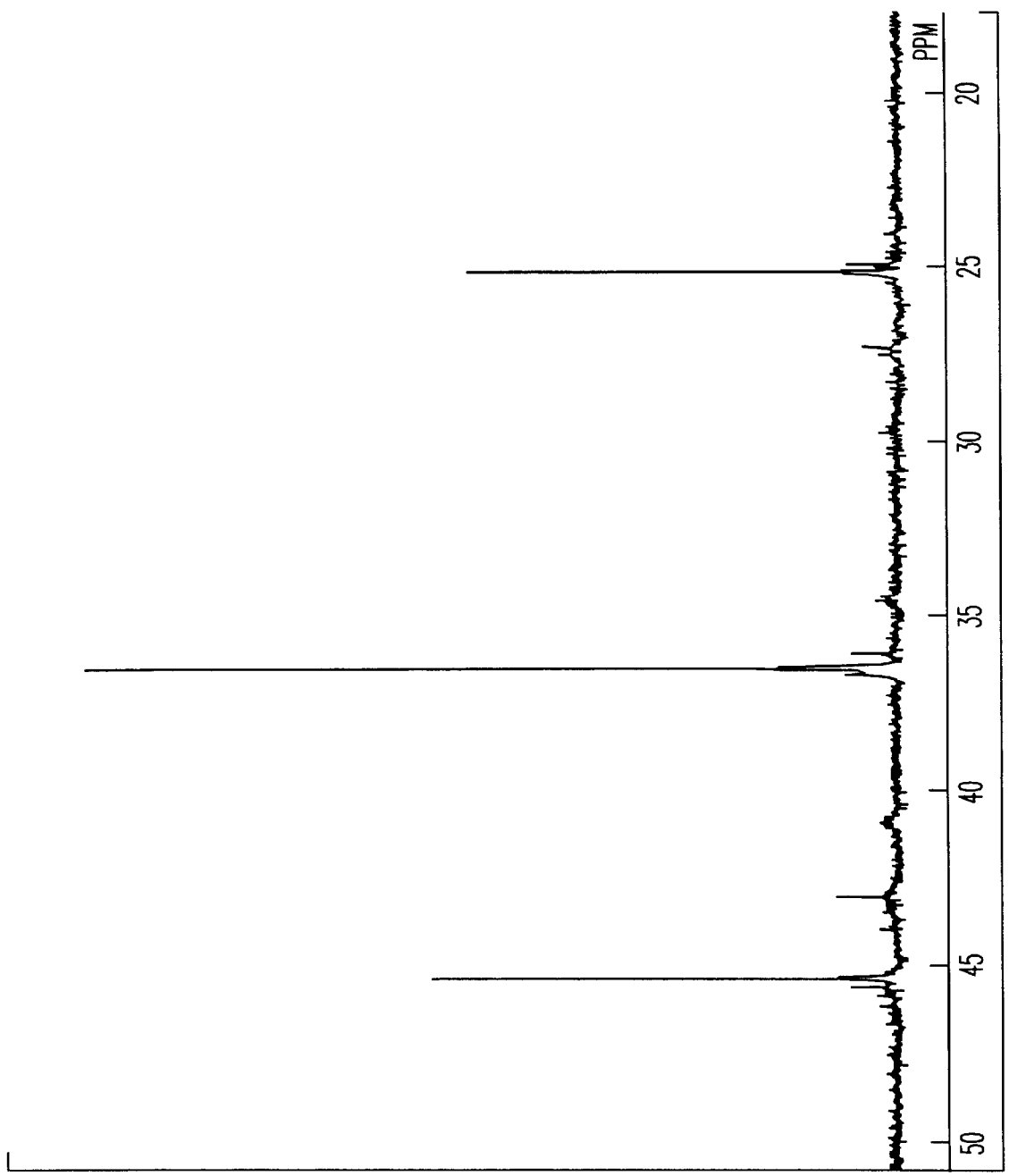
Figure 41B:
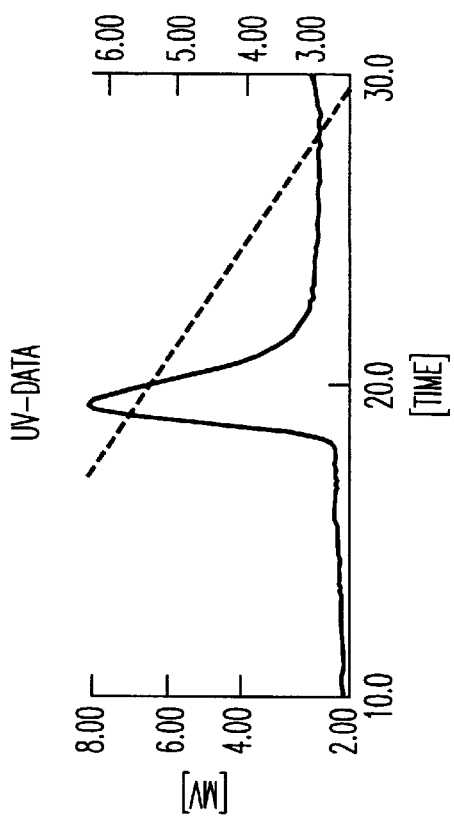
Figure 41A:
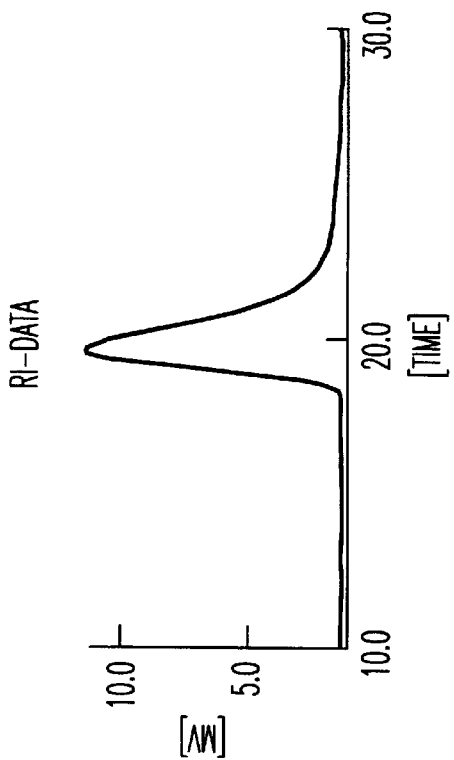

FIG. 39 is a 13C-NMR spectrum of the styrene-ethylene alternating copolymer obtained in Example 21. Entire spectrum FIG. 40 is a 13C-NMR spectrum of the styrene-ethylene alternating copolymer obtained in Example 21. Methine-methylene region FIG. 41 is a GPC chart of the styrene-ethylene alternating copolymer obtained in Example 21.

Figure 42:
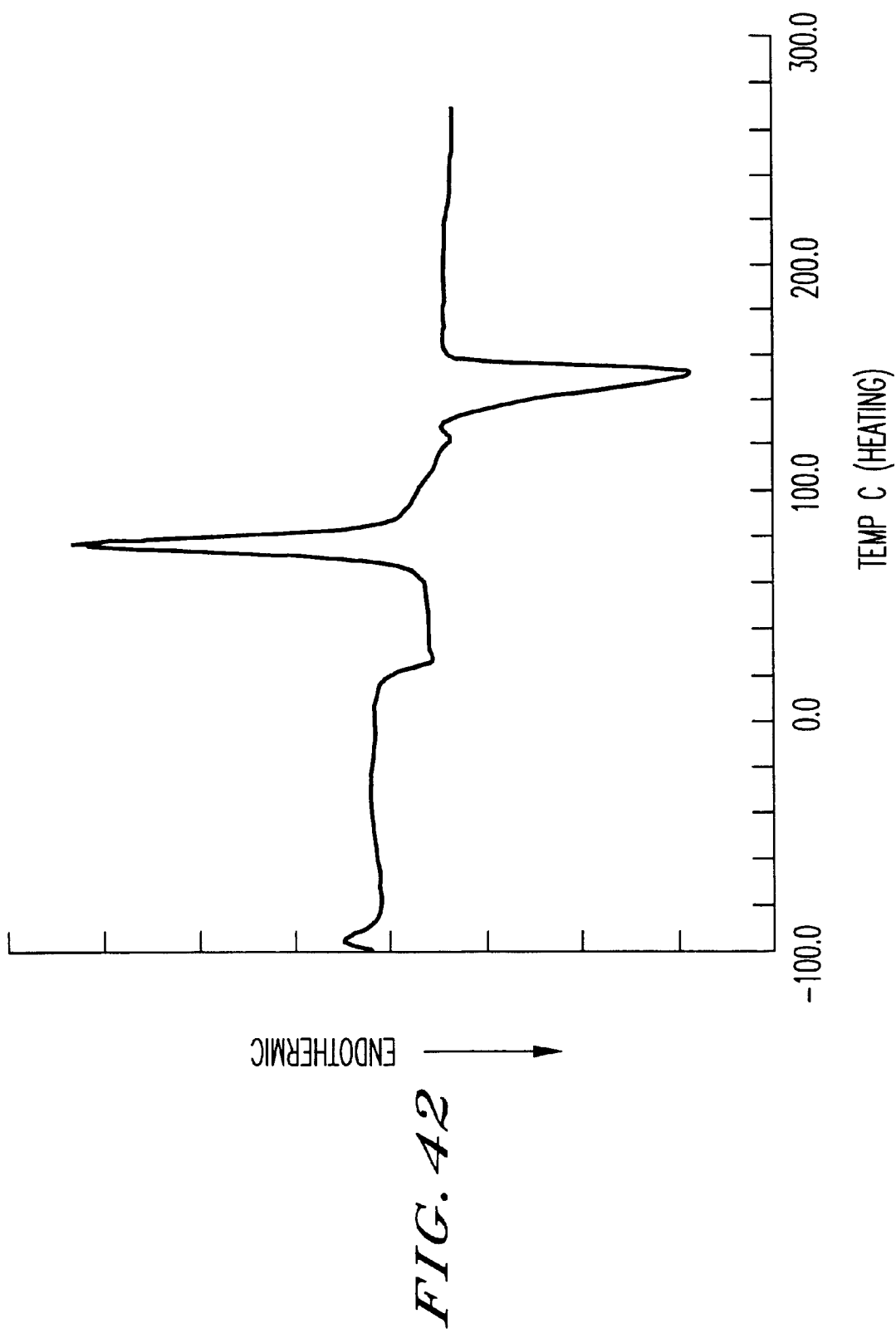

FIG. 42 is a DSC chart of the styrene-ethylene alternating copolymer obtained in Example 22.

Figure 43:
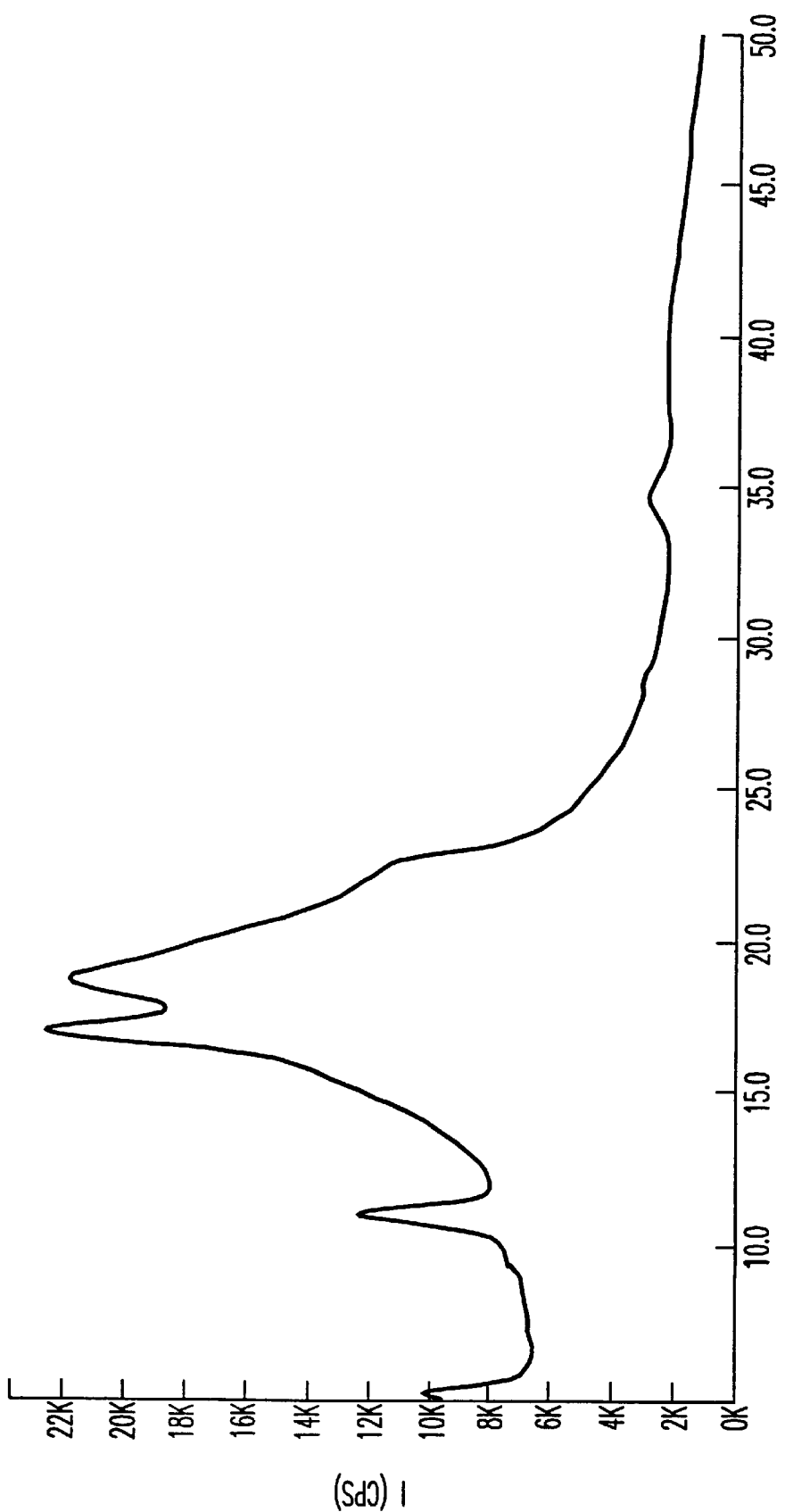

FIG. 43 is an X-ray diffraction pattern of the styrene-ethylene alternating copolymer obtained in Example 21.

Figure 44:
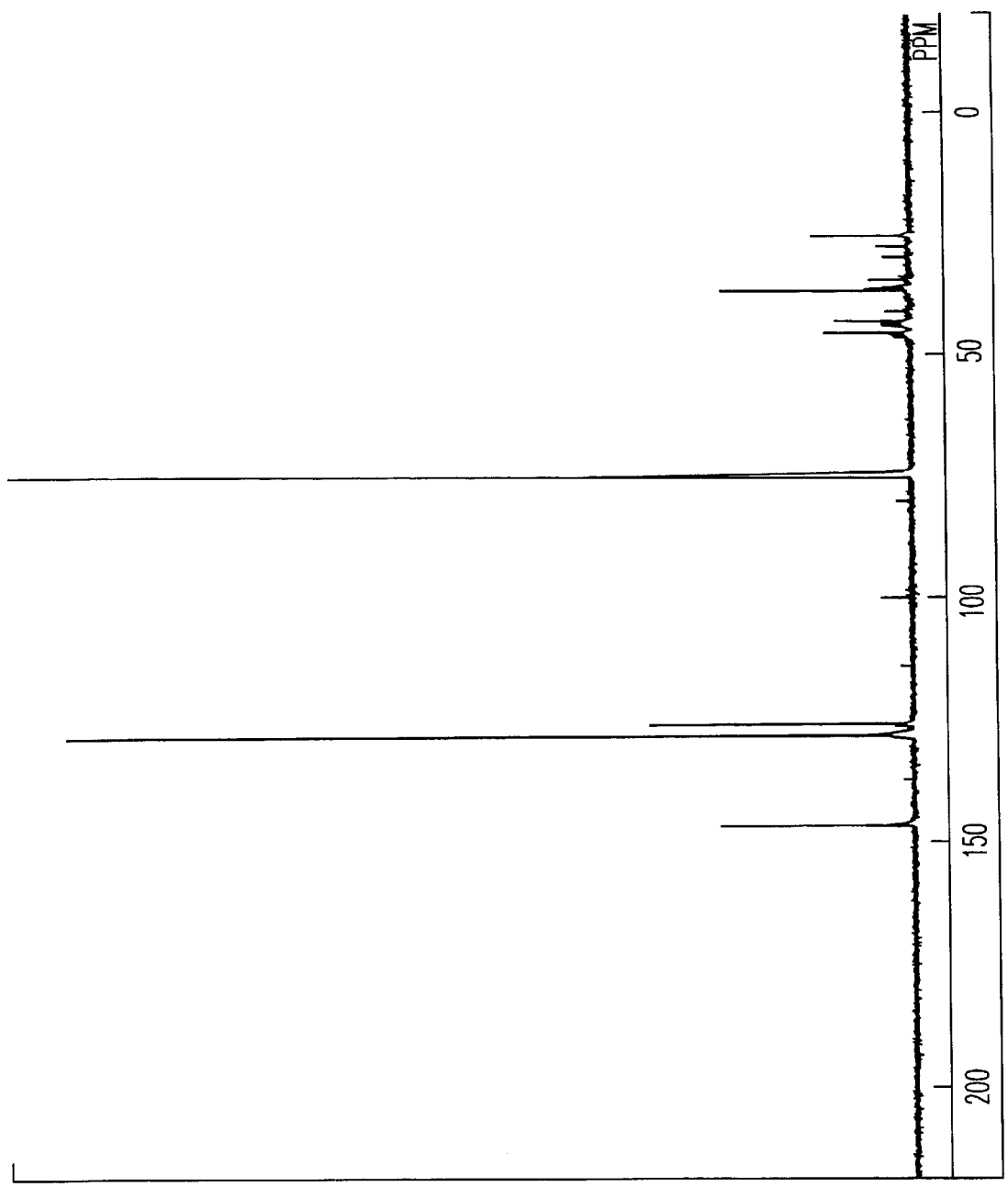
Figure 45:
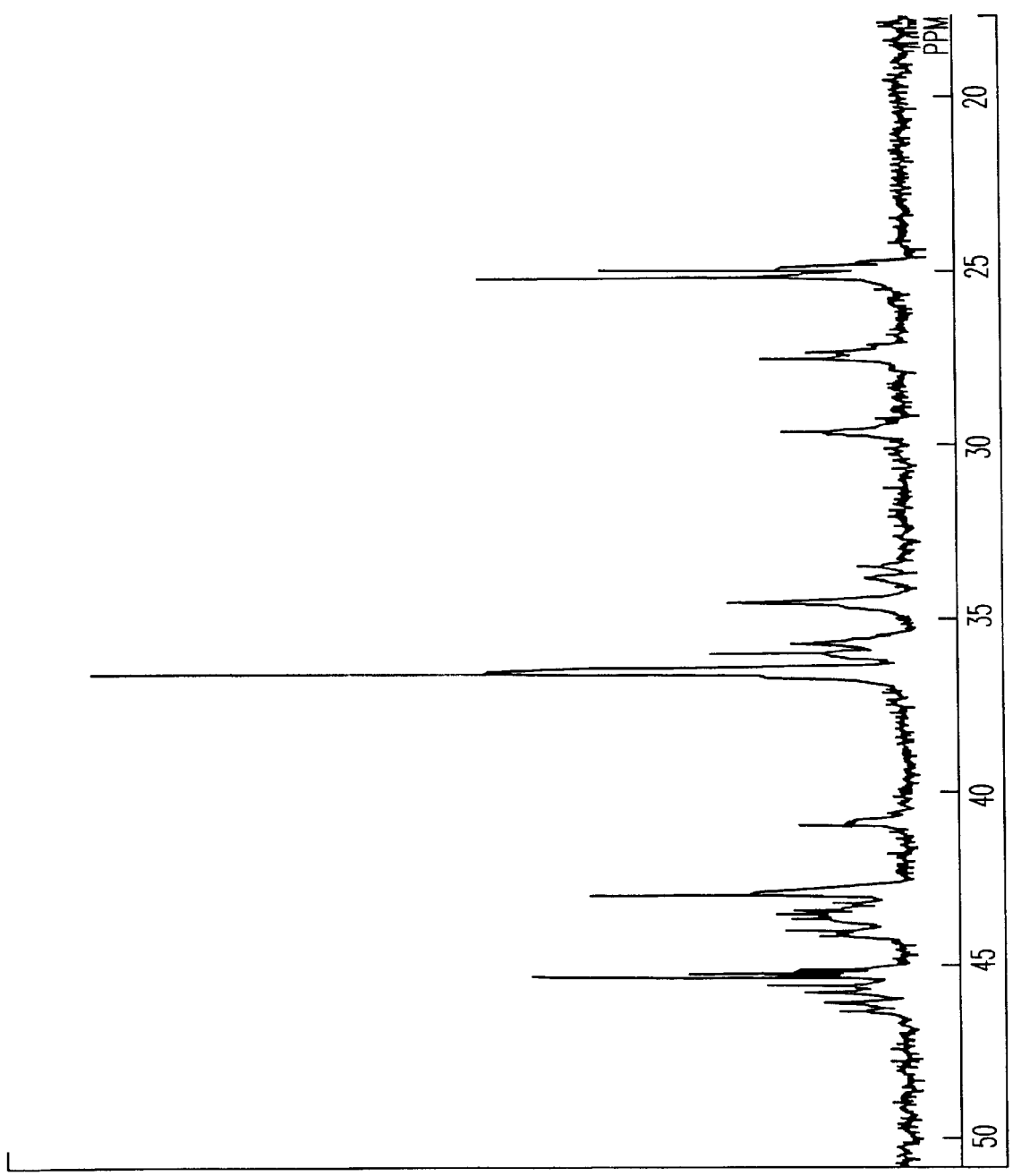
Figure 46:
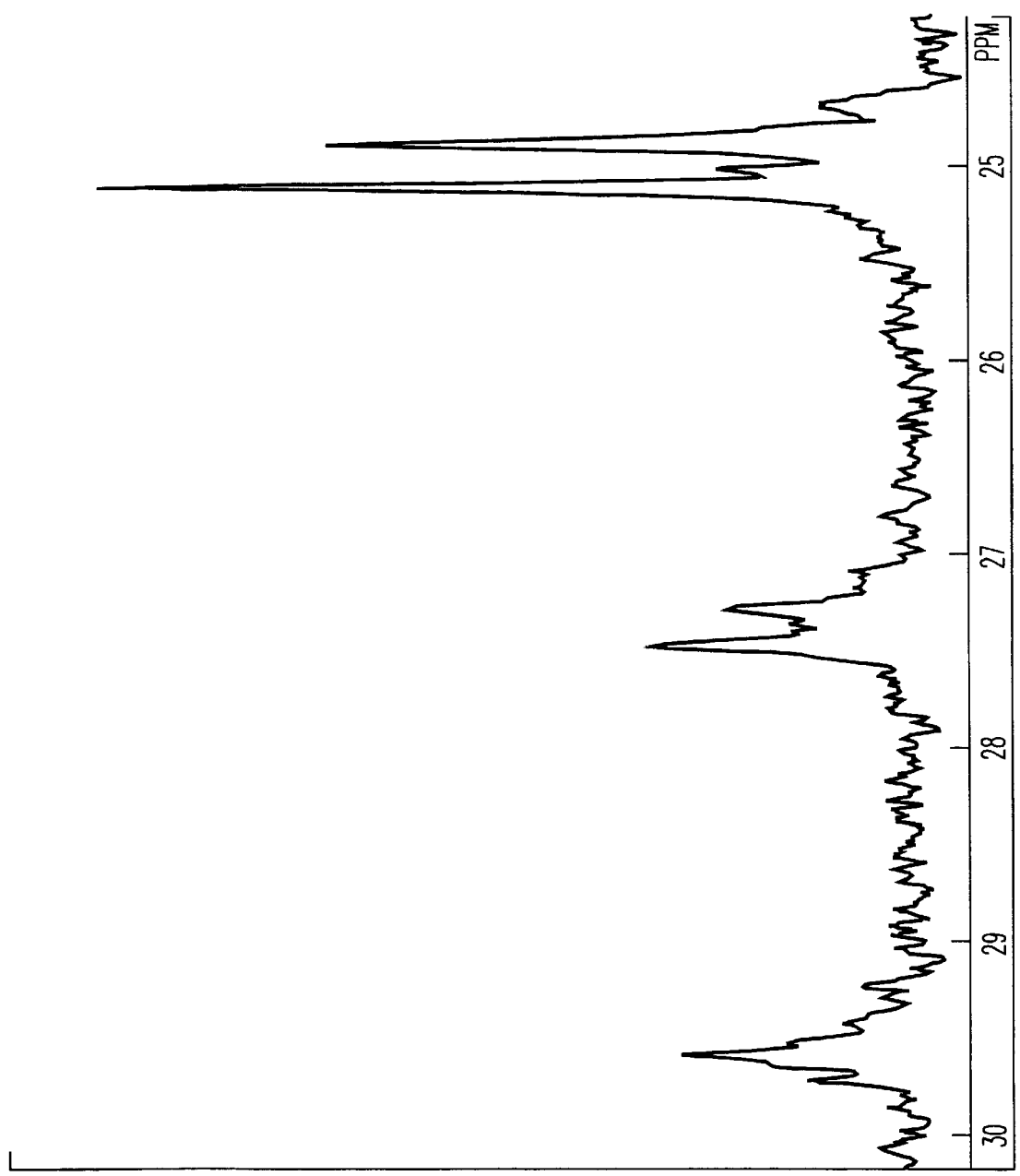

FIG. 44 is a 13C-NMR spectrum of the styrene-ethylene random copolymer obtained in Example 23. Entire spectrum FIG. 45 is a 13C-NMR spectrum of the styrene-ethylene random copolymer obtained in Example 23. Methine-methylene region FIG. 46 is a 13C-NMR spectrum of the styrene-ethylene random copolymer obtained in Example 23. In the vicinity of 25 ppm.

Figure 47B:
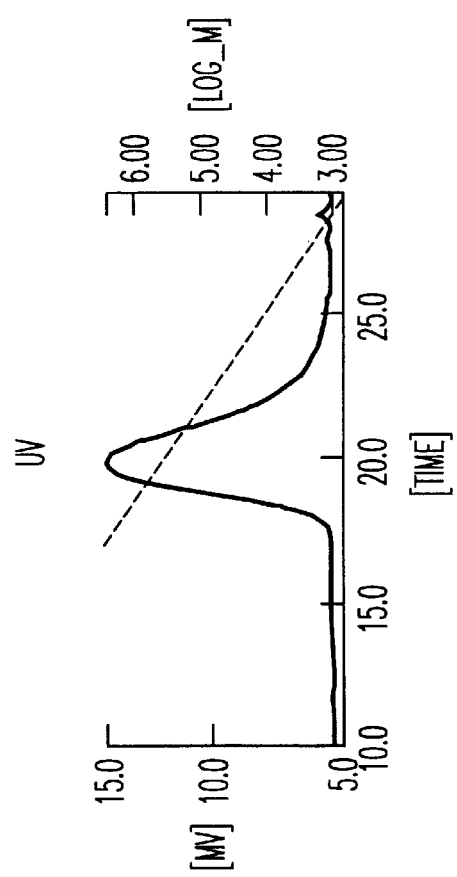
Figure 47A:
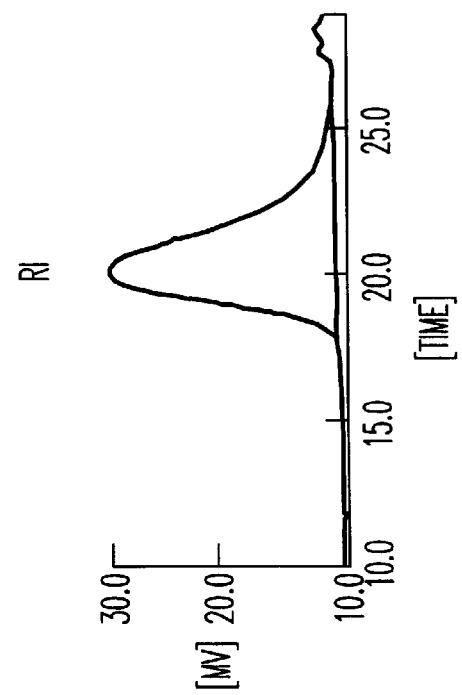

FIG. 47 is a GPC chart of the copolymer obtained in Example 25.

Figure 48:
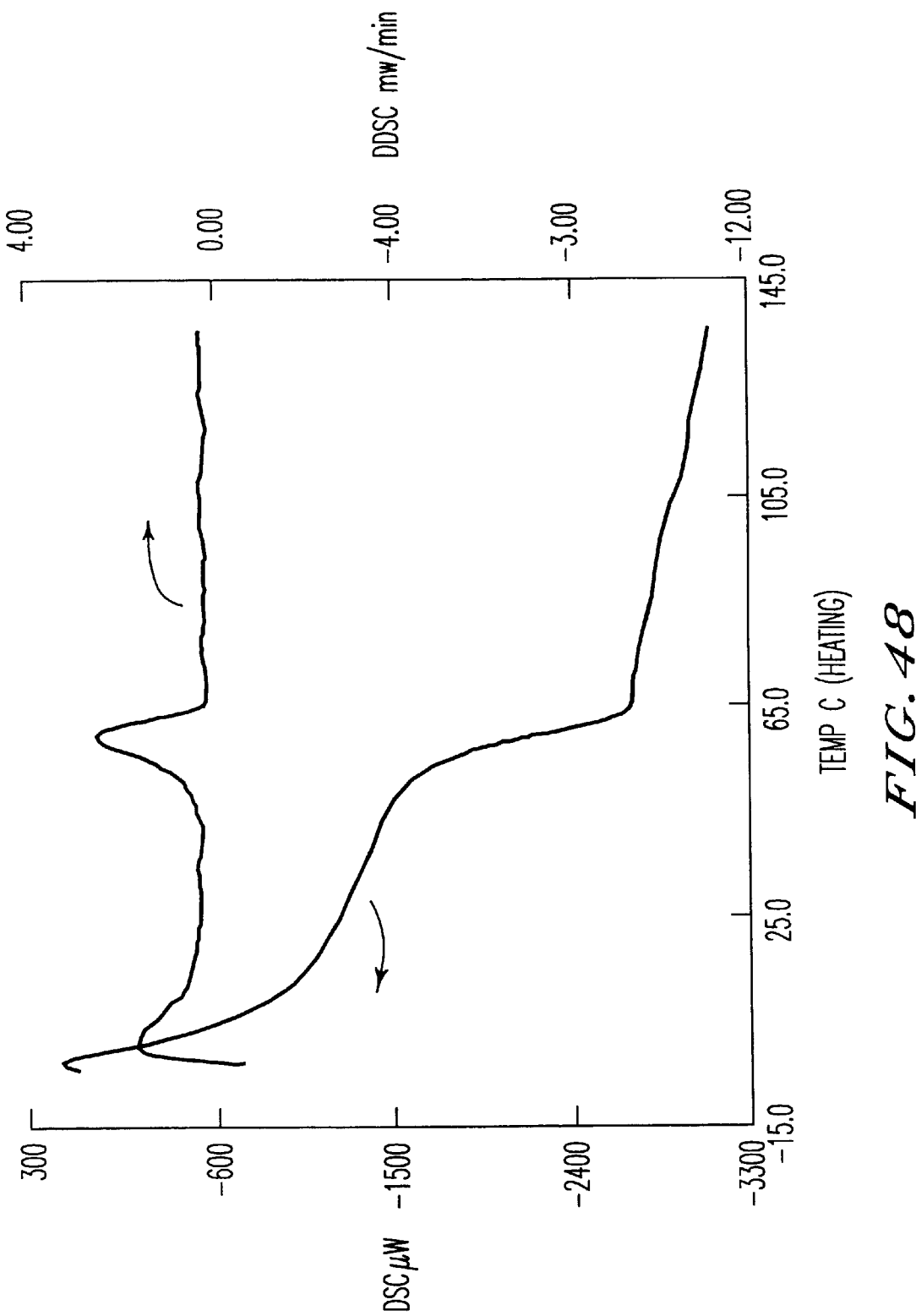

FIG. 48 is a DSC chart of the copolymer obtained in Example 25.

Figure 49:
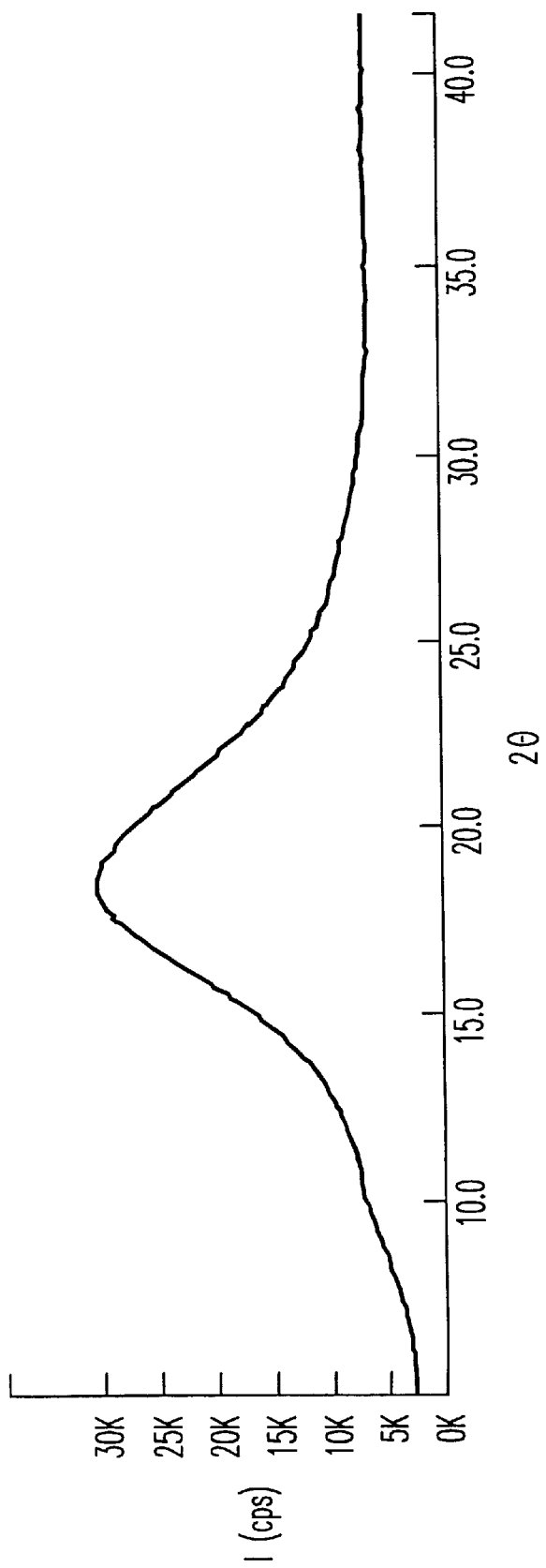

FIG. 49 is an X-ray diffraction pattern of the copolymer obtained in Example 25.

Figure 50:
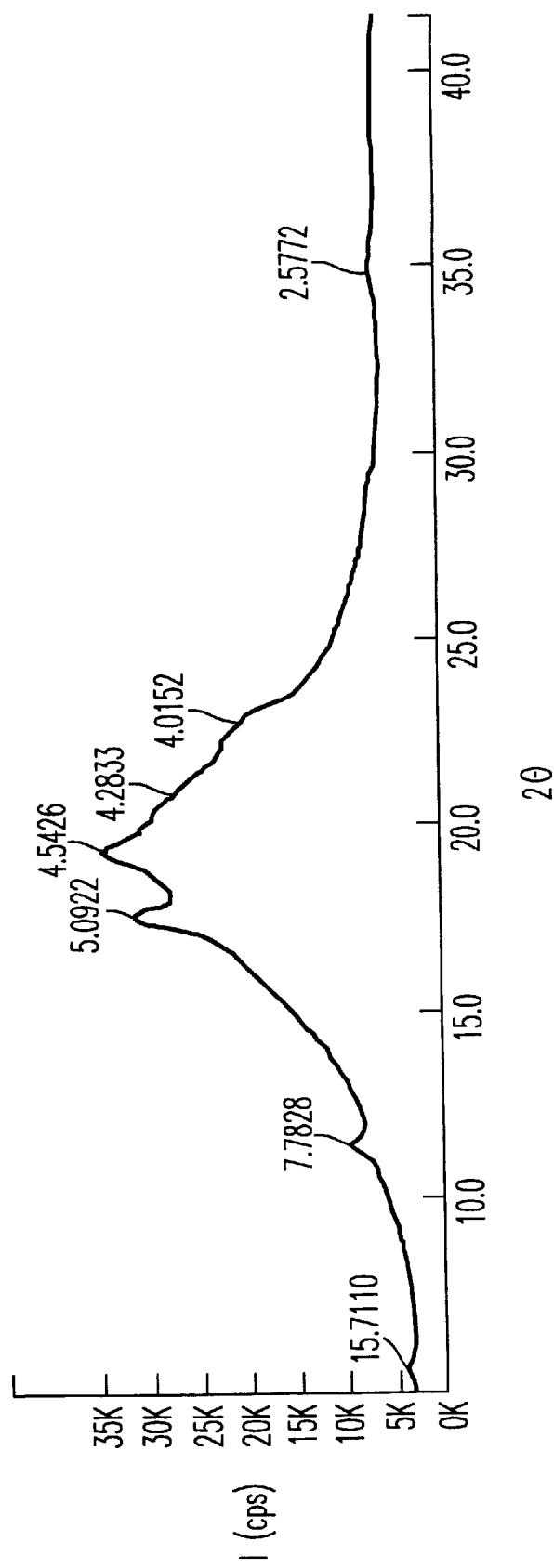

FIG. 50 is an X-ray diffraction pattern of a copolymer having a crystal structure derived from ethylene-styrene alternating structure.

Figure 51:
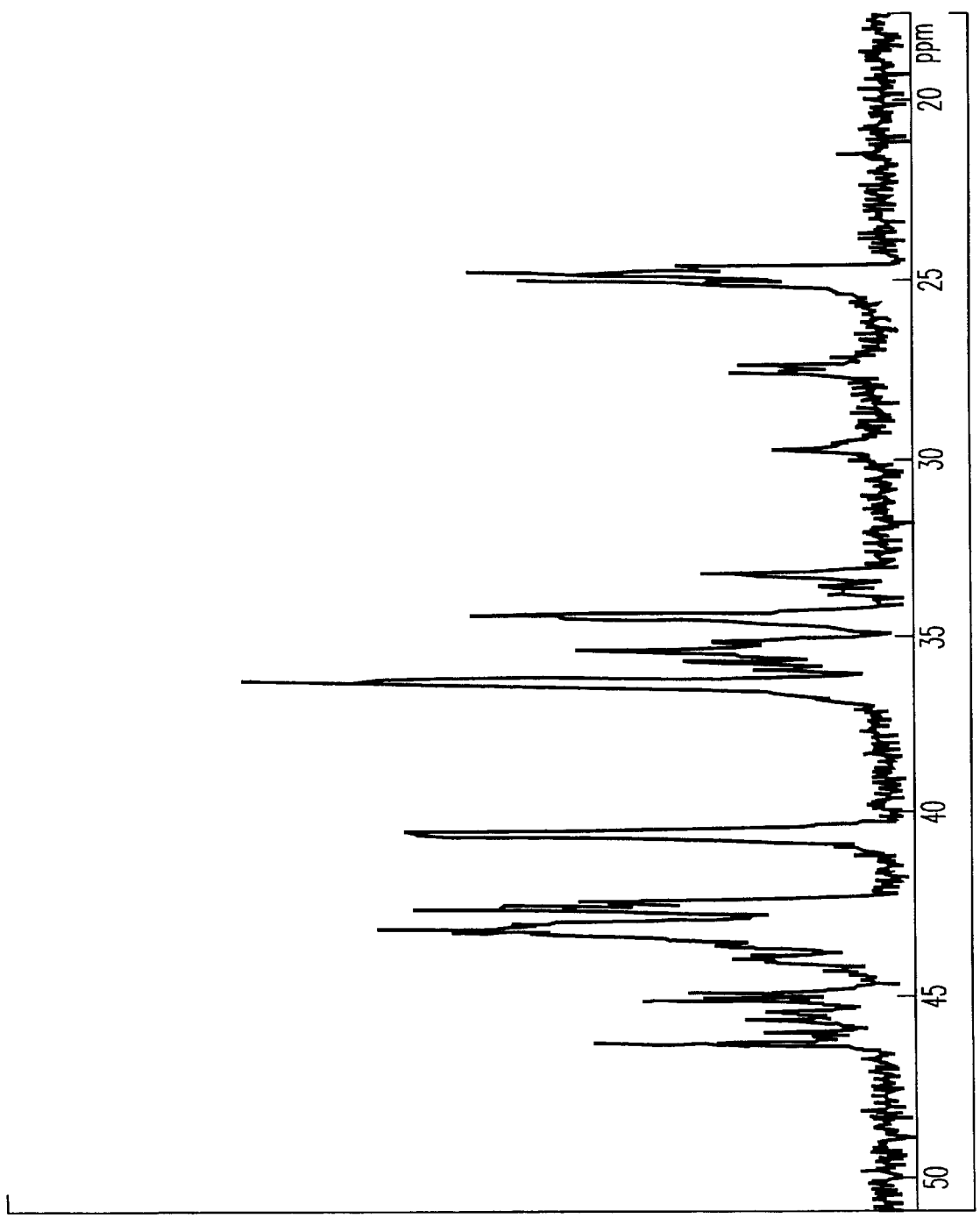

FIG. 51 is 13C-NMR spectrum (methine-methylene zone) of the copolymer obtained in Example 26.

Figure 52:
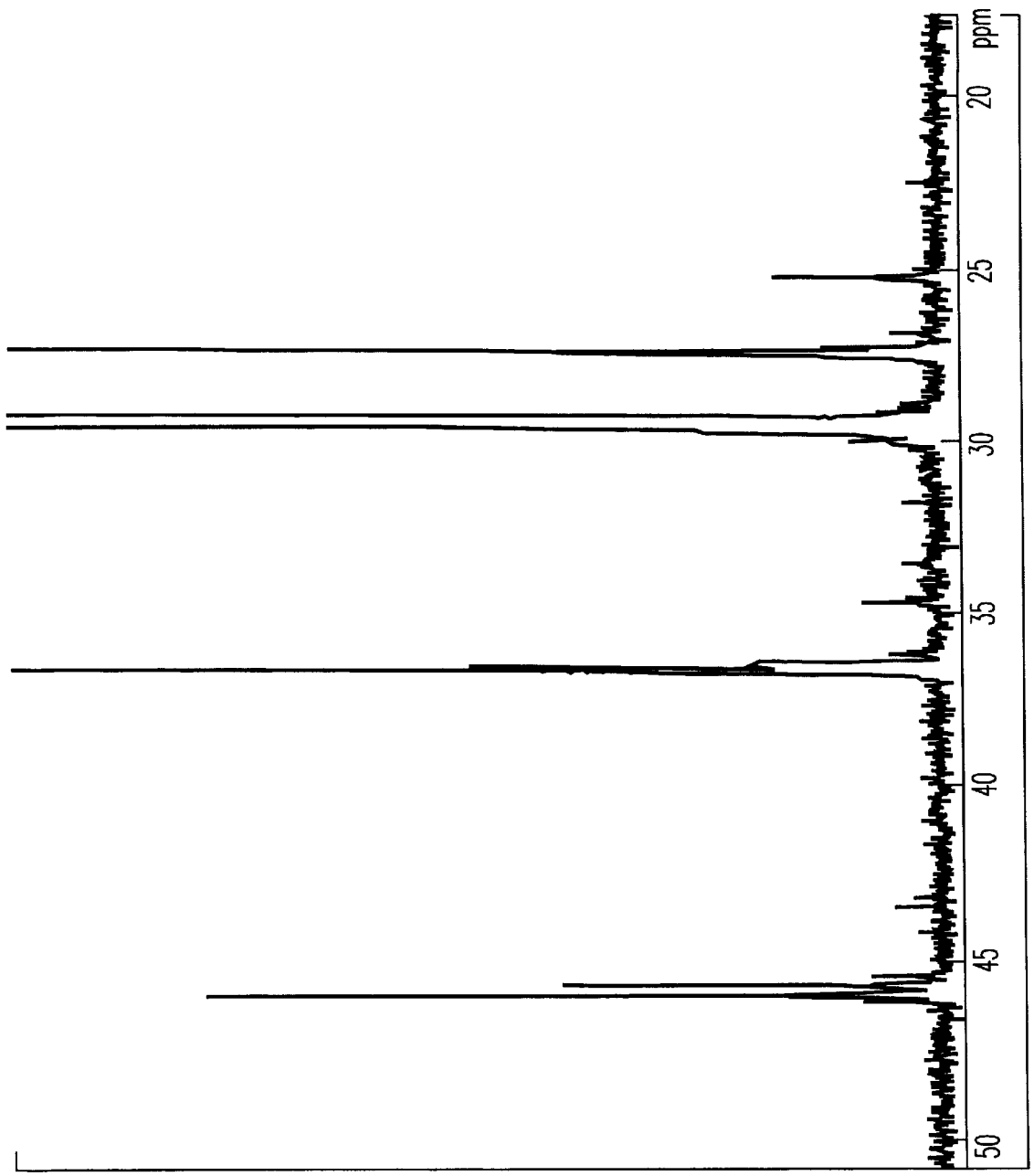

FIG. 52 is 13C-NMR spectrum (methine-methylene zone) of the copolymer obtained in Example 29.

The analyses of the copolymers obtained in the respective Examples and Comparative Examples were carried out by the following methods.

The 13C-NMR spectrum was measured using TMS as standard, by using α-500 manufactured by Nippon Denshi Kabushiki Kaisha and using a chloroform-d solvent or a 1,1,2,2-tetrachloroethane-d2 solvent. Here, the measurement using TMS as standard is the following measurement. Firstly, using TMS as standard, the shift value of the center peak of the triplet 13C-NMR peak of 1,1,2,2-tetrachloroethane-d2 was determined. Then, the copolymer was dissolved in the tetrachloroethane, and the 13C-NMR was measured, and each peak shift value was calculated using the triplet center peak of the tetrachloroethane as standard. The shift value of the triplet center peak of the tetrachloroethane was 73.89 ppm.

The 13C-NMR spectrum measurement for quantitative analysis of peak areas, was carried out by a proton gate decoupling method having NOE erased, by using pulses with a pulse width of 45° and a repeating time of 5 seconds as standard.

When the measurement was carried out under the same conditions except that the repeating time was changed to 1.5 seconds, the measured values of peak areas of the copolymer agreed to the values obtained in the case where the repeating time was 5 seconds, within a measurement error range.

The styrene content in the copolymer was determined by 1H-NMR. As the apparatus, α-500 manufactured by Nippon Denshi Kabushiki Kaisha and AC-250 manufactured by BRUKER Co. were used. The determination was made by comparing the intensity of the peak (6.5 to 7.5 ppm) attributable to the proton of a phenyl group and the proton peak (0.8 to 3 ppm) attributable to a methylene, methine and methyl group, measured by using TMS as standard and chloroform-d or 1,1,2,2-tetrachloroethane-d2 as a solvent.

The molecular weights in Examples are obtained by CPC (gel permeation chromatography) as calculated as standard polystyrene.

A copolymer soluble in THF at room temperature, was measured by means of HLC-8020, manufactured by TOSOH CORPORATION using THF as a solvents A copolymer insoluble in THF at room temperature, was measured at 135° C. by means of 150CV apparatus manufactured by Waters Co. and using 1,2,4-trichlorobenzene as a solvent, or measured at 145° C. by means of HLC-8121 apparatus manufactured by TOSOR CORPORATION using o-chlorobenzene as a solvent.

The DSC measurement was carried out by using DSC200, manufactured by Seiko Denshi K.K. in a nitrogen stream at a temperature raising rate of 10° C./min.

The X-ray diffraction was measured by means of MXP-18 model high power X-ray diffraction apparatus, source Cu rotating anode (wavelength: 1.5405 Å), manufactured by Mac Science Company.

TEST EXAMPLES

Preparation A of Transition Metal Compound

Rac-dimethylmethylenebis(4,5-benz-1-indenyl) zirconium dichloride (another name: rac-isopropylidenebis (4,5-benz-1-indenyl)zirconium dichloride, hereinafter referred to as rac{BInd-C(Me)$_2$-Bind}ZrCl$_2$) of the following formula was prepared by the following method.

4,5-Benzindene was prepared in accordance with Organometallics, 13, 964 (1994).

A-1 Preparation of 1,1-isopropylidene-4,5-benzindene

Preparation of 1,1-isopropylidene-4,5-benzindene was carried out with reference to the preparation of 6,6-diphenylfulvene disclosed in Can, J. Chem. 62, 1751 (1984), However, as starting materials, acetone was used instead of benzphenone, and 4,5-benzindene was used instead of cyclopentadiene.

A-2 Preparation of isopropylidenebis 4,5-benz-1-indene

In an Ar atmosphere, 21 mol of 4,5-benzindene was dissolved in 70 ml of THF, and an equivalent amount of BuLi was added thereto at 0° C., followed by stirring for 3 hours. THF having 21 mmol of 1,1-isopropylidene-4,5-benzindene dissolved therein, was added thereto, followed by stirring at room temperature overnight. Then, 100 ml of water and 150 ml of diethyl ether were added thereto, followed by shaking, and the organic layer was separated and washed with a saturated sodium chloride aqueous solution and then dried over sodium sulfate. The solvent was distilled off under reduced pressure. The obtained yellow solid was washed with hexane and dried to obtain 3.6 g of isopropylidenebis 4,5-benz-1-indene. The yield was 46%.

From the 1H-NMR spectrum measurement, it was found to have peaks at 7.2–8.0 ppm (m,12H), 6.65 ppm (2H), 3.75 ppm (4H), and 1.84 ppm (6H).

The measurement was carried out using TMS as standard and $CDCl_3$ as a solvent.

A-3 Preparation of rac-dimethylmethylenebis(4,5-benz-1-indenyl)zirconium dichloride In an Ar atmosphere, 7.6 mmol of isopropylidenebis 4,5-benz-1-indene and 7.2 mmol of zirconium tetrakisdimethylamide ($Zr(NMe_2)_4$) were charged together with 50 ml of toluene, followed by stirring at 130° C. for 10 hours. Toluene was distilled off under reduced pressure, and 100 ml of methylene chloride was added thereto, and the mixture was cooled to −78° C. Then, 14.4 mmol of dimethylamine hydrochloride was slowly added thereto, and the temperature was slowly raised to room temperature, followed by stirring for 2 hours, After distilling off the solvent, the obtained solid was washed with pentane and then with a small amount of THF to obtain 0.84 g of rac-dimethylmethylenebis(4,5-benz-1-indenyl)zirconium dichloride of yellow orange color of the following formula. The yield was 21%.

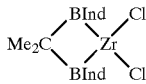

From the 1H-NMR spectrum measurement, it was found to have peaks at 8.01 ppm (m,2H), 7.75 ppm (m,2H) , 7.69 ppm (d,2H), 7.48–7.58 ppm (m,4H), 7.38 ppm (d,2H), 7.19 ppm (d,2H), 6.26 ppm (d,2H) and 2.42 ppm (s,6H).

The measurement was carried out using TMS as standard and $CDCl_3$ as a solvent.

The elemental analysis was carried out by elemental analysis apparatus 1108 model (manufactured by Fysons Co., Italy), whereby the results being C63.86% and H3.98% were obtained. The theoretical values were C65.39% and H4.16%.

Preparation B of Transition Metal Compound as Catalyst Component

Rac-dimethylmethylene(1-indenyl)(4,5-benz-1-indenyl)zirconium dichloride (another name: rac-isopropylidene(1-indenyl)(4,5-benz-1-indenyl) zirconium dichloride, hereinafter referred to as rac{Ind-C(Me)$_2$-BInd}ZrCl$_2$) was prepared by the following method.

B-1 Preparation of isopropylidene(1-indene)(4,5-benz-1-indene)

In an Ar atmosphere, 14 mmol of indene was dissolved in 50 ml of THF, and an equivalent amount of BuLi was added at 0° C., followed by stirring for 10 hours. Then, 10 ml of THF having 13 mmol of 1,1-isopropylidene-4,5-benzindene dissolved therein, was added thereto, followed by stirring at room temperature overnight. Then, 50 ml of water and 100 ml of diethyl ether were added, followed by shaking, and the organic layer was separated, washed with a saturated sodium chloride aqueous solution and dried over sodium sulfate. Then, the solvent was distilled off under reduced pressure. The residue was further purified by column chromatography to obtain 2.5 g of isopropylidene (1-indene)(4,5-benz-1-indene). The yield was 59%.

B-2 Preparation of rac-dimethylmethylene(1-indenyl)(4,5-benz-1-indenyl)zirconium dichloride In an Ar atmosphere, 6.5 mmol of isopropylidene (1-indene)(4,5-benz-1-indene) and 6.5 mmol of zirconium tetrakisdimethylamide {$Zr(NMe_2)_4$} were charged together with 40 ml of toluene, followed by stirring at 130° C. for 10 hours. Then, toluene was distilled off under reduced pressure, and 100 ml of methylene chloride was added thereto, and the mixture was cooled to −78° C. Then, 13 mmol of dimethylamine hydrochloride was slowly added thereto, and the temperature was slowly raised to room temperature, followed by stirring for 2 hours. Then, the solvent was distilled off, and the obtained solid was washed with pentane and then with a small amount of methylene chloride to obtain 0.76 g of rac-dimethylmethylene(1-indenyl)(4,5-benz-1-indenyl)zirconium dichloride of orange color. The yield was 24%. From the 1H-NMR spectrum measurement, it was found to have peaks at 7.05–8.04 ppm (m,10H) (provided a peak at 7.17 ppm is excluded), 7.17 ppm (d,H), 6.73 ppm (d,H), 6.25 ppm (d,H), 6.18 ppm (d,H), 2.41 ppm (m,3H), and 2.37 ppm (m,3H).

The measurement was carried out using TMS as standard and $CDCl_3$ as a solvent.

Preparation C of Transition Metal Compound as Catalyst Component

Rac-dimethylmethylenebis(4,5-benz-1-indenyl) zirconiumbisdimethylamide (another name: rac-isopropylidenebis(4,5-benz-1-indenyl) zirconiumbisdimethylamide, hereinafter referred to as rac{BInd-CMe$_2$-BInd}Zr(NMe$_2$)$_2$) of the following formula and meso-dimethylmethylenebis(4,5-benz-1-indenyl) zirconiumbisdimethylamide (another name: meso-isopropylidenebis(4,5-benz-1-indenyl) zirconiumbisdimethylamide, hereinafter referred to as meso{BInd-CMe$_2$-BInd}Zr(NMe$_2$)$_2$) were prepared as follows.

Into a 50 ml three-necked flask, a ligand (0.47 g, 1.25 mmol) was introduced and dissolved in 30 ml of toluene. Then, Zr(NMe$_2$)$_4$ (0.334 g, 1.25 mmol) was added thereto, and the mixture was heated to 100° C. in an Ar stream and stirred for 3 days. The solvent was distilled off from the product, and the residue was washed with pentane to obtain a pale brown powder.

From the NMR measurement, it was found to be a mixture of a composition comprising 28% of a racemic-form, 13% of a meso-form and 59% of the ligand.

rac-form: $^1$H-NMR(C6D6, TMS) δ: 1.70(s,12H, NMe2), 1.77(s,6H, CMe2), 5.91(d,2H,BIndC5), 6.73(d,2H,BIndC5), 6.8–7.7(m,12H,aromatic)

meso-form: $^1$H-NMR(C6D6, TMS) δ: 0.75(s,6H,NMe2), 1.50(s,3H,CMe2), 2.03(s,3H,CMe2), 2.71(s,6H,NMe2), 5.55(d,2H,BIndC5), 6.61(d,2H,BIndC5), 6.8–7.7(m,12H, aromatic)

Preparation of Styrene-ethylene Random Copolymers

Example 1

Into an autoclave having a capacity of 120 ml and equipped with a magnetic stirrer, which was evacuated and then filled with ethylene, 10 ml of styrene and 8.4 μmol, based on Al atom, of methyl alumoxane (MMAO-3A, manufactured by TOSOH-AKZO K.K.) were charged.

While magnetically stirring at room temperature, 16 ml of a toluene solution containing 8.4 vmol of the catalyst obtained in "Preparation B of transition metal catalyst component", rac{BInd-C(Me)$_2$-Ind}ZrCl$_2$, and 0.84 mmol of triisobutylaluminum, was quickly charged by a syringe, and ethylene was immediately introduced to raise the pressure to a total pressure of 0.6 MPa (5 kg/cm$^2$G). In 4 minutes after charging the catalyst, the inner temperature rised to 46° C. by polymerization heat, but after 5 minutes, the temperature started to drop. While maintaining the pressure at a level of 5 kg/cm$^2$G, polymerization was carried out for 1 hour. The polymerization solution was put into a large excess amount of dilute hydrochloric acid/methanol liquid to precipitate the polymer, which was dried under vacuum at 78° C. for 8 hours, to obtain 5 g of the polymer.

Example 2

Polymerization was carried out by using an autoclave having a capacity of 10 lit. and equipped with a stirrer and a jacket for heating/cooling. 800 ml of dry toluene and 4,000 ml of dry styrene were charged, and the inner temperature was raised to 50° C., followed by stirring. About 100 l of nitrogen was used for bubbling to purge the interior of the system, and then 8.4 mmol of triisobutylaluminum and 84 mmol, based on Al, of methylalumoxane (MMAO-3A, manufactured by TOSOH-AKZO K.K.) were added thereto. Ethylene was immediately introduced, and after the pressure was stabilized at 0.2 MPa (1 kg/cm$^2$G), about 50 ml of a toluene solution containing 21 μmol of the catalyst obtained in "Preparation A of transition metal catalyst component", rac-dimethylmethylenebis(4,5-benz-1-indenyl)zirconium dichloride, and 0.84 mmol of triisobutylaluminum, was added to the autoclave from a catalyst tank installed above the autoclave. While maintaining the inner temperature at 50° C. and the pressure at 0.2 MPa, polymerization was carried out for 6 hours. After the polymerization, the obtained polymer solution was gradually put into vigorously stirred excess methanol to precipitate the formed polymer, which was dried under reduced pressure at 60° C. until no weight change was observed any longer, to obtain 1,000 g of the polymer.

Examples 3 to 9

Polymerization and post treatment were carried out in the same manner as in Example 2 under the conditions shown in Table 1 by using, as a catalyst, the catalyst obtained in "Preparation A of transition metal compound as catalyst component", rac-dimethylmethylenebis(4,5-benz-1-indenyl)zirconium dichloride.

However, in Example 7, methylalumoxane (PMAO, manufactured by TOSOH-AKZO K.K.) was used as a cocatalyst.

Further, in Examples 4 and 5, ethylene was diluted with nitrogen gas to lower the ethylene partial pressure, whereby polymerization was carried out.

Examples 10 and 11

Polymerization and post treatment were carried out in the same manner as in example 2 under the conditions shown in Table 1 by using, as a catalyst, the catalyst obtained in "Preparation B of transition metal catalyst component", rac-dimethylmethylene(1-indenyl)(4,5-benz-1-indenyl) zirconium dichloride.

Example 12

Polymerization and post treatment were carried out in the same manner as in Example 2 under the conditions shown in Table 1, except that the catalyst was changed to the complex mixture of rac-form and meso-form, obtained in "Preparation C of transition metal compound as catalyst component", which was weighed so that it contained 8.4 μmol of rac-dimethylmethylenebis(4,5-benz-1-indenyl)zirconiumbisdimethylamide, and used for polymerization.

Example 13

8.4 μmol of rac{BInd-C(Me)$_2$-Ind}ZrCl$_2$ obtained in "Preparation B of transition metal compound as catalyst component" was dissolved in 20 ml of a toluene solution containing 1 mmol of triisobutylaluminum. Then, 20 ml of a toluene solution having 8.4 μmol of Ph$_3$CB(C$_6$F$_5$)$_4$ dissolved therein, was added thereto to obtain a catalyst solution. Into an autoclave having a capacity of 1 lit. and equipped with a stirrer, 400 ml of toluene and 80 ml of styrene were charged, and the catalyst solution was introduced under an ethylene pressure of 10 kg/cm$^2$G) at an inner temperature of 17° C. Polymerization started immediately, and the inner temperature rised to the maximum of 74° C. by heat generation. Polymerization was carried out for one hour while maintaining the pressure at a level of 1.1 MPa (10 kg/cm$^2$G) during the polymerization. Post treatment was carried out in the same manner as in Example 2, to obtain 53 g of a polymer.

Example 14

Polymerization was carried out by using a polymerization reactor having a capacity of 150 lit. and equipped with a stirrer and a jacket for heating/cooling.

60 lit. of dry cyclohexane and 12 lit. of dry styrene were charged, and the inner temperature was raised to 33° C. with stirring. Then, 84 mmol of triisobutylaluminum and 840 mmol, based on Al, of methylalumoxane (MMAO-3A, manufactured by TOSOH-AKZO K.K.) were added thereto. Ethylene was immediately introduced, and after the pressure was stabilized at 1.0 MPa (9 kg/cm$^2$G), about 100 ml of a toluene solution containing 78 μmol of the catalyst obtained in "Preparation A of transition metal compound as catalyst component", rac-dimethylmethylenebis(4,5-benz-1-indenyl)zirconium dichloride, and 2 mmol of triisobutylaluminum, was added to the polymerization reactor from a catalyst tank installed above the polymerization tank. As heat generation started immediately, cooling water was introduced to the jacket. The inner temperature rose to the maximum of 80° C., but thereafter was maintained at about 70° C., and polymerization was carried out for 2.5 hours while maintaining the pressure at 1.0 MPa.

After completion of the polymerization, the obtained polymerization solution was deaerated and then treated by a crumb forming method as follows to recover the polymer.

The polymerization solution was put into 300 lit. of vigorously stirred water heated to 85° C. containing a dispersant (Pluronic, tradename) over one hour. Then, it was stirred at 97° C. for one hour, and then the hot water containing the crumb was put into cool water to recover the crumb. The crumb was dried in air at 50° C. and then deaerated under vacuum at 60° C. to obtain 12.8 kg of a polymer having a good crumb shape and having a size of about a few mm.

Comparative Example 1

With reference to J. Am. Chem. Soc., 110, 6255 (1988) and J. Organomet. Chem, 459, 117 (1993), EWEN type Zr complex, diphenylmethylene (fluorenyl)(cyclopentadienyl) zirconium dichloride of the following formula, another name: {Flu-CPh$_2$-Cp}ZrCl$_2$, was prepared.

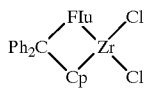

Into an autoclave having a capacity of 120 ml and equipped with a stirrer, which was substituted by nitrogen and then by ethylene, 20 ml of styrene and 4.6 mmol of methylalumoxane (MMAO-3A, manufactured by TOSOH-AKZO K.K.) were charged and heated to 40° C. While maintaining the ethylene pressure at atmospheric pressure, 46 μmol of the above {Flu-CPh$_2$-Cp}ZrCl$_2$ dissolved in 20 ml of toluene, was added, and polymerization was carried out for one hour. During the polymerization, the temperature was maintained to be 40° C., and the presser was maintained to be atmospheric pressure (0 kg/cm$^2$G). Post treatment after the polymerization was carried out in the same manner as in Example 1, to obtain 2.2 g of a white polymer.

Comparative Example 2

Polymerization and post treatment were carried out in the same manner as in Example 2 under the conditions shown in Table 1 by using the above diphenylmethylene (fluorenyl)(cyclopentadienyl)zirconium dichloride. From the amount of consumption of ethylene monitored, polymerization was found to be substantially completed in 4 hours.

Comparative Example 3

With reference to JP-A-7-053618, CGCT (constrained geometrical structure) type Ti complex, (tertiary butylamide)dimethyl(tetramethyl-η5-cyclopentadienyl) silanetitanium dichloride, another name; {CpMe$_4$-SiMe-NtBu}TiCl$_2$, was prepared.

Polymerization and post treatment were carried out in the same manner as in Example 2 under the conditions shown in Table 1 by using, as a complex, the CGCT (constrained geometrical structure) type Ti complex, (tertiary butylamide)dimethyl(tetramethyl-η5-cyclopentadienyl) silanetitanium dichloride. From the amount of consumption of ethylene monitored, polymerization was found to be substantially completed in 3 hours.

Comparative Examples 4 and 5

Polymerization and post treatment were carried out in the same manner as in Example 2 under the conditions shown in Table 1 by using, as a complex, the CGCT (constrained geometrical structure) type Ti complex, (tertiary butylamide) dimethyl (tetramethyl-η5-cyclopentadienyl) silanetitanium dichloride. From the amount of consumption of ethylene monitored, in both Comparative Examples 4 and 5, polymerization was found to be substantially completed in 2.5 hours.

Comparative Example 6

With reference to Organometallics, 13, 964 (1994), rac-dimethylsilylenebis(2-methyl-4,5-benzindenyl)zirconium dichloride, another name ras{2-Me-BInd-SiMe$_2$-2-Me-BInd}ZrCl$_2$, was prepared.

Polymerization and post treatment were carried out in the same manner as in Example 2 under the conditions shown in Table 1 by using, as a complex, dimethylsilylenebis(2-methyl-4,5-benzindenyl)zirconium dichloride. From the amount of consumption of ethylene monitored, the polymerization was found to be substantially completed in 2 hours.

Comparative Example 7

With reference to Angew. Chem. Int. Ed. Engl. 24, 507 (1985), rac-ethylenebis(1-indenyl)zirconium dichloride, another name: rac{Ind-Et-Ind}ZrCl$_2$, was prepared.

Polymerization and post treatment were carried out in the same manner as in Example 2 under the conditions shown in Table 1 by using, as a complex, rac-ethylenebis(1-indenyl) zirconium dichloride. From the amount of consumption of ethylene monitored, polymerization was found to be substantially completed in 6 hours.

Table 1 shows the copolymerization results.

Figure 1:
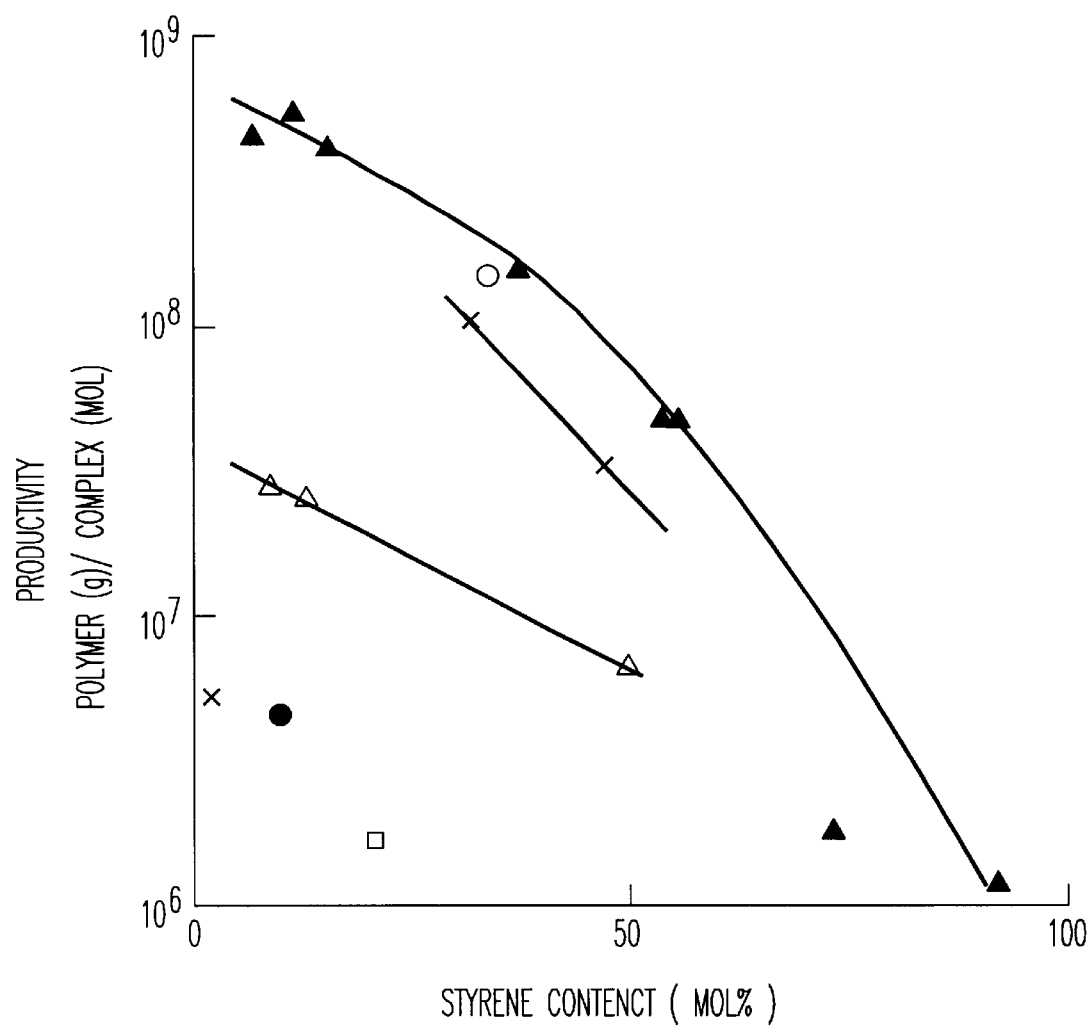
FIG. 1 is a graph showing the productivity of the polymer per catalyst in each Example or Comparative Example.

FIG. 1 shows the productivity of a polymer per catalyst in each Example or Comparative Example wherein polymerization was carried out by using a 10 lit. autoclave. It is evident that the catalysts in Examples exhibit remarkably high productivity as compared with the catalysts of Comparative Examples.

TABLE 1

| Examples | Catalyst | Amount of catalyst (μmol) | Cocatalyst (μmol) MAO | Amount of solvent (ml) | Amount of styrene (ml) | Ethylene pressure MPa | PTE (° C.) | PTI (hr) | Yield (g) | Productivity (g/mol-catalyst)/10$^6$ | St content (mol %) (%) |
|---|---|---|---|---|---|---|---|---|---|---|---|
| Ex. 1 | B | 8.4 | 8.4 | T 26 | 10 | 0.6 | 15–46 | 1 | 5 | 0.49 | 41.0 |
| Ex. 2 | A | 21 | 84 | T 800 | 4000 | 0.2 | 50 | 6 | 1000 | 47.6 | 53.8 |
| Ex. 3 | A | 21 | 84 | T 800 | 4000 | 0.15 | 50 | 8 | 1013 | 48.2 | 55.5 |
| Ex. 4 | A | 84 | 84 | T 800 | 4000 | 0.02 | 50 | 5 | 150 | 1.8 | 72.9 |
| Ex. 5 | A | 84 | 84 | T 800 | 4000 | 0.005 | 50 | 8 | 98 | 1.2 | 92.0 |
| Ex. 6 | A | 2.1 | 84 | T 4000 | 800 | 1.1 | 50 | 4 | 874 | 416 | 15.5 |
| Ex. 7 | A | 0.84 | 8.4 | T 4000 | 800 | 1.1 | 50 | 5 | 464 | 550 | 11.5 |
| Ex. 8 | A | 2.1 | 8.4 | T 4400 | 400 | 1.1 | 50 | 4 | 970 | 462 | 7.0 |
| Ex. 9 | A | 8.4 | 84 | T 2400 | 2400 | 1.1 | 50 | 5 | 1320 | 157 | 37.1 |
| Ex. 10 | B | 21 | 84 | T 800 | 4000 | 0.2 | 50 | 6 | 700 | 33.3 | 47.1 |
| Ex. 11 | D | 8.4 | 84 | T 2400 | 2400 | 1.1 | 50 | 5 | 870 | 104 | 31.8 |
| Ex. 12 | C | 8.4 | 84 | T 2400 | 2400 | 1.1 | 50 | 2.5 | 1280 | 152 | 33.9 |
| Ex. 13 | B | 8.4 | 0.0084* | T 400 | 80 | 1.1 | 17–74 | 1 | 53 | 6.3 | 25.8 |
| Ex. 14 | A | 78 | 840 | C 60L | 12L | 1.0 | 33–81 | 2.5 | 12.8kg | 164 | 27.9 |
| Comp. Ex. 1 | D | 46 | 4.6 | T 20 | 20 | 0.1 | 40 | 1 | 2.2 | 0.05 | 43.0 |

TABLE 1-continued

| Examples | Catalyst | Amount of catalyst (μmol) | Cocatalyst (μmol) MAO | Amount of solvent (ml) | Amount of styrene (ml) | Ethylene pressure MPa | PTE (° C.) | PTI (hr) | Yield (g) | Productivity (g/mol-catalyst)/10^b | St content (mol %) (%) |
|---|---|---|---|---|---|---|---|---|---|---|---|
| Comp. Ex. 2 | D | 164 | 164 | T 800 | 4000 | 0.4 | 50 | 4 | 286 | 1.7 | 21.1 |
| Comp. Ex. 3 | E | 84 | 84 | T 800 | 4000 | 0.2 | 50 | 3 | 570 | 6.8 | 49.8 |
| Comp. Ex. 4 | E | 21 | 84 | T 3300 | 1500 | 1.1 | 50 | 2.5 | 550 | 26.2 | 13.0 |
| Comp. Ex. 5 | E | 2.1 | 84 | T 3500 | 1300 | 1.1 | 50 | 2.5 | 60 | 28.8 | 9.0 |
| Comp. Ex. 6 | F | 8.4 | 84 | T 4000 | 800 | 1.1 | 50 | 2 | 44 | 5.2 | <2 |
| Comp. Ex. 7 | C | 84 | 84 | T 800 | 4000 | 0.2 | 50 | 6 | 385 | 4.6 | 9.5 |

T: Toluene    C: Cyclohexane
Transition metal compounds used as catalysts
A: rac-dimethylmethylenebis (4,5-benz-1-indenyl) zirconium dichloride
B: rac-dimethylmethylene(1-indenyl) (4,5-benz-1-indenyl) zirconium dichloride
C: rac-dimethylmethylenebis (4,5-benz-1-indenyl) zirconium bis (dimethylamide)
D: Diphenylmethylene(cyclopentadienyl) (fluorenyl) zirconium dichloride
E: Tertiary butylamide dimethyl (tetramethyl-η5-cyclopentadienyl)silanetitanium dichloride
F: rac-dimethylsilylenebis (2-methyl-4,5-benz-1-indenyl)zirconium dichloride
G: rac-ethylenebis(1-indenyl)zirconium dichloride
*: Ph3CB(C6F5)4 was used instead of MAO.
PTE: Polymerization temperature
PTI: Polymerization time Table 2 shows the styrene content, the molecular weight obtained by GPC, and the glass transition point and the melting point obtained by DSC, of the obtained polymer.

TABLE 2

| Examples | St content (mol %) | Mw /10^4 | Mn /10^4 | Mw/Mn | Glass transition temp. (° C.) | Melting point (° C.) |
|---|---|---|---|---|---|---|
| Ex. 1 | 41.0 | ✗22.1 6.8 | ✗13.2 1.5 | ✗1.7 4.5 | — | 79,130 |
| Ex. 2 | 53.8 | 24.6 | 12.6 | 2.0 | 25 | 102 |
| Ex. 3 | 55.5 | 16.9 | 9.0 | 1.9 | 34 | 110 |
| Ex. 4 | 72.9 | 5.2 | 2.7 | 1.9 | 59 | 72 |
| Ex. 5 | 92.0 | 4.8 | 2.8 | 1.7 | 70 | * |
| Ex. 6 | 15.5 | 12.0 | 8.0 | 1.5 | −24 | 83,60 |
| Ex. 7 | 11.5 | 18.5 | 8.6 | 2.2 | −25 | 75 |
| Ex. 8 | 7.0 | 11.8 | 6.0 | 2.0 | −35 | 90 |
| Ex. 9 | 87.1 | 38.0 | 14.6 | 2.3 | −1 | 103 |
| Ex. 10 | 47.1 | 25.0 | 14.4 | 1.7 | 17 | 113 |
| Ex. 11 | 31.8 | 30.0 | 16.7 | 1.8 | −6 | 83 |
| Ex. 12 | 33.9 | 30.8 | 15.5 | 2.3 | 7 | 95 |
| Ex. 13 | 25.8 | 19.4 | 8.3 | 2.3 | −24 | 98 |
| Ex. 14 | 27.9 | 15.8 | 6.3 | 2.5 | −11 | 71 |
| Comp. Ex. 1 | 43.0 | 14.6 | 8.4 | 1.7 | 0 | * |
| Comp. Ex. 2 | 21.1 | 50.2 | 18.6 | 2.7 | −21 | 25 |
| Comp. Ex. 3 | 49.8 | 35.3 | 17.0 | 2.1 | 31 | * |
| Comp. Ex. 4 | 13.0 | 18.7 | 12.1 | 1.5 | −22 | 63 |
| Comp. Ex. 5 | 9.0 | 1.5 | 0.9 | 1.7 | −27 | 95 |
| Comp. Ex. 6 | <2 | — | — | — | — | 126 |
| Comp. Ex. 7 | 9.5 | 5.0 | 2.4 | 2.0 | −27 | 112 |

*: No melting point was observed.
✗: The peak was a two head peak, and peak separation was carried out for determination.

Figure 2B:
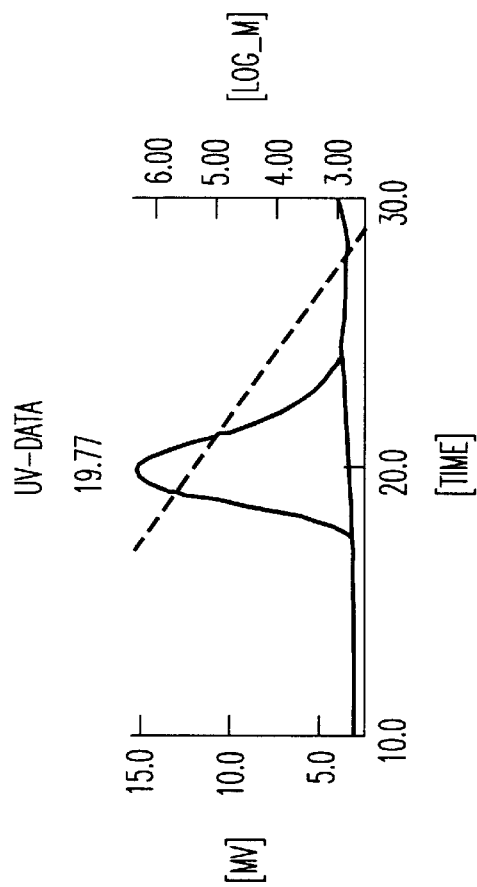
FIG. 2 is a GPC chart of the styrene-ethylene random copolymer obtained in Example 2.
Figure 2A:
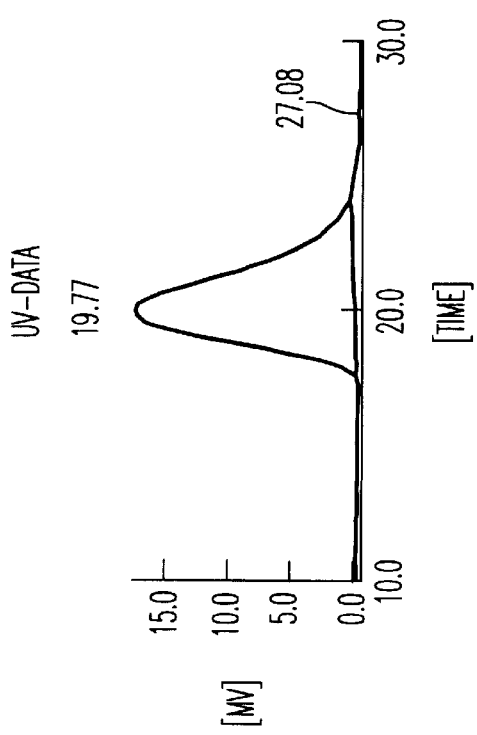
Figure 3:
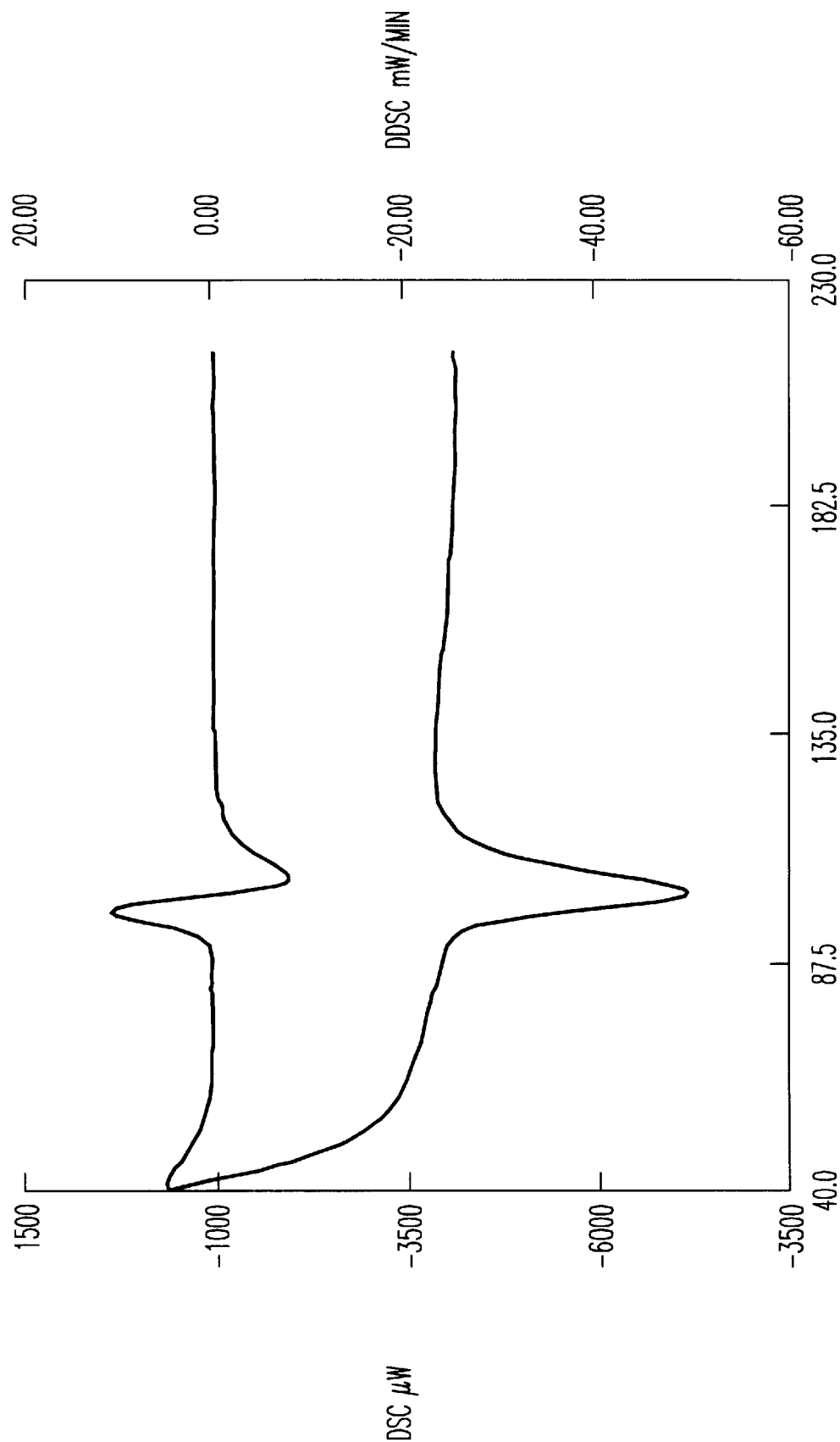
FIG. 3 is a DSC chart of the styrene-ethylene random copolymer obtained in Example 2.

FIGS. 2 and 3 show a GPC chart and a DSC chart of the copolymer obtained in Example 2 as a typical example of the styrene-ethylene copolymer of the present invention.

In the GPC measurements of polymers obtained in various Examples except for Example 1 wherein the polymerization scale was very small, the GPC curves obtained by different detectors (RI and UV) agreed within an experimental error range, as shown in FIG. 2. This indicates that each copolymer has an extremely uniform compositional distribution.

Further, the glass transition point obtained by DSC in Table 2, was one. This also indicates a uniform composition of the copolymer.

Figure 4:
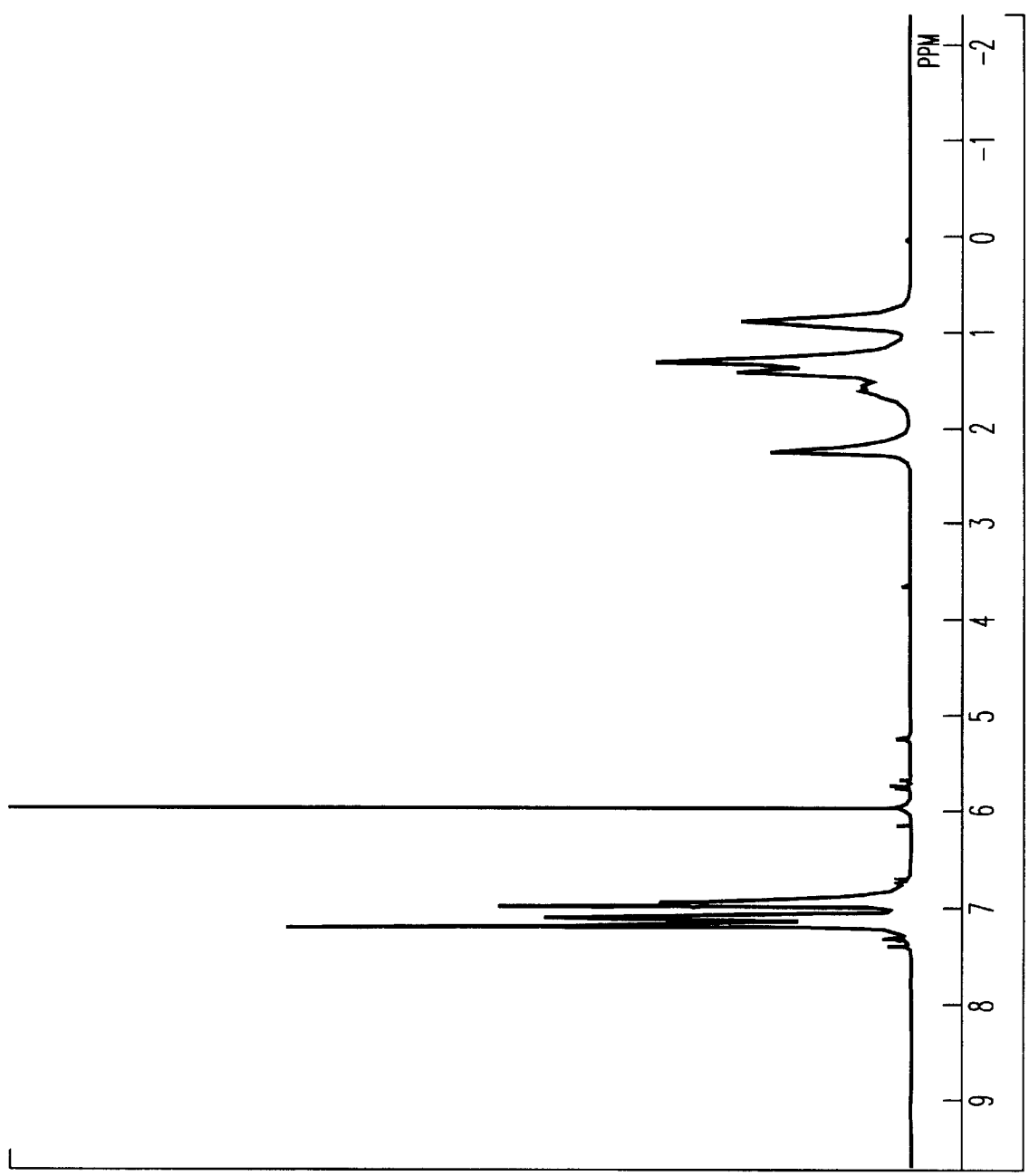
FIG. 4 is a 1H-NMR chart of the styrene-ethylene random copolymer obtained in Example 3.
Figure 5:
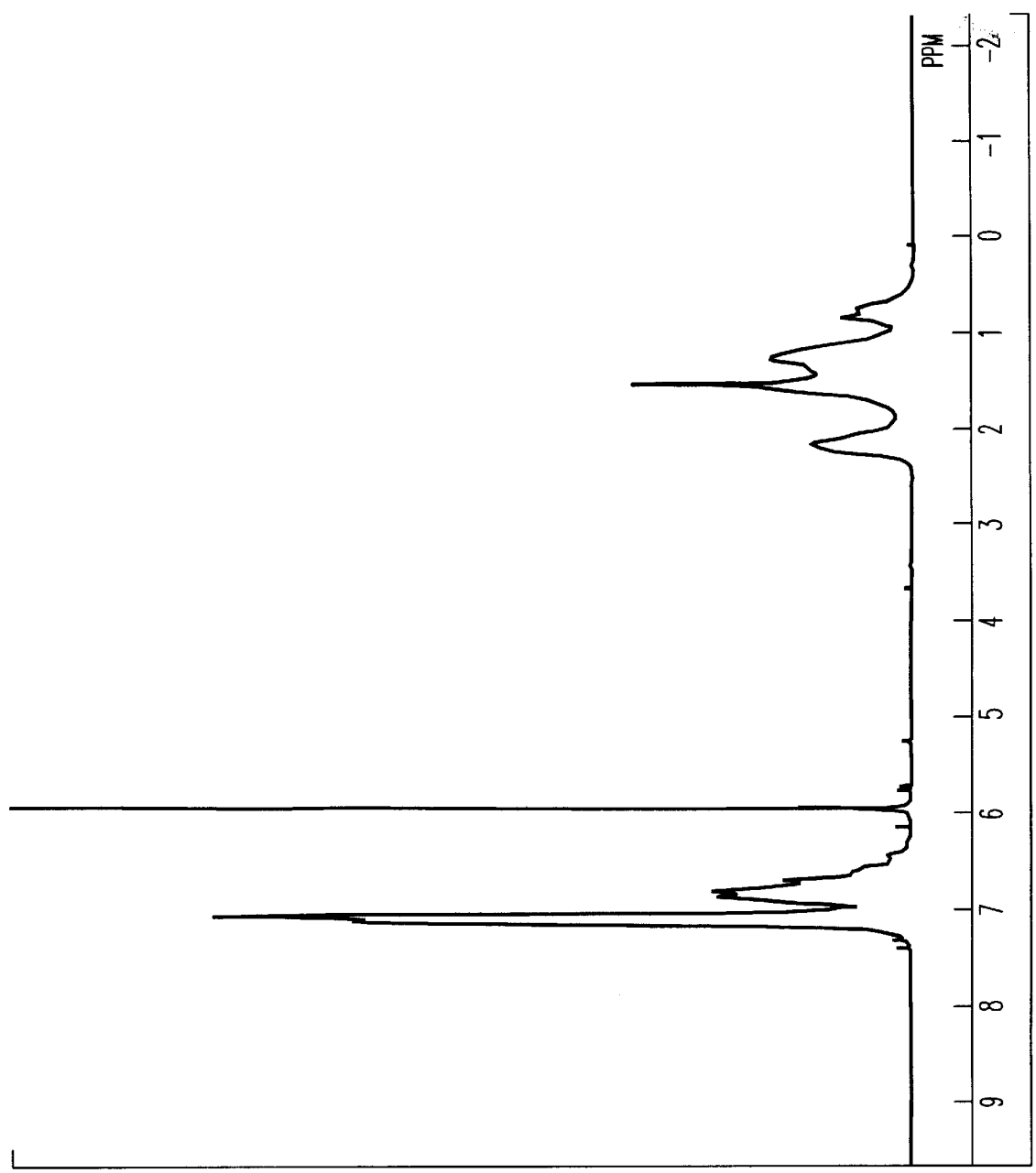
FIG. 5 is a 1H-NMR chart of the styrene-ethylene random copolymer obtained in Example 4.

1H-NMR spectra of the polymers obtained in Examples 3 and 4 are shown in FIGS. 4 and 5.

The styrene-ethylene random copolymer of the present invention is specifically a copolymer containing a typical structure represented by the following formula in an optional proportion.

In the methine and methylene carbon regions in the 13C-NMR spectra, peaks attributable to the following, are shown. Symbols a to o are symbols representing carbon atoms shown in the chemical structures of the formulas (2) and K-32 to K-40.

Peaks attributable to the following, are shown using the center peak (73.89 ppm) of the triplet of 1,1,2,2-tetrachloroethane-d2 as standard.

(1) Alternating structure of styrene and ethylene

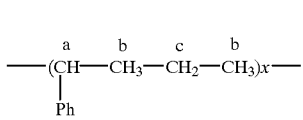

(2)

wherein Ph is a phenyl group, and x is an integer of at least 2, representing the number of repeating units.

Namely, it represents a structure of the following formula which comprises methine carbon atoms bonded to the Ph groups and three methine carbon atoms sandwiched therebetween.

(K-32)

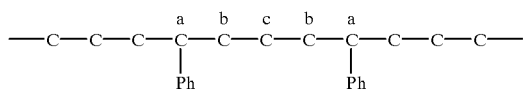

For simplicity, hydrogen atoms are omitted.

(2) Chain structure of ethylene (K-33)

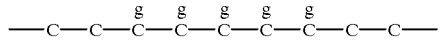

(3) Structure comprising an ethylene chain and one unit of styrene (K-34)

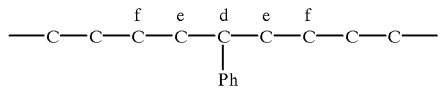

(4) Structure comprising inversion (tail-to-tail structure) of styrene units (K-35)

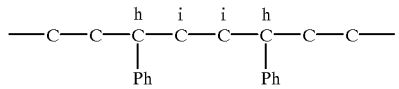

(5) Structure comprising ethylene units or an ethylene chain, and a head-to-tail chain of two styrene units (K-36)

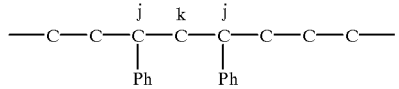

Or, a structure wherein styrene units and styrene-ethylene alternating structural units are randomly bonded.

Styrene unit:

(K-37)

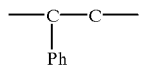

Alternating structural unit;

(K-38)

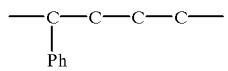

(K-39)

$$\begin{array}{c} \phantom{-}j\phantom{-}k\phantom{-}j\phantom{-}l\phantom{-}m \\ -C-C-C-C-C-C-C-C-C-C- \\ \phantom{-----}|\phantom{-----}|\phantom{-----}|\phantom{-} \\ \phantom{-----}Ph\phantom{----}Ph\phantom{----}Ph \end{array}$$

6) Structure comprising a head-to-tail chain of at least three styrene units (K-40)

$$\begin{array}{c} \phantom{------}n\phantom{--}o \\ -C-C-C-C-C-C-C- \\ \phantom{--}|\phantom{----}|\phantom{----}|\phantom{-} \\ \phantom{--}Ph\phantom{---}Ph\phantom{---}Ph \end{array}$$

25.1–25.2 ppm (c)
36.4–36.5 ppm (b)
44.8–45.4 ppm (a)
29.4–29.9 ppm (g)
36.5–36.8 ppm (e)
27.2–27.6 ppm (f)
45.4–46.1 ppm (d,h)
34.5–34.9 ppm (I)
42.4–43.0 ppm (j)
43.7–44.5 ppm (k)
35.6–36.1 ppm (l)
24.0–24.9 ppm (m)
40.7–41.0 ppm (n)
43.0–43.6 ppm (o)

The above peaks may have some shifts, micro structures of peaks or peak shoulders, due to an influence of the measuring conditions, the solvent used, etc. or due to a distanced effect from the adjacent structure.

Attribution of these peaks was made by literatures such as Macromolecules, 13, 849 (1980), Stuf. Surf. Sci. Catal., 517, 1990, J. Appln. Polymer Sci., 53, 1453 (1994), J. Polymer Phys. Ed., 13, 901 (1975), Macromolecules, 10, 773 (1977), Polymer Preprints, Japan, 42, 292 (1993), EP-416815 and JP-A-4-130114, and by the peak shift prediction by the 13C-NMR Inadequate method, the DEPT method, and the 13C-NMR data base STN (Specinfo).

As typical examples, the 13C-NMR charts of Examples 3, 4, 6, 9, 10, 12 and 13 and Comparative Examples 1 and 3, are shown in FIGS. 6 to 23. The 13C-NMR peak positions of copolymers obtained by typical Examples ad Comparative Examples, are shown in Table 3.

The enlarged 13C-NMR spectra of Examples and Comparative Examples are shown in FIGS. 24 and 25. However, only in the spectrum of Comparative Example 1, $CDCl_3$ is used as the solvent, and for the purpose of comparing with other spectra (1,1,2,2-tetrachloroethane-d2), the peak positions are shown as corrected.

TABLE 3

Main peak shift values (ppm) by 13C-NMR, obtained by using 1,1,2,2-tetrachloroethane-d2 as a solvent

| Attribution | | Example 1 | Example 3 | Example 4 | Example 6 | Example 9 | Example 10 | Example 12 | Example 13 |
|---|---|---|---|---|---|---|---|---|---|
| c | m | 25.11 | 25.11 | 25.10 | 25.12 ~25.22 | 25.12 | 25.11 | 25.11 ~25.15 | 25.12 ~25.16 |
|  | r | — | — | — | — | — | — | — | — |
| a | mm | 45.25 | 45.26 | 45.20 | 45.37 | 45.27 | 45.26 | 45.16 | 45.27 |
|  | mr | — | — | — | — | — | — | — | — |
|  | rr | — | — | — | — | — | — | — | — |
| b |  |  |  |  |  |  |  |  |  |
| m | (m) | 36.46 | 36.45 | 36.45 | 36.48 | 36.46 | 36.45 | 36.43 | 36.46 |
| m | (r) | — | — | — | Over- | — | — | Over- | Over- |

TABLE 3-continued

Main peak shift values (ppm) by 13C-NMR, obtained by using 1,1,2,2-tetrachloroethane-d2 as a solvent

| r | (m) | — | — | — | lapped with block peaks | — | — | lapped with block peaks | lapped with block peaks |
|---|---|---|---|---|---|---|---|---|---|
| r | (r) | — | — | — | | — | — | | |
| g | | 29.3–29.7 | 29.4–29.7 | — | 28.4–29.6 | 29.3–29.7 | 29.3–28.7 | 29.4–29.8 | 29.3–29.5 |
| n | a) | 40.8 | 40.9 | 40.7 | — | — | — | — | — |
|   | b) | — | — | — | — | — | — | — | — |
| o | a) | 43.1 | 43.3 | 42.8 | — | — | — | — | — |
|   |    | 43.2 | 43.5 | 43.5 | — | — | — |   |   |
|   | b) | — | — | — | — | — | — | — | — |
| j |    | 42.9 | 42.7 | 42.4 | — | 42.9 | 42.9 | 42.7 | 42.9 |
|   |    | 42.9 | 42.8 |      |   |      |      |      |      |
| k |    | 43.9 | 43.9 | 43.6 | — | 44.0 | 43.9 | 43.9 | 44.0 |
|   |    |      | 44.0 |      |   |      |      |      |      |

| Attribution | | Comp. Ex. 1 | Comp. Ex. 1 c) | Comp. Ex. 3 |
|---|---|---|---|---|
| c | m | 25.16 | 25.30 | 25.11 |
|   | r | 25.30 | 25.17 | 25.30 |
| a | mm | 45.25 | 45.45 | 45.20 |
|   | mr | 45.32 | 45.56 | 45.29 |
|   | rr | 45.41 | 45.70 | 45.41 |
| b | | | | |
| m | (m) | Many | Many | 36.44 |
| m | (r) | peaks | peaks | 36.51 |
| r | (m) | | | 36.14 |
| r | (r) | | | 36.83 |
| g | | 29.4–29.7 | 29.4–29.6 | 29.4–29.6 |
| n | a) | — | — | — |
|   | h) | — | — | — |
| o | a) | — | — | — |
|   | b) | — | — | — |

Note:
—: No distinct peak was observed by the 13-CNMR measurement commonly conducted in Examples (accumulated number of times: about 5,000 times).
Using 1,1,2,2-tetrachloroethane-d2 as a solvent, the sample was heated and dissolved at 100° C. and then subjected to the measurement. The center peak of the triplet of tetrachloroethane by 13C-NMR had a shift value of 73.89 ppm relative to TMS. Each peak shift value of a copolymer was calculated relative to the center peak value of the triplet of tetrachloroethane being 73.89 ppm.
a) mm, mmm or mmmm    b) rr, rrr or rrrr
c) The peak shift value measured by using TMS as standard and chloroform-d as a solvent.

The alternating structural index λ, the isotactic diad index m of the styrene-ethylene alternating structure and the isotactic diad index ms of the head-to-tail styrene chain unit structure, of the copolymer obtained in each Example, were obtained in accordance with the above formulas (i), (ii) and (iii). The m and as values obtained in the respective Examples and Comparative Examples are shown in Table 4.

TABLE 4

| Examples | St content (mol %) | Value 2 | Value m | Value ms |
|---|---|---|---|---|
| Ex. 1 | 41.0 | 48 | >0 | >0.80 |
| Ex. 2 | 53.8 | 50 | >0.95 | >0.80 |
| Ex. 3 | 55.5 | 57 | >0.95 | >0.80 |
| Ex. 4 | 72.9 | 20 | >0.95 | >0.80 |
| Ex. 5 | 92.0 | 7 | >0.95 | >0.80 |
| Ex. 6 | 15.5 | 8 | >0.95 | — |
| Ex. 7 | 11.5 | 6 | >0.95 | — |
| Ex. 8 | 7.0 | 4 | >0.95 | — |
| Ex. 9 | 37.1 | 47 | >0.95 | — |
| Ex. 10 | 47.1 | 59 | >0.95 | >0.80 |
| Ex. 11 | 31.8 | 25 | >0.95 | — |
| Ex. 12 | 38.9 | 30 | >0.95 | — |

TABLE 4-continued

| Examples | St content (mol %) | Value 2 | Value m | Value ms |
|---|---|---|---|---|
| Ex. 13 | 25.8 | 19 | >0.95 | — |
| Ex. 14 | 27.9 | 18 | >0.95 | — |
| Comp. Ex. 1 | 43.0 | NM | 0.65 | — |
| Comp. Ex. 2 | 21.1 | NM | 0.7 | — |
| Comp. Ex. 3 | 49.8 | NM | 0.60 | — |
| Comp. Ex. 4 | 13.0 | NM | 0.5 | — |
| Comp. Ex. 5 | 9.0 | NM | 0.5 | — |
| Comp. Ex. 6 | <2 | NM | NM | — |

TABLE 4-continued

| Examples | St content (mol %) | Value 2 | Value m | Value ms |
|---|---|---|---|---|
| Comp. Ex. 7 | 9.5 | NM | 0.9 | — |

NM: Not measured
Note:
—: No distinct peak attributable to a at least three head-to-tail styrene chain (a polystyrene chain), was observed by the 13-CNMR measurement commonly carried out in Examples (accumulated number of times: about 5,000 times), and no calculation was accordingly possible.

Further, the isotactic pentad index mmmm of styrene units, can be obtained by the following formula from the peak of the phenyl C1 carbon or the methylene carbon of the styrene chain structure by the 13C-NMR measurement.

mmmm=A(mmmm)/A(all)

A(mmmm): peak area of phenyl C1 carbon attributable to the mmmm structure of the styrene chain
A(all): Sum of all peak areas of phenyl C1 carbon attributable to the stereoregularity.

Especially, in the case of the phenyl C1 carbon peak, a peak attributable to phenyl C1 of the copolymer structure is present in the vicinity of the mmmm peak of a head-to-tail styrene chain, but no substantial peak is observed in the vicinity of from 145.2 to 146.0 ppm which is the position where the peak attributable to an atarctic styrene chain or a syndiotactic styrene chain structure appears. Thus, mmmm is at least 0.2.

To show that the copolymer of the present invention can have a crystalline structure, the X-ray diffraction patterns of the copolymers obtained in Examples 10 and 14 are shown in FIG. 26. The samples were subjected to suitable annealing treatment to improve the crystallinity, whereupon the measurements were carried out.

With a styrene-ethylene random copolymer of the present invention with a styrene content of at least 15 mol %, a diffraction peak from the crystal structure attributable to the stereoregular styrene-ethylene alternating structure contained, was observed. When the styrene content is less than about 15 mol %, a diffraction peak from a crystal structure of polyethylene will also be observed.

When a CGCT (constrained geometrical structure) type Ti complex, (tertiary butylamide)dimethyl(tetramethyl-η5-cyclopetandienylsilanetitanium dichloride or diphenylmethylene(fluorenyl)(cyclopentadienyl)zirconium dichloride, is employed as the transition metal catalyst component, the styrene-ethylene alternating structure in the resulting copolymer, has no stereoregularity. Further, no head-to-tail styrene chain is observed.

When rac-ethylenebis(1-indenyl)zirconium dichloride is used as the transition metal catalyst component, it is very difficult to increase the styrene content to a level of at least 10 mol %, and the molecular weight of the resulting polymer is as low as 50,000 by weight average molecular weight (Mw). The copolymer with a styrene content of at least 5 molt and less than 20 mol %, which has a weight average molecular weight of less than 60,000, is not useful as a practical polymer, since the physical properties such as breaking strength, etc. are poor. When the same transition metal catalyst component is employed, as shown in Comparative Example 10, homopolymerization of styrene does not proceed. It is impossible to form a styrene chain by this catalyst system.

When dimethylsilylenebis (2-methyl-4,5-benzindenyl) zirconium dichloride having a substituent pattern of the benzindenyl group which is different from the transition metal compound as catalyst component for polymerization of the present invention, is employed, a copolymer having a styrene content of not more than 2 mol %, is obtained. Namely, when a metal complex having a substituent at the 2-position of the benzindenyl group, is used, it is impossible to obtain a high styrene content. Further, no head-to-tail styrene chain is observed. When the same transition metal catalyst component is used, as shown in Comparative Example 9, no styrene polymer having stereoregularity can be obtained. An atarctic polystyrene produced in a small amount, is considered to have been formed by cation or radical polymerization, according to known literatures. Thus, it is impossible to form a styrene chain by this catalyst system.

Preparation of Styrene-propylene Random Copolymers

Example 15

An autoclave having a capacity of 1 lit. and equipped with a stirrer, was evacuated and substituted by nitrogen, and then 100 ml of styrene, 40 ml of toluene, 5 mmol of triisobutylaluminum and 21 mmol, based on Al atom, of methylalumoxane (MMAO-3A, manufactured by TOSOH-AKZO K.K.) were charged in this order. Then, the autoclave was cooled to −50° C. by dry ice, and 1 mol of propylene gas was introduced. About 40 ml of a toluene solution containing 21 μmol of a catalyst rac{BInd-C(Me)$_2$-BInd}ZrCl$_2$ and 0.84 mmol of triisobutylaluminum, was introduced together with propylene gas, from a pressure resistant tank installed above the autoclave. The dry ice bath was removed, and temperature was raised to 50° C. over a period of about 30 minutes and polymerization was carried out at 50° C. for one hour. After completion, the pressure was gradually released, and the polymerization solution was post-treated in the same manner as in Example 1 to obtain 8.5 g of a polymer.

Examples 16 to 18

Polymerization and post treatment were carried out in the same manner as in Example 15 under the polymerization conditions shown in Table 5.

Comparative Example 8

Polymerization and post treatment were carried out in the same manner as in Example 15 under the conditions shown in Table 2, using, as a complex, dimethylsilylenebis(2-methyl-4,5-benzindenyl)zirconium dichloride.

Table 5 shows the polymerization conditions and the results.

Table 6 shows the styrene content and the molecular weight obtained by GPC, of the obtained polymer, and the results of the glass transition point and melting point obtained by DSC.

FIGS. 27 and 28 show the GPC chart and the DSC spectrum of the copolymer obtained in Example 15.

In the GPC measurements of the polymers obtained in various Examples, the GPC curves obtained by different detectors (RI and UV) agree to each other within an experimental error range, as shown in FIG. 27, although a small shoulder is observed. This indicates that the compositional distribution of styrene is relatively uniform.

The glass transition point obtained by DSC being one, also indicates a uniform composition of the copolymer.

Typical 13C-NMR charts of Examples 15, 17 and 18 are shown in FIGS. 29 to 34.

Table 7 shows the results of 13C-NMR measurements,

The styrene-propylene copolymers of the present invention present complex peak patterns by the 13C-NMR measurements, as shown in the Figures. This indicates that many different kinds of bond structures were formed, for example, by formation of head-to-tail or tail-to-tail chains of propylene units one another, styrene units one another or a propylene unit and a styrene unit bonded to each other, or a structure similar to an ethylene chain due to a 1–3 bond of propylene.

However, among peaks of phenyl C1 carbon of a styrene unit (the carbon bonded to the main chain among six carbon atoms of a phenyl group), the peak in the vicinity of 146.3 ppm is attributable to an isotactic polystyrene chain, and the peak at 21.5 to 21.6 ppm of methyl carbon in a propylene unit, is attributable to an isotactic polypropylene chain. Namely, it is a copolymer which has a styrene chain structure, a propylene chain structure and a styrene-propylene bond structure, wherein the stereoregularity of the styrene chain structure and/or the propylene chain structure is isotactic.

In the case of a propylene chain, the isotactic index (mm, mmm or mmmm) is obtained by comparing the area of an isotactic peak (mm, mmm or mmmm) of a methyl group in the vicinity of 21.5 ppm and the area of peaks of all methyl groups. With respect to the propylene chain, the isotactic index (mm, mmm or mmmm) is such that mm is at least 0.5, mmm is at least 0.4, and mmmm is at least 0.2, although other peaks attributable to the above-mentioned complex bond structures, are present in the vicinity.

In the case of a styrene chain, the isotactic index (mm, mmm or mmmm) can be obtained by comparing the area of the isotactic peak (mm, mmm or mmmm) of the phenyl C1 group in the vicinity of 146.3 ppm and the area of all phenyl C1 peaks in the vicinity of from 145 to 146 ppm. With respect to the styrene chain, the isotactic index (mm, mmm or mmmm) is such that mm is at least 0.5, mmm is at least 0.4, and mmmm is at least 0.2.

When dimethylsilylenebis(2-methyl-4,5-bnzoindenyl) zirconium dichloride having a substituent pattern on a benzindenyl group which is different from the transition metal catalyst component for polymerization of the present invention, is used, a mixture comprising an isotactic polypropylene and an atarctic polystyrene, will be obtained.

Preparation of Isotactic Polystyrenes

Into a Shrenk tube having a capacity of 100 ml and equipped with a magnetic stirrer, which was evacuated and substituted by nitrogen, 10 ml of styrene and 0.84 mmol of triisobutylaluminum were charged. Further, 0.8 µmol, based on Al, of methyl alumoxane (MMAO-3A, manufactured by TOSOH-AKZO K.K.) was added thereto, and 10 ml of a toluene solution containing 1.5 µmol of rac-dimethylmethylenebis(4,5-benz-1-indenyl)zirconium dichloride, was added thereto. The mixture was stirred at room temperature for 3 hours and then put into a large excess amount of methanol acidified with hydrochloric acid to precipitate a polymer. The obtained polymer was dried at 70° C. for 8 hours to obtain 1.5 g of a white powdery polymer.

Example 20

Polymerization and post treatment were carried out in the same manner as in Example 19 under the conditions shown in Table 3 by using, as a complex, 4.6 µmol of rac-dimethylmethylene(4,5-benz-1-indenyl)(1-indenyl) zirconiun dichloride, to obtain 0.5 g of a white powdery polymer.

Comparative Example 9

Polymerization and post treatment were carried out in the same manner as in Example 13 under the conditions shown in Table 3, by changing the complex to rac-dimethylsilylbis (2-methyl-4,5-benzindenyl) zirconium dichloride, another name; rac{2-Me-BInd-SiMe$_2$-2-Me-BInd}ZrCl$_2$, to obtain 0.15 g of a white powdery polymer.

Comparative Example 10

Polymerization and post treatment were carried out in the same manner as in Example 19 under the conditions shown in Table 3 by changing the complex to rac-ethylenebis (1-indenyl) zirconium dichloride, another name: rac{Ind-Et-Ind}ZrCl$_2$, whereby no polymer was obtained.

Table 8 shows the polymerization conditions and the results.

Table 9 shows the molecular weight of the obtained polymer determined by GPC, and the results of the glass transition point and melting point determined by DSC.

The 13C-NMR chart of the obtained polymer is shown in FIG. 35, the DSC chart is shown in FIG. 36, and the X-ray diffraction pattern is shown in FIG. 37.

The peak shift value of the 13C-NMR obtained by using the center peak (73.89 ppm) of the triplet of 1,1,2,2-tetrachloroethane-d2, as standard, was as follows.

|  | Methine carbon | Methylene carbon | Phenyl C1 carbon |
|---|---|---|---|
| EXAMPLE 19 | 40.7 | 43.0 | 146.3 |
| EXAMPLE 20 | 40.7 | 43.0 | 146.3 |

The melting point obtained by DSC was 222° C., and from the results of the X-ray diffraction, it is evident that the obtained copolymer was an isotactic polystyrene.

The meso pentad index (mmmm) obtained from the peak of the phenyl C1 carbon of the isotactic polystyrene obtained in Example 19, was at least 0.90. In the case of Comparative Example 9 wherein rac-dimethylsilylenebis(2-methyl-4,5-benzindenyl)zirconium dichloride was used, a very small amount of atarctic polystyrene was obtained, but this is considered to have been formed by radical polymerization or cation polymerization by the coexisting methylalumoxane or an alkylaluminum included therein.

In the case of Comparative Example 10 wherein rac-ethylenebis(1-indenyl)zirconium dichloride was used, no polymer was obtained.

Preparation of Styrene-ethylene Alternating Copolymers

Example 21

Polymerization was carried out by using an autoclave having a capacity of 1 lit. and equipped with a stirrer.

240 ml of toluene and 240 ml of styrene were charged, and the inner temperature was raised to 50° C. About 80 lit of nitrogen was introduced for bubbling to purge the interior of the system. Then, the autoclave was cooled by immersing it in an ice bath. Then, 8.4 mmol of triisobutylaluminum and 8.4 mmol, based On Al, of methylalumoxane (PMAO-S, manufactured by TOSOH-AKZO K.K.) were added thereto. Ethylene was immediately introduced, and after the pressure was stabilized at 0.2 MPa (1 kg/cm²G), about 30 ml of a toluene solution containing 6 kg/cm²mol of a catalyst obtained in "Preparation A", rac-dimethylmethylene bis(4, 5-benz-1-indenyl)zirconium dichloride and 0.84 mmol of triisobutylaluminum, was added to the autoclave from a catalyst tank installed above the autoclave. Polymerization was carried out for 6 hours while maintaining the inner temperature at a level of 2 to 6° C. and the ethylene pressure at a level of 0.2 MPa(1 kg/cm²G). During the polymerization, the rate of consumption of ethylene was monitored by a flow rate accumulator, so that the progress of the polymerization reaction was monitored. Upon expiration of 6 hours, polymerization was substantially in progress without no deactivation. The ethylene pressure was released, and the obtained polymerization solution was gradually put into an excess amount of methanol to precipitate the formed polymer. The product was dried for about 10 hours under reduced pressure at 80° C. until no weight change was any longer observed, to obtain 39 g of a polymer.

Example 22

Polymerization and post treatment was carried out in the same manner as in Example 21 except that the complex was used in an amount of 8.4 μmol and polymerization was carried out by immersing the autoclave in a cooling bath of −20° C. to maintain the inner temperature at −16° C., to obtain 1.5 g of a polymer. This polymer contained atarctic polystyrene homopolymer, and it was further subjected to extraction treatment with boiling acetone, whereby 0.7 g of a white powder polymer was obtained as an insoluble fraction in boiling acetone.

Comparative Example 11

Polymerization and post treatment were carried out in the same manner as in Example 21 under the conditions shown in Table 4, by using, as the catalyst, ethylenebisindenylzirconium dichloride. As a result, 14 g of a polymer was obtained.

The obtained copolymer was a mixture of atarctic polystyrene and the copolymer, and it was extracted with boiling acetone to obtain 8 g of a white polymer as an insoluble fraction in boiling acetone.

The polymerization conditions and the polymerization results in the respective Examples and Comparative Examples are shown in Table 10.

Further, the molecular weights, the molecular weight distributions, the melting points and the glass transition temperatures of the copolymers obtained in the respective Examples and Comparative Examples are shown in Table 11, and the 13C-NMR peak shift values are shown in Table 12.

As an example of the copolymer obtainable by the present invention, the 1H-NMR of the copolymer obtained in Example 21 is shown in FIG. 38, and the 13C-NMR spectrum is shown in FIGS. 39 and 40.

The aromatic vinyl compound-ethylene alternating copolymer obtained by the present invention, is an aromatic vinyl compound-ethylene alternating copolymer characterized in that the stereoregularity of phenyl groups in the alternating structure of ethylene and the aromatic vinyl compound, is represented by an isotactic diad index m of larger than 0.95, and the alternating structure index λ of the following formula (i) is at least 70.

The alternating index λ is given by the following formula (i):

$$\lambda = A3/A2 \times 100 \qquad (i)$$

Here, A3 is the sum of areas of three peaks a, b and c attributable to the carbons of aromatic vinyl compound-ethylene alternating structure of the following formula (5'), as obtained by the 13C-NMR measurements, and A2 is the sum of areas of peaks attributable to the main chain methylene and methine carbon, as observed within a range of from 0 to 50 ppm by 13C-NMR using TMS as standard.

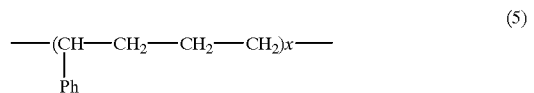

(5)

wherein Ph is an aromatic group such as a phenyl group, and x is an integer of at least 2, representing the number of repeating units,

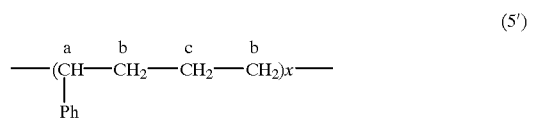

(5')

wherein Ph is an aromatic group such as a phenyl group, and x is an integer of at least 2, representing the number of repeating units.

Namely, it has a structure represented by the following formula which comprises methine carbon atoms bonded to the Ph groups and three methylene carbon atoms sandwiched therebetween. (For the simplicity, hydrogen atoms are omitted.)

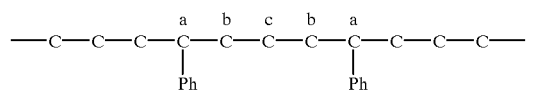

The isotactic diad (meso diad) index m of the alternating copolymer structure of ethylene and styrene, can be obtained by the above formula (ii).

Further, the alternating structure index λ obtained by the above formula is shown in Table 13.

The isotactic diad index m of the styrene unit-ethylene unit alternating structure of the copolymer obtained in each Example, was obtained by the above formula. Table 13 shows m obtained in each Example or Comparative Example.

As an example of the copolymer obtainable by the present invention, the GPC chart of the copolymer obtained in Example 21 is shown in FIG. 41.

As an example of the copolymer obtainable by the present invention, the DSC chart of the copolymer obtained in Example 22 (measured after quenching with liquid nitrogen from a molten state, the temperature raising rate; 20° C./min) is shown in FIG. 42.

It is evident from FIG. 42 that the copolymer of the present invention has a high melting point and a high crystallization speed.

As an example of the copolymer obtainable by the present invention, the X-ray diffraction chart of the copolymer obtained in Example 21 is shown in FIG. 43.

As shown in Comparative Example 11, in a case where ethylenebisindenylzirconium dichloride is used as a metal complex, the styrene content can not be increased under a practical polymerization temperature condition of at least -20° C., whereby it is impossible to obtain a copolymer having a high alternating nature.

TEST EXAMPLES

Preparation D of Transition Metal Compound as Catalyst Component

Rac-dimethylmethylenebis(3-cyclopenta[c]phenanthryl) zirconium dichloride (rac{CpPhen-CMe$_2$-CpPhen}ZrCl$_2$), was prepared as follows. Here, CpPhen represents cyclopentadienyl[c]phenanthryl.

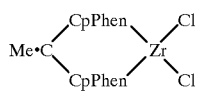

1H or 3H-cyclopenta[c]phenanthrene was prepared in accordance with the method disclosed in Organometallics, 16, 3413, 1997.

D-1 Isopropylidenebis(cyclopenta)[c]phenanthrene)

In an Ar atmosphere, 32 mmol of 1H or 3H-cyclopenta [c]phenanthrene was added to 40 ml of dimethoxyethane having 3.0 g of potassium hydroxide suspended therein, and the mixture was stirred at room temperature for 30 minutes. Then, 15 mmol of acetone was added thereto, followed by stirring at 60° C. for 2 hours. A 10% phosphoric acid aqueous solution was added for neutralization, and the mixture was extracted with methylene chloride. The organic layer was washed with water and dried, and methylene chloride was distilled off. By recrystallization from a methylene chloride-diethyl ether solution, 1.5 g of isopropylidenebis(cyclopenta[c]phenanthrene) was obtained as white crystals.

By the 1H-NMR spectrum measurement, it had peaks at 1.93 ppm (6H,s), 4.20 ppm (4H,d), 6.89 ppm (2H,t), 7.5 to 7.9 ppm (14H,m) and 8.91 ppm (2H,d), The measurement was carried out by using TMS as standard and CDCl$_3$ as the solvent.

D-3 Preparation of rac-dimethylmethylenebis(3-cyclopenta [c]phenanthryl)zirconium dichloride In an Ar stream, 2.0 mmol of isopropylidenebis (cyclopenta[c]phenanthrene) and 2.0 mmol of zirconium tetrakisdimethylamide{Zr(NMe$_2$)$_4$} were charged together with 20 ml of toluene and stirred for 7 hours under reflux. Toluene was distilled off under reduced pressure, and 50 ml of methylene chloride was added thereto. The mixture was cooled to -50° C. Then, 4.0 mmol of dimethylamine hydrochloride was gradually added, and the temperature was slowly raised to room temperature, and stirring was further conducted for 2 hours. After distilling off the solvent, the obtained solid was washed with pentane and then with a small amount of methylene chloride to remove meso-isomer and ligand, to obtain 0.36 g of rac-dimethylmethylenebis(3-cyclopenta[c]phenanthryl)zirconium dichloride as yellow orange crystals. From the 1H-NMR spectrum, it was found to have peaks at 2.55 ppm (6H,s), 6.49 ppm (2H,d), 7.55–8.02 ppm (16H,m), and 8.82 ppm (2H,d).

The measurement was carried out by using TMS as standard and CDCl$_3$ as a solvent.

Preparation of Styrene-ethylene Random Copolymers

Example 23

Polymerization and post treatment were carried out in the same manner as in Example 2 under the conditions shown in Table 14, by using, as a catalyst rac-dimethylmethylenebis (3-cyclopenta[c]phenanthryl)zirconium dichloride which is the catalyst obtained in "Preparation D of transition metal compound as catalyst component".

As a result, 910 g of a polymer was obtained. The styrene content was 57.0 mol %, the molecular weight (Mw) was 279,000, the molecular weight distribution (Mw/Mn) was 2.0, and the glass transition point was 40° C.

As a result of the 13C-NMR measurement, a peak was observed which is attributable to two or more head-to-tail styrene chain structure.

The 13C-NMR spectra are shown in FIGS. 44, 45 and 46. The peak shift values of the 13C-NMR spectra are shown in Table 15.

The stereoregularity of the styrene-ethylene alternating structure was isotactic, and m was at least 0.95, ms was at least 0.80, and the alternating structure index λ was 30. When this complex is used as a catalyst component, it is possible to obtain a copolymer having a high random nature (low alternating nature) under the conditions of Examples.

Example 24

Polymerization and post treatment were carried out n the same manner as in Example 19 under the conditions shown in Table 14, by using, as a catalyst, rac-dimethylmethylenebis(3-cyclopenta[c]phenanthryl) zirconium dichloride which is the catalyst obtained in "Preparation D of transition metal compound as catalyst component". As a result, 1.8 g of a polymer was obtained.

The molecular weight (Mw) was 208,000, the molecular weight distribution (Mw/Mn) was 1.7, and the melting point was 225° C. The peak shift values of 13C-NMR obtained by using the center peak (73.89 ppm) of the triplet of 1,1,2,2-tetrachloroethane-d2 as standard, were as follows.

|  | Methine carbon | Methylene carbon | Phenyl C1 carbon |
|---|---|---|---|
| EXAMPLE 24 | 40.7 | 43.0 | 146.3 |

The meso pentad index (mmmm) obtained from the phenyl C1 carbon peak was at least 0.95.

When rac-dimethylmethylenebis(3-cyclopenta[c] phenanthryl)zirconium dichloride is used as a transition metal catalyst component, it is possible to produce a styrene-ethylene random copolymer having a high molecular weight and an isotactic polystyrene under very high catalytic activities.

REFERENCE EXAMPLE 1 Preparation of polyethylene

Into an autoclave having a capacity of 120 ml and equipped with a magnetic stirrer, which was evacuated and substituted by ethylene, 20 ml of toluene and 8.4 μmol, based on Al atom, of methylalumoxane (MMAO-3A, manufactured by TOSOH AKZO K.K.) were charged.

The inner temperature was raised to 50° C., and 16 ml of a toluene solution containing 1.0 μmol of rac{BInd-C(Me)$_2$-BInd}ZrCl$_2$ and 0.84 mmol of triisobutylaluminum, was quickly charged by a syringe with magnetic stirring, and ethylene was immediately introduced to raise the pressure to a total pressure of 0.6 MPa (5 kg/cm$^2$G). Polymerization was carried out for 10 minutes while maintaining the pressure at a level of 5 kg/cm$^2$G. The polymerization solution was put into a large excess amount of dilute hydrochloric acid/methanol liquid to precipitate a polymer, which was dried under vacuum at 70° C. for 8 hours. As a result, 1.7 g of a polyethylene was obtained, As a result of the DSC measurement, the melting point was 130° C.

TABLE 5

| Example | Catalyst | Amount of catalyst (mol) | Cocatalyst (mmol) | Amount of toluene (ml) | Amount of styrene (ml) | Amount of propylene (mol) | PTE (° C.) | PTI (hr) | Yield (g) | Productivity (g/mol-catalyst)/10[b] | St content (mol %) (%) |
|---|---|---|---|---|---|---|---|---|---|---|---|
| Ex. 15 | A | 21 | 21 | 80 | 100 | 1.0 | −50 50 | 1.5 | 8.5 | 0.4 | 55.6 |
| Ex. 16 | A | 8.4 | 21 | 80 | 100 | 1.0 | 50 | 1 | 2.3 | 0.27 | 42.2 |
| Ex. 17 | A | 8.4 | 21 | 160 | 20 | 2.0 | 20~38 | 1 | 23.3 | 2.8 | 3.9 |
| Ex. 18 | A | 8.4 | 21 | 80 | 100 | 0.25 | 50 | 1 | 1.9 | 0.23 | 72.5 |
| Comp. Ex. 8 | F | 21 | 21 | 80 | 100 | 1.0 | 50 | 1 | 0.4 (0.3) (0.1) | 0.02 Atarctic PS Isotactic PP | 100 ~0 |

Transition metals used as catalysts
A: rac-dimethylmethylenebis(4,5-benz-1-indenyl) zirconium dichloride
F: rac-dimethylsilylenebis (2,methyl-4,5-benz-1-indenyl) zirconium dichloride
PTE: Polymerization temperature
PTI: Polymerization time

TABLE 8

| Example | Catalyst | Amount of catalyst (mol) | Cocatalyst (mmol) | Amount of toluene | Amount of styrene | PTE (° C.) | PTI (hr) | Yield (g) | Productivity (g/mol-catalyst)/10[b] |
|---|---|---|---|---|---|---|---|---|---|
| Ex. 19 | A | 1.5 | 8.4 | 10 | 10 | 23 | 3 | 1.5 | 1.0 |
| Ex. 20 | B | 4.6 | 8.4 | 10 | 10 | 23 | 3 | 0.5 | 0.1 |
| Comp. Ex. 9 | F | 3.6 | 8.4 | 16 | 10 | 23 | 3 | 0.15 | 0.04 |
| Comp. Ex. 10 | G | 8.4 | 8.4 | 16 | 10 | 23 | 3 | 0 | 0 |

Transition metals used as catalysts
A: rac-dimethylmethylenebis(4,5-benz-1-indenyl) zirconium dichloride
B: rac-dimethylmethylenebis(1-indenyl) (4,5-benz-1-indenyl) zirconium dichloride
F: rac-dimethylsilylenebis (2,methyl-4,5-benz-1-indenyl) zirconium dichloride
G: rac-ethylenebis(1-indenyl) zirconium dichloride
PTE: Polymerization temperature
PTI: Polymerization time

TABLE 6

| Examples | St content (mol %) | Mw /10* | Mn /10* | Mw/Mn | Glass transition temp. (° C.) | Melting point (° C.) |
|---|---|---|---|---|---|---|
| Ex. 15 | 55.6 | 2.0 | 1.2 | 1.7 | 35 | * |
| Ex. 16 | 42.2 | 1.6 | 0.9 | 1.8 | 35 | * |
| Ex. 17 | 3.9 | 1.7 | 1.0 | 1.0 | −18 | 118 |
| Ex. 18 | 72.5 | 1.6 | 0.9 | 1.7 | 75 | * |
| Comp. Ex. 8 | 100 ~0 | 2.1 11.2 | 0.7 4.6 | 3.0 2.5 | — — | — — |

*: No melting point was observed.

TABLE 9

| Examples | Mw/ 10[4] | Mn/ 10[4] | Mw/Mn | Glass transition temp. (° C.) | Melting point (° C.) |
|---|---|---|---|---|---|
| Ex. 18 | 3.6 | 1.9 | 1.9 | 85 | 222 |
| Ex. 19 | 2.0 | 1.1 | 1.9 | 85 | 220 |
| Comp. Ex. 9 | 1.0 | 0.6 | 1.7 | 88 | * |
| Comp. Ex. 10 | — | — | — | — | — |

*No melting point was observed.

TABLE 7

Main peak shift values (ppm) by 13C-NMR, obtained by using 1,1,2,2-tetrachloroethane d2 as a solvent

| Attribution | Ex. 15 | Ex. 16 | Ex. 17 | Ex. 18 |
|---|---|---|---|---|
| Propylene Unit methyl | 21.54 | 21.54 | 21.52 | 21.6 |
| Propylene Unit methylene | 27.42 27.65 | 27.42 27.63 | 28.05 | Not distinct |
| Propylene Unit methine | 45.3 | 45.28 | 45.70 | Not distinct |
| Styrene unit methine | 40.42 −40.50 | 40.4 −40.5 | Not distinct | 40.53 |
| Styrene Unit methylene | 42.8—43.2 | 42.5—43.2 | Not distinct | 42.95 |
| Styrene Unit Phenyl C1 | 113.68 146.30 146.61 | 143.67 146.31 146.60 | 144.42 146.63 | 145.73 146.31 |

Note:
—: No distinct peak was observed by the 13-CNMR measurement commonly conducted in Examples (accumulated number of times: about 5,000 times).
Using 1,1,2,2-tetrachloroethane-d2 as a solvent, the sample was heated and dissolved at 100° C. and then subjected to the measurement. The center peak of the triplet of tetrachloroethane by 13C-NMR had a shift value of 73.89 ppm relative to TMS. Each peak shift value of a copolymer was calculated relative to the center peak value of the triplet of tetrachloroethane being 73.89 ppm.

TABLE 10

| Examples | Catalyst | Amount of catalyst (mol) | Cocatalyst (mmol) MAO | Amount of toluene (ml) | Amount of styrene (ml) | Ethylene pressure MPa | PTE (° C.) | PTI (hr) | Yield (g) | Productivity (g/mol-catalyst)/10⁶ | St content (mol %) |
|---|---|---|---|---|---|---|---|---|---|---|---|
| Ex. 21 | A | 6 | 8.4 | 240 | 240 | 0.2 | 2~6 | 6 | 39 | 6.5 | 53.3 |
| Ex. 22 | A | 8.4 | 8.4 | 240 | 240 | 0.2 | −16 | 6 | 1.5 (0.7) | 0.2 (0.1) | (50.0) |
| Comp. Ex. 11 | G | 21 | 21 | 80 | 400 | 0.2 | 2~6 | 6 | 14 (8) | 0.7 (0.4) | (21.0) |

In the bracket ( ), a boiling acetone-insoluble content (styrene-ethylene copolymer) is indicated.
Transition metals used as catalysts
A: rac-dimethylmethylenebis(4,5-benz-1-indenyl) zirconium dichloride
G: rac-ethylenebis(1-indenyl) zirconium dichloride
PTE: Polymerization temperature
PTI: Polymerization time

TABLE 14

| Examples | Catalyst | Amount of catalyst (mol) | Cocatalyst (mmol) MAO | Amount of solvent (ml) | Amount of styrene (ml) | Ethylene pressure MPa | PTE (° C.) | PTI (hr) | Yield (g) | Productivity (g/mol-catalyst)/10⁶ | St content (mol %) |
|---|---|---|---|---|---|---|---|---|---|---|---|
| Ex. 23 | H | 21 | 84 | T 800 | 4000 | 0.2 | 50 | 5 | 910 | 43.3 | 57.0 |
| Ex. 24 | H | 1.0 | 8.4 | T 16 | 10 | — | 23 | 3 | 1.8 | 1.8 | 100 |

T: Toluene
Transition metals used as catalysts
H: dimethylmethylenebis (3-cyclopenta(c)phenanthryl)zirconium dichloride
PTE: Polymerization temperature
PTI: Polymerization time

TABLE 11

| Examples | St content (mol %) | Mw /10⁴ | Mn /10⁴ | Mw/Mn | Glass transition temp. (° C.) | Melting point (° C.) |
|---|---|---|---|---|---|---|
| Ex. 20 | 53.3 | 31.7 | 23.7 | 1.8 | 27 | 134 |
| Ex. 21* | 50.0 | 2.0 | 1.1 | 1.8 | 22 | 158 |
| Comp. | 27.0 | 2.4 | 1.3 | 1.8 | −2 | 120 |

*Boiling acetone-insoluble fraction (styrene-ethylene copolymer)

TABLE 12

Main peak shift values (ppm) by 13C-NMR, obtained by using 1,1,2,2-tetrachloroethane d2 as a solvent

| Attribution | | Ex. 21 | Ex. 22 *1 | Comp. Ex. 11 *1 |
|---|---|---|---|---|
| c | m | 25.12 | 25.12 | 25.11 |
|   | r | — | — | (25.32) |
|   | *2 |   |   | Small peak |
| a | mm | 45.33 | 45.21 | 45.29 |
|   | mr | — | — | — |
|   | rr | — | — | — |
| b |   |   |   |   |
| m | (m) | 36.46 | 36.46 | 36.44 |
| m | (r) | — | — | Not analyzable as peaks overlapped |
| r | (m) | — | — |   |
| r | (r) | — | — |   |
|   |   |   |   | with Et block peaks |

*1: Boiling acetone-insoluble fraction
*2: —: No distinct peak attributable to at least three head-to-tail styrene chain (a polystyrene chain), was observed by the 13-CNMR measurement commonly carried out in Examples (accumulated number of times: about 5,000 times), and no calculation was accordingly possible.

TABLE 13

| Examples | Value λ | Value m |
|---|---|---|
| Ex. 21 | 78 | 1.0 |
| Ex. 22 *1 | 80 | 1.0 |
| Comp. Ex. 11 *1 | 35 | 0.90 |

*1: Boiling acetone-insoluble fraction

TABLE 15

Main peak shift values (ppm) by 13C-NMR, obtained by using 1,1,2,2-tetrachloroethane d2 as a solvent

| Attribution | | Ex. 23 |
|---|---|---|
| c | m | 25.12 |
|   | r | — |

TABLE 15-continued

Main peak shift values (ppm) by 13C-NMR, obtained by using 1,1,2,2-tetrachloroethane d2 as a solvent

| | Attribution | Ex. 23 |
|---|---|---|
| a | mm | 45.18–45.27 |
| | mr | — |
| | rr | — |
| b | | |
| m | (m) | 36.46 |
| m | (r) | — |
| r | (m) | — |
| r | (r) | — |
| g | | 29.3–29.7 |
| | n | |
| | mmmm | 40.8–40.9 |
| | rrrr | — |
| | o | |
| | mmmm | 43.3–43.6 |
| | rrrr | |
| | j | 42.8–42.9 |
| | k | 43.9–44.1 |

Note: —: No distinct peak was observed by the 13-CNMR measurement commonly conducted in Examples (accumulated number of times: about 5,000 times)
Using 1,1,2,2-tetrachloroethane-d2 as a solvent, the sample was heated and dissolved at 100° C. and then subjected to the measurement. The center peak of the triplet of tetrachloroethane by 13C-NMR had a shift value of 73.89 ppm relative to TMS. Each peak shift value of a copolymer was calculated relative to the center peak value of the triplet of tetrachloroethane being 73.89 ppm.

Example 25

Preparation of Styrene-ethylene Random Copolymer

Rac-dimethylmethylenebis(3-cyclopenta[c]phenanthryl) zirconium dichloride prepared by Preparation D of the above transition metal catalyst component was used as a catalyst, and polymerization was carried out under the conditions shown in the following Table 16.

The polymerization was carried out by using an autoclave of 10 l equipped with a stirrer and a jacket for heating and cooling.

800 ml of dehydrated toluene and 4,000 ml of dehydrated styrene were charged therein, and the resultant mixture was heat-stirred at an inner temperature of 50° C. The reaction system was purged by bubbling about 100 l of nitrogen, and 8.4 mmol of triisobutyl aluminum and 84 mmol (in terms of Al) of methyl alumoxane (MMAO-3A manufactured by TOSOH AKZO Co.) were added thereto. The content of the autoclave was substituted by immediately introducing ethylene, and after stably fixing to a pressure of 0.1 MPa (0 kg/cm$^2$G, atmospheric pressure), about 50 ml of toluene solution having 21 μmol of rac-dinethylmethylenebis(3-cyclopenta[c]phenanthryl)zirconium dichloride (catalyst obtained in Preparation D of the above transition metal catalyst component) and 0.84 mmol of triisobutyl aluminum dissolved was added to the autoclave from a catalyst tank equipped above the autoclave. By maintaining an internal temperature of 50° C. and a pressure of 0.1 MPa, polymerization was carried out for 2.5 hours. After polymerization, the polymerization liquid thus obtained was gradually added in a small amount into an excess amount of methanol vigorously stirred to precipitate a polymer. Under a reduced pressure, the reaction product was dried at 60° C. until no weight change was observed, thereby obtaining 504 g of a polymer.

Examples 26 to 31 (except for Example 27)

The same polymerization procedure as in Example 25 was carried out under the conditions shown in following Table 16.

PMAO or MMAO manufactured by TOSOH-AXZO Co. was used.

Example 27

Polymerization was carried out by using a polymerization tank having a volume of 150 l, equipped with a stirrer and a jacket for heating and cooling.

36 l of dehydrated cyclohexane and 36 l of dehydrated styrene were charged, and the resultant mixture was heat-stirred at an internal temperature of about 500° C. 84 mmol of triisobutyl aluminum and 840 mmol (in terms of Al) of methyl alumoxane (MMAO-3A manufactured by TOSOH-AKZO Co.) were added thereto. After immediately introducing ethylene and after stably fixing a pressure to 0.3 MPa (2 kg/cm$^2$G), from a catalyst tank equipped above the polymerization tank, about 100 ml of toluene solution having 105 μmol of rac-dimethylmethylenebis(3-cyclopenta[c]phenanthryl)zirconium dichloride (the above transition metal catalyst component D) and 10 mmol of triisobutyl aluminum dissolved was added into the polymerization tank. Thereafter, by maintaining a temperature of about 50° C. and a pressure of 0.2 MPa, polymerization was carried out for 3.0 hours.

After polymerization, the polymerization liquid thus obtained was degassed, and was treated in accordance with crumb-forming method as illustrated below, thereby recovering a polymer.

The polymerization liquid was diluted with 72 l of cyclohexane, and the resultant mixture was charged into 300 l water heated at 85° C. and vigorously stirred, containing a dispersant (Pluronic: tradename) over 2 hours. Thereafter, the mixture was stirred at 97° C. for 1 hour, and hot water containing crumb was charged into cooled water to recover the crumb. The crumb thus obtained was dried in air at 50° C., and was then degassed under vacuum at 60° C. to obtain 9.5 kg of a satisfactory polymer of crumb-shape having a size of about several mm.

Preparation E of Transition Metal Catalyst Component

Rac-dimethylmethylene(3-cyclopenta[c]phenanthryl)(1-indenyl)zirconium dichloride (another name: rac{CpPhen-CMe$_2$-Ind}ZrCl$_2$) was prepared in the following manner. CpPhen represents cyclopenta[c]phenanthryl), E-1 Preparation of 1,1-isopropylidene-3-cyclopenta[c]phenanthrene Preparation of 1,1-isopropylidene-3-cyclopenta[c]phenanthrene was carried out with reference to the preparation of 6,6-diphenylfulvene in accordance with the description of Can. J. Chem., vol. 62, 1751 (1984). However, as starting materials, acetone was used in place of benzophenone and 1H or 3H-cyclopenta[c]phenanthrene was used in place of cyclopentadiene.

E-2 Preparation of isopropylidene(1-indene)3-cyclopenta[c]phenanthrene)

In an Ar atmosphere, 14 mmol of indene was dissolved in 50 ml of THF, and an equivalent amount of BuLi was added thereto at 0° C., and the resultant mixture was stirred for about 10 hours. 20 ml of THF having 14 mmol of 1,1-isopropylidene-3-cyclopenta[c]phenanthrene dissolved was added thereto, and the mixture was stirred at 0° C. to room temperature overnight. 50 ml of water and 100 ml of diethyl ether were added thereto, and the mixture was shaked to separate an organic phase, and the organic phase thus separated was washed with saturated salt water and was then dried with sodium sulfate, and the solvent was distilled off under reduced pressure. The product thus obtained was further purified by a column to obtain isopropylidene (1-indene)(3-clopenta[c]phenanthrene). The yield was 32%.
3 Preparation of rac-dimethylmethylene(3-cyclopenta[c]phenanthryl)(1-indenyl)zirconium dichloride The aimed product was prepared in the same manner s in Preparation D-3 of rac-dimethylmethylenebis(3-cyclopenta[c]phenanthryl)zirconium dichloride. The obtained product was yellow orange powder and the yield was 28%.

According to the 1H-NMR spectrum measurement, it was found to have peaks at 2.43 ppm (3H,s), 2.47 ppm (3H,s), 6.28 ppm (1H,d), 6.36 ppm (1H,d), 6.71(1H,dd), 7.08–7,97 ppm (12H,m) and 8.88 ppm (1H,d).

Chloroform H peak in chloroform-d was observed at 7.254 ppm, and the peak of impurity toluene was observed at 2.3499 ppm. The measurement was carried out using $CDCl_3$ as a solvent.

Example 32

By using 8.4 μmol of rac{$CpPhen-CMe_2-Ind$}$ZrCl_2$ obtained in Preparation E of transition metal catalyst component as a catalyst, polymerization was carried out under the conditions shown in the following Table 16.

Table 16 shows the results and the polymerization conditions of respective Examples.

TABLE 17

| Examples | St content (mol %) | $Mw/10^4$ | Mw/Mn | Glass transition temperature (° C.) | Melting point (° C.) |
|---|---|---|---|---|---|
| Example 25 | 60.0 | 28.4 | 2.4 | 58 | Melting point was not observed. |
| Example 26 | 70.0 | 24.6 | 2.2 | 56 | Melting point was not observed. |
| Example 27 | 53.5 | 23.0 | 2.2 | 49 | Melting point was not observed. |
| Example 28 | 45.0 | 18.0 | 22 | 22 | Melting point was not observed. |
| Example 29 | 9.1 | 12.1 | 2.2 | −21 | 93 |
| Example 30 | 5.5 | 10.0 | 2.1 | −26 | 103 |
| Example 31 | 4.3 | 11.7 | 2.1 | 24 | 105 |
| Example 32 | 7.0 | 11.6 | 2.0 | −24 | 93 |

FIGS. 47 and 48 illustrate a GPC chart and a DSC chart of the copolymer obtained in Example 25 as a typical example of the styrene-ethylene copolymer of the present invention. In the GPC measurement of a polymer obtained in each Example, the GPC curves obtained by different detectors (RI and UV) correspond to each other within an error range of experiment as illustrated in FIG. 47, and this fact proves that the copolymer obtained has quite uniform composition distribution.

TABLE 16

| Examples | Catalyst | Catalyst amount (μmol) | Cocatalyst (mmol) MAO | Solvent amount (ml) | Styrene amount (ml) | Ethylene pressure (MPa) | Polymerization pressure (° C.) | Polymerization time (h) | Yield (g) | Productivity (g/mol-cat)/$10^6$ | St content (mol %) |
|---|---|---|---|---|---|---|---|---|---|---|---|
| Example 25 | D | 21 | M84 | T800 | 4000 | 0.1 | 50 | 2.5 | 504 | 24.0 | 60.0 |
| Example 26 | D | 84 | M84 | T800 | 4000 | 0.08 | 50 | 4.0 | 740 | 8.8 | 70.0 |
| Example 27 | D | .105 | M840 | C36L | 36L | 0.3 | 50 | 3.0 | 9.5 kg | 91 | 53.5 |
| Example 26 | D | 8.4 | P8.4 | T2000 | 2800 | 1.1 | 70 | 2.0 | 570 | | 45.0 |
| Example 29 | D | 8.4 | P21 | T4000 | 800 | 1.1–0.5 | 70–92 | 0.5 | 675 | 80 | 9.1 |
| Example 30 | D | 8.4 | P8.4 | T4000 | 800 | 1.1–0.9 | 70–79 | 0.5 | 553 | 66 | 5.5 |
| Example 31 | D | 8.4 | P8.4 | T4000 | 800 | 1.1 | 50–62 | 0.5 | 543 | 65 | 4.3 |
| Example 32 | E | 8.4 | P8.4 | T4000 | 800 | 1.1 | 70 | 3.0 | 470 | 56 | 7.0 |

P; PMAO, M; MMAO, T; toluene, C; cyclohexane
Transition metal compounds used as catalysts:
D: rac-dimethyl methylenebis (3-cyclopenta[c]phenanthryl) zirconium dichloride
E: rac-dimethyl methylene (3-cyclopenta[c]phenanthryl)(1-indenyl) zirconium dichloride Table 17 shows styrene contents, molecular weights measured by GPC, glass transition points measured by DSC and melting points of the polymers obtained.

Melting point was measured with 10 mg of a sample treated at 60 to 70° C. for about 10 hours in a nitrogen stream at a temperature raising rate of 20° C./min from room temperature to 250° C. to confirm presence or absence of melting point between 70° C. and 250° C. (1st-run). The sample was maintained at 250° C. for 10 minutes, and was then quenched with liquid nitrogen, and was then heated from −100° C. to 280° C. at a temperature raising rate of 10° C./min to measure glass transition point (Tg) (2nd-run).

Also, the glass transition point determined by DSC is one as illustrated in Table 17, and this fact also proves that the copolymer has uniform composition.

Each copolymer obtained in each Example was press-molded at 180° C., and was subjected to annealing at 50° C. for 1 week, and was subjected to x-ray diffraction analysis, the results of which are shown in the following Table 18. With regard to each copolymer of each Example of the present invention, a diffraction peak derived from ethylene-styrene alternating structure was not observed. However, with regard to a copolymer having a styrene content of about at most 15 mol %, a diffraction peak derived from ethylene chain structure (polyethylene) crystal was observed. On the other hand, with regard to each copolymer of each Comparative Example, a diffraction peak derived from ethylene-styrene alternating structure was clearly observed.

TABLE 18

| Examples | St content (mol %) | Results of X-ray diffraction |
|---|---|---|
| Example 25 | 60.0 | No diffraction peak was observed. |
| Example 26 | 70.0 | No diffraction peak was observed. |
| Example 27 | 53.5 | No diffraction peak was observed. |
| Example 28 | 45.0 | No diffraction peak was observed. |
| Example 29 | 9.1 | Diffraction peak derived from polyethylene crystal was observed. |
| Example 30 | 5.5 | Diffraction peak derived from polyethylene crystal was observed. |
| Example 31 | 4.3 | Diffraction peak derived from polyethylene crystal was observed. |
| Example 32 | 7.0 | Diffraction peak derived from polyethylene crystal was observed. |

FIG. 49 illustrates a diffraction spectrum of the annealed copolymer of Example 25, and FIG. 50 illustrates a diffraction spectrum of a copolymer having a crystal structure derived from ethylene-styrene alternating structure.

Table 19 shows physical properties of a copolymer sample obtained in Example 25 and a copolymer sample annealed at 50° C. for 1 week. The annealing treatment did not cause any substantial change in mechanical properties, hardness, transparency and the like. Also, it is evident that the copolymer of the present invention has a high transparency and a low haze before and after annealing treatment. The copolymer of the present invention is a copolymer in which a change in physical properties as a lapse of time is very small.

Tensile modulus of elasticity, tensile breaking extension and tensile strength at break were measured in accordance with JIS K 7113 by molding to form a sheet having a thickness of 1 mm by heat-press method (200° C., 4 minutes, 50 kg/cm$^2$G) and punching to prepare a sample of No. 2 dumbbell-like shape.

Total light transmittance and haze were measured in accordance with JIS K-7105 by using a sample of 1 mm sheet formed in the same manner as mentioned above and using a turbidity meter NDH2000 manufactured by Nihon Denshoku Kogyo K.K.

Surface hardness (Shore A, D hardness) was measured in accordance with JIS K-7215.

TABLE 19

|  | Copolymer prepared in Example 25 (before annealing) | Copolymer prepared in Example 25 (after annealing) |
|---|---|---|
| Breaking elongation (%) | 6 | 6 |
| Yield strength (MPa) | Yield point was not observed. | Yield point was not observed. |
| Breaking point strength (MPa) | 31.5 | 32.8 |
| Tensile elastic modulus (MPa) | 804 | 907 |
| Haze (%) | 14.5 | 14.1 |
| Total light transmittance (%) | 85.2 | 85.9 |
| Hardness (shore-D) | 63 | 61 |
| Hardness (shore-A) | 98 | 98 |

FIGS. 51 and 52 illustrate 13C-NMR spectra of polymers obtained in Examples 26 and 29.

Peak shift values (13C-NMR) derived from 2 or more head-to-tail styrene chains of copolymers obtained in respective Examples are illustrated in Table 20.

A structure index λ value of a copolymer obtained in each Example was determined in accordance with the above formula (i). λ values and m values obtained with regard to each Example are shown in the following Table 21.

Isotactic diad (mesodiad) index m of alternating structure was determined in accordance with the above formula (ii).

By carrying out 13C-NMR measurement, a peak derived from head-to-tail styrene chain structure can be clearly observed.

A ratio x of an aromatic vinyl compound unit amount (derived from head-to-tail chain structure of aromatic vinyl compound unit contained in a copolymer) to the total aromatic vinyl compound unit amount was determined by the following formula.

$$x = xa/xb \times 100 \qquad (iv)$$

In the above formula, xa is a total value of peak areas derived from main chain methine carbons of head-to-tail chain structures of two or more aromatic vinyl compound units. For example, in the 13C-NMR measurement based on TMS, a total value of peak (n) observed at 40.4–41.0 ppm and peak (j) observed at 42.3–44.6 ppm. xb is a total value of peak areas derived from main chain methine carbons of total aromatic vinyl compound units contained in a copolyner.

The following Table 21 shows a x value of a copolymer of each Example.

TABLE 20

| | Main peak shift value (ppm) by 13C-NMR using tetrachloroethane-d as a solvent | | | | | | | |
|---|---|---|---|---|---|---|---|---|
| Attribution | Example 1 | Example 2 | Example 3 | Example 4 | Example 5 | Example 6 | Example 7 | Example 8 |
| n | | | | | Note 1) | | | |
| Note 2 | 40.4–40.7 | 40.6–40.9 | 40.5–40.8 | 40.5–40.9 | — | — | — | — |
| Note 3 | — | — | — | — | — | — | — | — |
| o | | | | | | | | |
| Note 2 | 43.0–43.4 | 43.0–43.5 | 43.0–43.6 | 43.1–43.5 | — | — | — | — |
| Note 3 | — | — | — | — | — | — | — | — |
| j | 42.3–42.7 | 42.4–42.7 | 42.6–42.7 | 427–42.9 | 43.1, 43.4 | 42.9 | 43.3 | — |
| k | 43.7–44.1 | 43.8–44.1 | 43.8–44.3 | 43.9–44.4 | 44.2 | 44.3 | 43.9–44.4 | — |

Note 1): Clear peaks could not be observed by 13C-NMR measurement (about 10,000 times integration) conducting usual determination of Examples.
Note 2) m, mm, mmm or mmmm, Note 3) r, rr, rrr or rrrr Sample was measured by heat-dissolving at about 100° C. and using tetrachloroethane-d as a solvent.

The center peak of triplet 13C-NMR peak of tetrachloroethane showed a shift value of 73.89 ppm to TMS. Each peak shift value of coplymers was determined by taking the triplet center peak value of tetrachloroethane as 73.89 ppm.

TABLE 21

| Examples | St content (mol %) | λ value | m value | x value |
|---|---|---|---|---|
| Example 25 | 60.0 | 20 | >0.95 | about 60 |
| Example 26 | 70.0 | 18 | >0.95 | about 70 |
| Example 27 | 53.5 | 33 | >0.95 | 29 |
| Example 28 | 45.0 | 30 | >0.95 | 23 |
| Example 29 | 9.1 | 4 | >0.95 | 5 |
| Example 30 | 5.5 | 3 | >0.95 | 3 |
| Example 31 | 4.3 | 2 | >0.95 | 2 |
| Example 32 | 7.0 | 3 | >0.95 | Unmeasured |

In the 13C-NMR measurement, peaks derived from two or more head-to-tail styrene chain structures were observed. The aromatic vinyl compound-ethylene copolymer of the present invention provides a clear peak derived from head-to-tail styrene chain structure, which can be observed even by usual 13C-NMR measurement (about 20,000 times integration), even when a styrene content is less than 10 mol %.

In the present Examples, methine carbon (j) derived from head-to-tail chain structure of two styrene units was observed in the range of from 42.3 to 43.6 ppm, and methine carbon (n) derived from head-to-tail chain structure of 3 or more styrene units was observed in the range of from 40.4 to 41.0 ppm.

Further, the aromatic vinyl compound-ethylene copolymer of the present invention is a copolymer having a high random property (low alternating property), the λ value of which satisfies the formula ($i^A$).

Example 33

Preparation of styrene-1-octene copolymer

Rac-dimethylmethylenebis(3-cyclopenta[c]phenanthryl) zirconium dichloride prepared by Preparation D of the above transition metal catalyst component was used as a catalyst, and polymerization was carried out under the following conditions.

The polymerization was carried out by using an autoclave of 10 equipped with a stirrer and a jacket for heating and cooling.

4,400 ml of dehydrated toluene and 400 ml of 1-octene were charged therein, and the resultant mixture was heat-stirred at an inner temperature of 70° C. The reaction system was purged by bubbling about 100 l of nitrogen, and 8.4 mmol of triisobutyl aluminum and 8.4 mmol (in terms of Al) of methyl alumoxane (MMAO-3A manufactured by TOSOH AKZO Co.) were added thereto. The content of the autoclave was substituted by immediately introducing ethylene, and after stably fixing to a pressure of 1.1 MPa (10 kg/cm²G, atmospheric pressure), about 50 ml of toluene solution having 1.3 μmol of rac-dimethylmethylenebis(3-cyclopenta[c]phenanthryl)zirconium dichloride (catalyst obtained in Preparation D of the above transition metal catalyst component) and 0.84 mmol of triisobutyl aluminum dissolved was added to the autoclave from a catalyst tank equipped above the autoclave. By maintaining the internal temperature of 70° C. and the pressure of 1.1 MPa, polymerization was carried out for 0.5 hour. After polymerization, the polymerization liquid thus obtained was gradually added in a small amount into an excess amount of methanol vigorously stirred to precipitate a polymer. Under a reduced pressure, the reaction product was dried at 60° C. until no weight change was observed, thereby obtaining 760 g of a polymer. Catalyst activity for 1 hour was 1,170 t/mol catalyst.

The polymer thus obtained had an octene content of 9.5 mol % by 1H-NMR measurement, a weight average molecular weight (Mw) of 87,000 by GPC measurement and a molecular weight distribution (Mw/Mn) of 2.3, and also had a melting point of 90° C and a glass transition point of −52° C. by DSC measurement.

What is claimed is:

1. A method for producing a polymer selected from the group consisting of an aromatic vinyl compound-olefin copolymer, an aromatic vinyl compound polymer, an olefin polymer and an olefin copolymer, comprising polymerizing in the presence of a polymerization catalyst comprising a transition metal compound and a cocatalyst, wherein the transition metal compound has the following formula (1'):

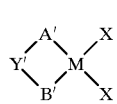

(1')

wherein A' is an unsubstituted or substituted cyclopentaphenianthryl group of the following formula K-2' or K-3':

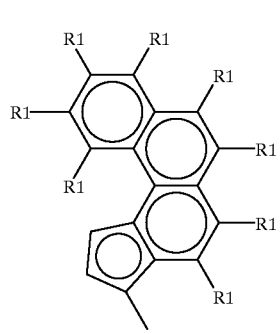

(K-2')

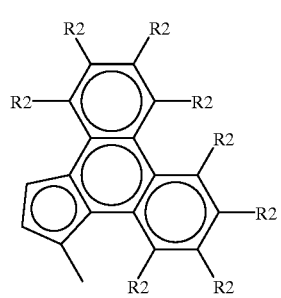

(K-3')

wherein in the above formulas K-2' and K-3', each of R1 and R2 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$, (wherein each R is a $C_{1-10}$ hydrocarbon group), provided that a plurality of R1 and a plurality of R2 may be the same or different, respectively, and each pair of adjacent R1 and adjacent R2 may together, with the atoms joining them, form a 5- to 8-member aromatic or aliphatic ring, B' is an unsubstituted or substituted cyclopentaphenanthryl group of the same chemical formula as A', an unsubstituted or substituted benzindenyl group of the following formula K-4', K-5' or K-6', or an unsubstituted or substituted cyclopentadienyl group, an unsubstituted or substituted indenyl group or an unsubstituted or substituted fluorenyl group, of the following formula K-7', K-8' or K-9':

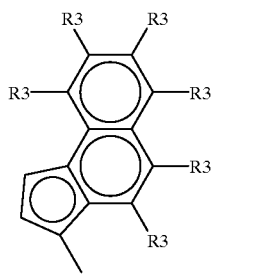
(K-4')

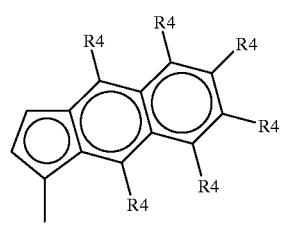
(K-5')

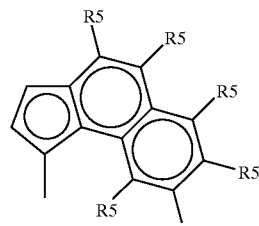
(K-6')

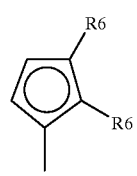
(K-7')

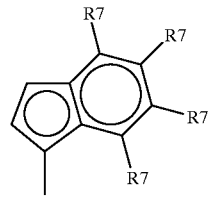
(K-8')

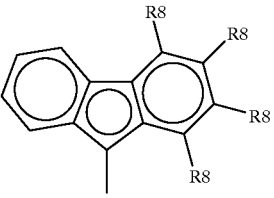
(K-9')

wherein in the above formulas K-4', K-5' and K-6' each of R3, R4 and R5 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), provided that a plurality of R3, a plurality of R4 and a plurality of R5 may be the same or different, respectively, and each pair of adjacent R3, adjacent R4 and adjacent R5 may together, with the atoms joining them, form a 5- to 8-member aromatic or aliphatic ring, except for forming an unsubstituted cyclopentaphenanthyrene group, wherein in the above formulas K-7', K-8' and K-9' each of R6, R7 and R8 is hydrogen, a $C_{1-20}$ alkyl group, a $C_{6-10}$ aryl group, a $C_{7-20}$ alkylaryl group, a halogen atom, $OSiR_3$, $SiR_3$ or $PR_2$ (wherein each R is a $C_{1-10}$ hydrocarbon group), provided that a plurality of R6, a plurality of R7 and a plurality of R8 may be the same or different, respectively, when both A' and B' are unsubstituted or substituted cyclopentaphenanthryl groups, they may the same or different, Y' is a methylene group or a boron atom, which has bonds to A' and B' and which has, as substituents, hydrogen or a $C_{1-15}$ hydrocarbon group, wherein the substituents may be the same or different from each other, or Y' may have, together with the substituents, a cyclic structure including a cyclohexylidene group or a cyclopentylidene group, X is hydrogen, a halogen atom, a $C_{1-15}$ alkyl group, a $C_{6-10}$ aryl group, a $C_8$–$C_{12}$ alkylaryl group, a silyl group having $C_1$–$C_4$ hydrocarbon substituent, $C_1$–$C_{10}$ alkoxy group or a dialkylamide group having a $C_1$–$C_6$ alkyl substituent, and M is zirconium, hafnium or titanium.

2. The method of claim 1, wherein the polymer is an aromatic vinyl compound-olefin copolymer.

3. The method of claim 1, wherein the polymer is an aromatic vinyl compound polymer.

4. The method of claim 1, wherein the polymer is an olefin polymer or an olefin copolymer.

* * * * *

UNITED STATES PATENT AND TRADEMARK OFFICE
CERTIFICATE OF CORRECTION

PATENT NO. : 6,329,479 B1
DATED : December 11, 2001
INVENTOR(S) : Arai et al.

It is certified that error appears in the above-identified patent and that said Letters Patent is hereby corrected as shown below:

<u>Title page,</u>
Item [30], the Foreign Application Priority information should read:

-- [30]     Foreign Application Priority Data

| Apr. 17, 1997 | (JP)..........................9-100527 |
| Apr. 17, 1997 | (JP)..........................9-100528 |
| Apr. 17, 1997 | (JP)..........................9-100529 |
| Aug. 28, 1997 | (JP)..........................9-232084 |
| Sep. 7, 1998 | (JP).........................10-252222 |
| Sep. 9, 1998 | (JP).........................10-254907 -- |

Signed and Sealed this

Thirteenth Day of August, 2002

Attest:

JAMES E. ROGAN
*Attesting Officer*     *Director of the United States Patent and Trademark Office*